US010598597B2

(12) United States Patent
Bahlman et al.

(10) Patent No.: US 10,598,597 B2
(45) Date of Patent: Mar. 24, 2020

(54) MULTIFOCAL IMAGING SYSTEMS AND METHOD

(71) Applicant: Massachusetts Institute of Technology, Cambridge, MA (US)

(72) Inventors: Karsten Bahlman, Cambridge, MA (US); Ki-Hean Kim, Belmont, MA (US); Timothy Ragan, Somerville, MA (US); Peter T. C. So, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/815,536

(22) Filed: Nov. 16, 2017

(65) Prior Publication Data

US 2018/0202935 A1 Jul. 19, 2018

Related U.S. Application Data

(63) Continuation of application No. 11/442,702, filed on May 25, 2006, now abandoned.
(Continued)

(51) Int. Cl.
*G01N 21/64* (2006.01)
*G02B 21/00* (2006.01)
*G02B 21/16* (2006.01)

(52) U.S. Cl.
CPC ..... *G01N 21/6452* (2013.01); *G01N 21/6458* (2013.01); *G01N 21/6486* (2013.01);
(Continued)

(58) Field of Classification Search
CPC ........... G01N 21/6452; G01N 21/6458; G01N 21/6486; G02B 21/16; G02B 21/0032; G02B 21/0076; G02B 21/002
(Continued)

(56) References Cited

U.S. PATENT DOCUMENTS 4,960,330 A 10/1990 Kerschmann
5,109,149 A 4/1992 Leung
(Continued)

FOREIGN PATENT DOCUMENTS

EP 1580586 A1 9/2005
JP 2000-193889 A 7/2000
(Continued)

OTHER PUBLICATIONS

Andresen et al., Time-multiplexed multifocal multiphoton microscope. Opt Lett. Jan. 15, 2001;26(2):75-7.
(Continued)

*Primary Examiner* — Tung T Vo
(74) *Attorney, Agent, or Firm* — McCarter & English, LLP

(57) ABSTRACT

In the systems and methods of the present invention a multifocal multiphoton imaging system has a signal to noise ratio (SNR) that is reduced by over an order of magnitude at imaging depth equal to twice the mean free path scattering length of the specimen. An MMM system based on an area detector such as a multianode photomultiplier tube (MAPMT) that is optimized for high-speed tissue imaging. The specimen is raster-scanned with an array of excitation light beams. The emission photons from the array of excitation foci are collected simultaneously by a MAPMT and the signals from each anode are detected using high sensitivity, low noise single photon counting circuits. An image is formed by the temporal encoding of the integrated signal with a raster scanning pattern. A deconvolution procedure taking account of the spatial distribution and the raster temporal encoding of collected photons can be used to improve decay coefficient. We demonstrate MAPMT-based MMM can provide significantly better contrast than CCD-based existing systems.

33 Claims, 38 Drawing Sheets

Related U.S. Application Data

(60) Provisional application No. 60/684,608, filed on May 25, 2005.

(52) U.S. Cl.
CPC ....... *G02B 21/002* (2013.01); *G02B 21/0032* (2013.01); *G02B 21/0076* (2013.01); *G02B 21/16* (2013.01)

(58) Field of Classification Search
USPC ..................................................... 348/82, 79
See application file for complete search history.

(56) References Cited

U.S. PATENT DOCUMENTS

| | | | |
|---|---|---|---|
| 5,139,338 A | 8/1992 | Pomerantz et al. | |
| 5,156,019 A | 10/1992 | McCormick | |
| 5,233,197 A | 8/1993 | Bowman et al. | |
| 5,583,342 A | 12/1996 | Ichie | |
| 5,633,695 A | 5/1997 | Feke et al. | |
| 5,691,839 A | 11/1997 | Kobayashi | |
| 5,740,708 A | 4/1998 | Tabone | |
| 5,783,814 A | 7/1998 | Fairley et al. | |
| 6,020,591 A | 2/2000 | Harter et al. | |
| 6,028,306 A | 2/2000 | Hayashi | |
| 6,219,179 B1 | 4/2001 | Nielsen et al. | |
| 6,248,988 B1 | 6/2001 | Krantz | |
| 6,387,653 B1 | 5/2002 | Voneiff et al. | |
| 6,392,795 B2 | 5/2002 | Okada | |
| 6,423,960 B1 | 7/2002 | Engelhardt et al. | |
| 6,449,039 B1* | 9/2002 | Bouzid | G02B 21/002 |
| | | | 250/458.1 |
| 6,496,267 B1 | 12/2002 | Takaoka | |
| 6,603,537 B1 | 8/2003 | Dietz et al. | |
| 6,623,977 B1* | 9/2003 | Farquharson | G01N 21/658 |
| | | | 356/301 |
| 7,003,143 B1 | 2/2006 | Hewitt et al. | |
| 7,009,699 B2 | 3/2006 | Wolleschensky et al. | |
| 7,092,557 B2 | 8/2006 | Eisfeld et al. | |
| 7,110,118 B2 | 9/2006 | Unlu et al. | |
| 7,115,885 B2 | 10/2006 | Hell | |
| 7,139,415 B2 | 11/2006 | Finkbeiner | |
| 7,197,193 B2 | 3/2007 | Li et al. | |
| 7,209,287 B2 | 4/2007 | Lauer | |
| 7,215,469 B2 | 5/2007 | Nakata et al. | |
| 7,217,573 B1* | 5/2007 | Oshida | G01N 21/6428 |
| | | | 250/347 |
| 7,274,446 B2 | 9/2007 | Wolleschensky et al. | |
| 7,329,860 B2 | 2/2008 | Feng et al. | |
| 7,366,394 B2 | 4/2008 | Takamatsu et al. | |
| 7,372,985 B2 | 5/2008 | So et al. | |
| 7,502,107 B2 | 3/2009 | Mohanty et al. | |
| 7,561,326 B2 | 7/2009 | Funk et al. | |
| 7,724,937 B2 | 5/2010 | So et al. | |
| 7,749,754 B2 | 7/2010 | Sherwood et al. | |
| 7,767,414 B1 | 8/2010 | Smith et al. | |
| 8,771,978 B2 | 7/2014 | Ragan | |
| 2002/0190212 A1* | 12/2002 | Boas | A61B 5/0068 |
| | | | 250/341.1 |
| 2002/0191884 A1* | 12/2002 | Letant | G01N 21/774 |
| | | | 385/12 |
| 2003/0132394 A1 | 7/2003 | Wolleschensky et al. | |
| 2004/0032650 A1 | 2/2004 | Lauer | |
| 2004/0076319 A1 | 4/2004 | Fauver et al. | |
| 2004/0110206 A1* | 6/2004 | Wong | G01N 21/6408 |
| | | | 435/6.14 |
| 2004/0125372 A1* | 7/2004 | Walla | G01J 3/4406 |
| | | | 356/318 |
| 2004/0228568 A1* | 11/2004 | Letant | G01N 21/774 |
| | | | 385/12 |
| 2004/0257562 A1* | 12/2004 | Wachsmuth | G01J 3/4406 |
| | | | 356/317 |
| 2004/0257646 A1* | 12/2004 | Wachsmuth | G01J 3/36 |
| | | | 359/385 |
| 2005/0024637 A1* | 2/2005 | Olschewski | G01N 21/64 |
| | | | 356/318 |
| 2005/0036667 A1 | 2/2005 | So et al. | |
| 2005/0046836 A1* | 3/2005 | Olschewski | G01N 21/6428 |
| | | | 356/318 |
| 2005/0046848 A1 | 3/2005 | Cromwell et al. | |
| 2005/0259319 A1* | 11/2005 | Brooker | G02B 21/0076 |
| | | | 359/368 |
| 2005/0260764 A1* | 11/2005 | Grigsby, Jr. | G01N 21/6428 |
| | | | 436/172 |
| 2006/0012875 A1* | 1/2006 | Wolleschensky | G01N 21/6458 |
| | | | 359/388 |
| 2006/0139637 A1 | 6/2006 | Cho et al. | |
| 2006/0158655 A1 | 7/2006 | Everett et al. | |
| 2006/0179992 A1 | 8/2006 | Kermani | |
| 2006/0211752 A1 | 9/2006 | Kohn et al. | |
| 2007/0038121 A1 | 2/2007 | Feldman et al. | |
| 2007/0057211 A1 | 3/2007 | Bahlman et al. | |
| 2007/0254280 A1 | 11/2007 | Lexow et al. | |
| 2007/0258122 A1 | 11/2007 | Champoulov et al. | |
| 2007/0260138 A1 | 11/2007 | Feldman et al. | |
| 2008/0102006 A1 | 5/2008 | Kram et al. | |
| 2008/0130093 A1 | 6/2008 | Silberberg et al. | |
| 2008/0154128 A1 | 6/2008 | Milner | |
| 2010/0028978 A1 | 2/2010 | Angros | |
| 2010/0323445 A1 | 12/2010 | Hayworth et al. | |
| 2013/0142413 A1 | 6/2013 | So et al. | |

FOREIGN PATENT DOCUMENTS

| | | |
|---|---|---|
| JP | 2005-017127 A | 1/2005 |
| JP | 2005-508489 A | 3/2005 |
| JP | 2005-275206 A | 10/2005 |
| JP | 2006-031004 A | 2/2006 |
| JP | 2006-178472 A | 7/2006 |
| WO | 1998/02851 A1 | 1/1998 |
| WO | 2001/40769 A2 | 6/2001 |
| WO | 2001/42796 A1 | 6/2001 |
| WO | 2002/084265 A1 | 10/2002 |
| WO | 2006/127967 A2 | 11/2006 |

OTHER PUBLICATIONS

Bewersdorf et al., Multifocal multiphoton microscopy. Opt Lett. May 1998;23(9):655-7.

Bird et al., Fibre-optic two-photon scanning fluorescence microscopy. J Microsc. Oct. 2002;208(Pt 1):35-48.

Bird et al., Two-photon fluorescence endoscopy with a micro-optic scanning head. Opt Lett. Sep. 1, 2003;28 (17):1552-4.

Buist et al., Real time two-photon absorption microscopy using multi point excitation. Journal of Microscopy. Nov. 1998;192(2):217-226.

Denk et al., Two-photon Laser Scanning fluorescence microscopy. Science. Apr. 6, 1990;248:73-76.

Helmchen et al., A miniature head-mounted two-photon microscope: High-resolution brain imaging in freely moving animals. Neuron. Sep. 27, 2001;31(6):903-12.

Helmchen et al., Enhanced two-photon excitation through optical fiber by single-mode propagation in a large core. Appl Opt. May 20, 2002;41(15):2930-4.

Jung et al., Multiphoton endoscopy. Opt Lett. Jun. 1, 2003;28(11):902-4.

Kim et al., High speed handheld multiphoton multifoci microscopy. Proc. SPIE Int. Soc. Opt. Eng.; Progress in Biomedical Optics and Imaging—Multiphoton microscopy in the Biomedical Sciences IV. Jun. 2004;5353:267-272.

Kim et al., Optical biopsy in high-speed handheld miniturized multifocal multiphoton microscopy. Progr. Biomed. Opt. Imaging Proc. SPIE: Multiphoton Microscopy in the Biomedical Sciences V. Mar. 2005;5700:14-22.

Kim et al., Usage of multi anode PMT on the multi-photon fluorescence spectroscopy and video rate microscopy. 24th Annual Conference and the Annual Fall Meeting of the Biomedical Engineering Society EMBS/BMES Conference. Proceedings of the Second Joint Engineering in Medicine and Biology, p. 1206. 2002.

(56) References Cited

OTHER PUBLICATIONS

Leveque-Fort et al., Fluorescence lifetime imaging with multifocal two-photon microscope. Proceedings of SPIE—The International Society for Optical Engineering. Jun. 2004;5323(1):99-107.
Leveque-Fort et al., Time-resolved multifocal multiphoton microscopy. Proceedings of SPIE—The International Society for Optical Engineering. Jun. 2003;5139:173-179.
Nielsen et al., High efficiency beam splitter for multifocal multiphoton microscopy. J Microsc. Mar. 2001;201(Pt 3):368-76.
Sacconi et al., Microphoton multifocal microscopy exploiting a diffractive optical element. Opt Lett. Oct. 15, 2003;28 (20):1918-20.
Webb et al., A wide-field time-domain fluorescence lifetime imaging microscope with optical sectioning. American Institute of Physics, Review of Scientific Instruments. Mar. 2002;5139:1898-1907.
Cambridge Technology, Inc., Model 6240H Galvanometer Optical Scanner, Instruction Manual. www.cambridgetechnology.com. 22 pages, Sep. 23, 2004.
Dubois et al., High-resolution full-field optical coherence tomography with a Linnik microscope. Appl Opt. Feb. 1, 2002;41(4):805-12.
Helmchen, Miniaturization of fluorescence microscopes using fibre optics. Exp Physiol. Nov. 2002;87(6):737-45.
Kim et al., High-speed, two-photon scanning microscope. Appl Opt. Oct. 1, 1999;38(28):6004-9.
Kim et al., Three-Dimensional Image Cytometer Based on a High-Speed Two-Photon Scanning Microscope. Proc SPIE. Apr. 2001;4262:238-46.
Konig, Multiphoton microscopy in life sciences. J Microsc. Nov. 2000;200(Pt 2):83-104.
So et al., Two-photon excitation fluorescence microscopy. Annu Rev Biomed Eng. Aug. 2000;2:399-429.

\* cited by examiner

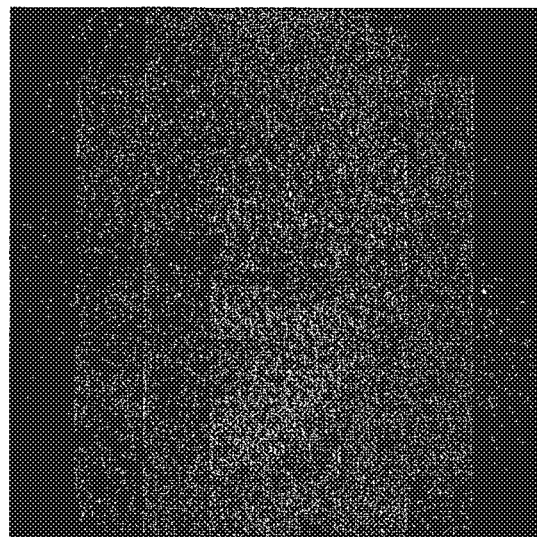
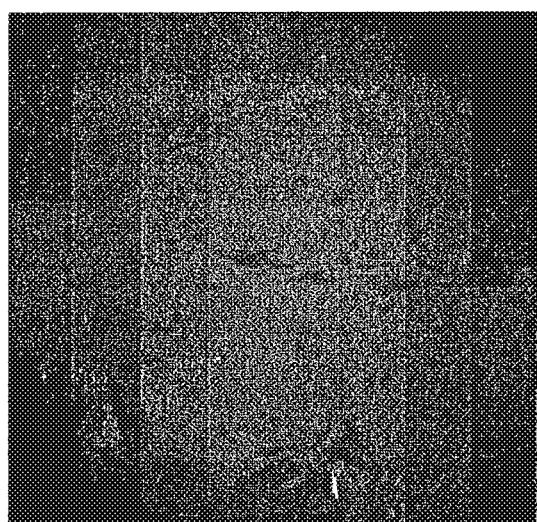
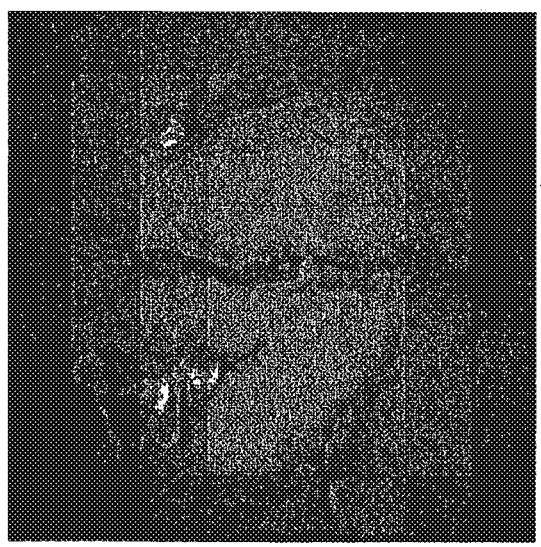
FIG. 2A Stratum corneum layer
FIG. 2B stratum granular
FIG. 2C basal layer $\{s_s\}_{est} = [C]_{est}^{-1}\{s_{acq}\}$ Deconvolution

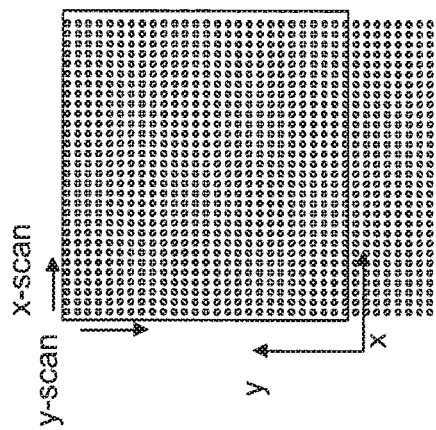
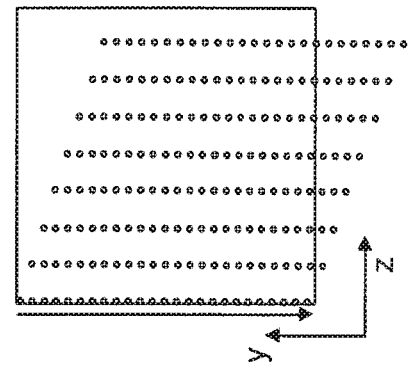
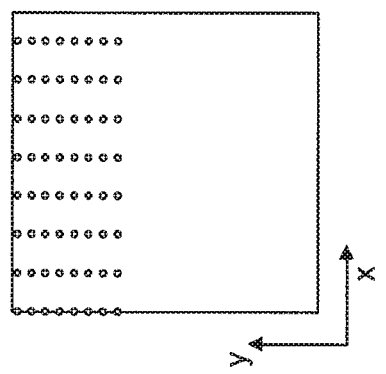
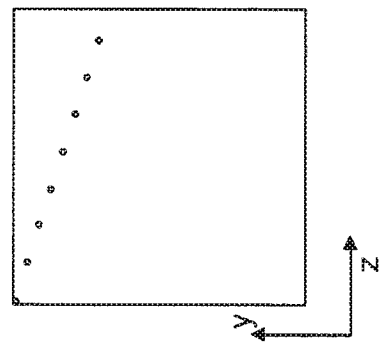
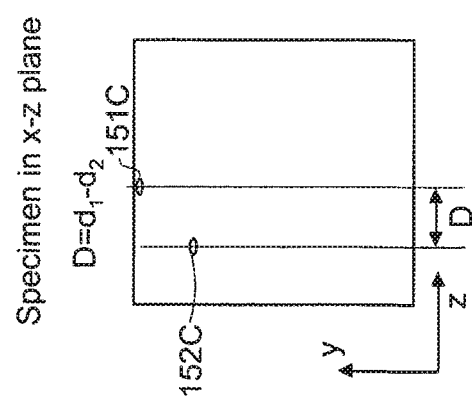

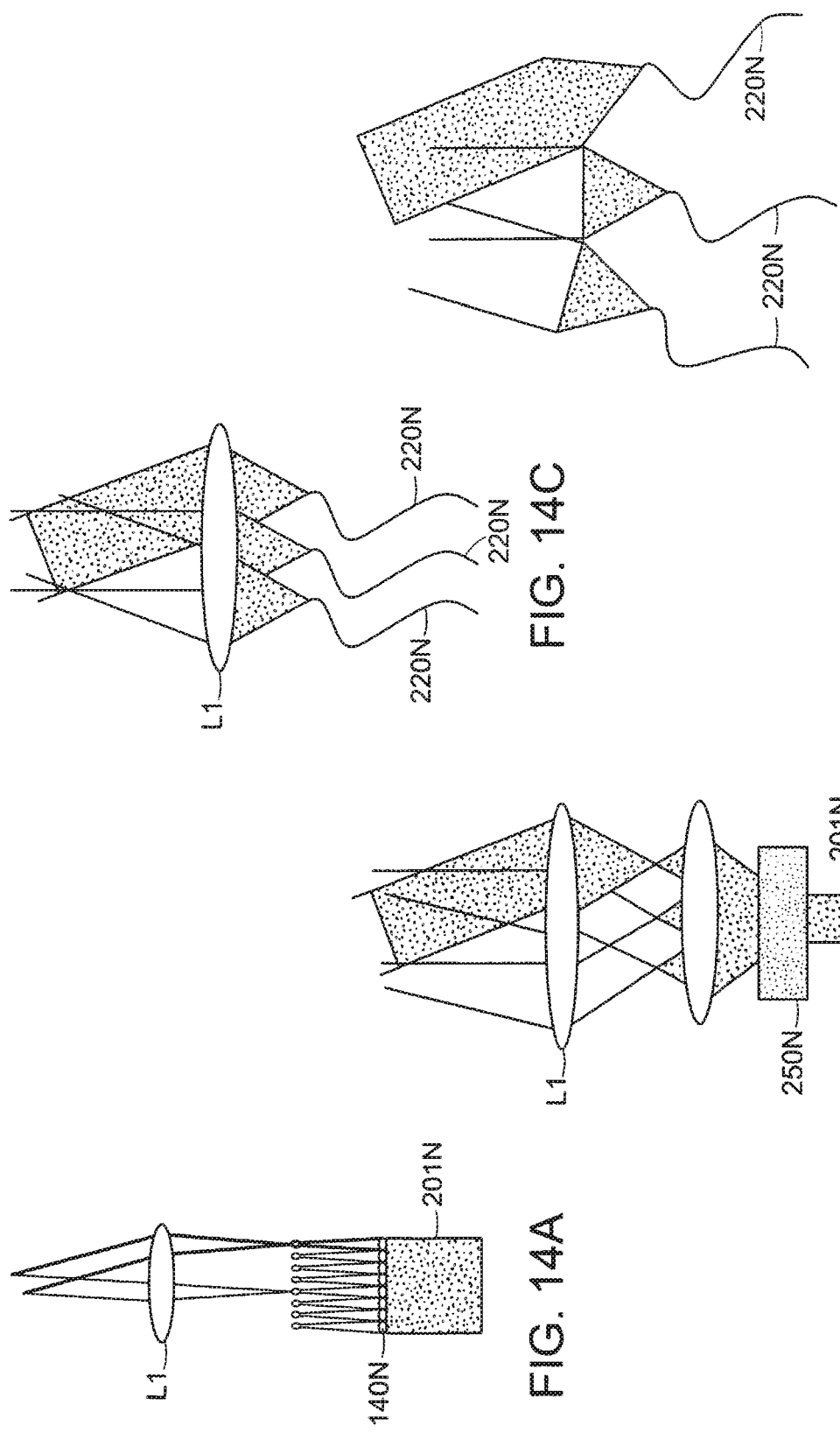

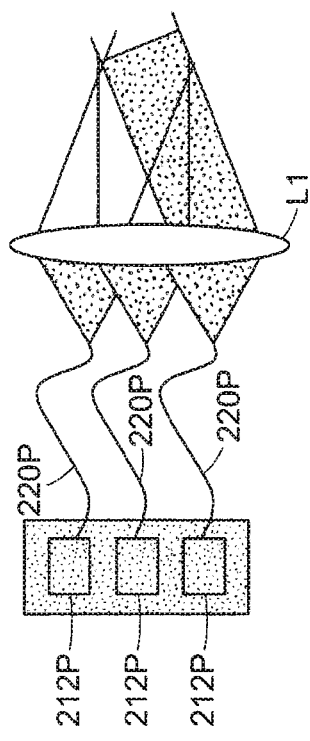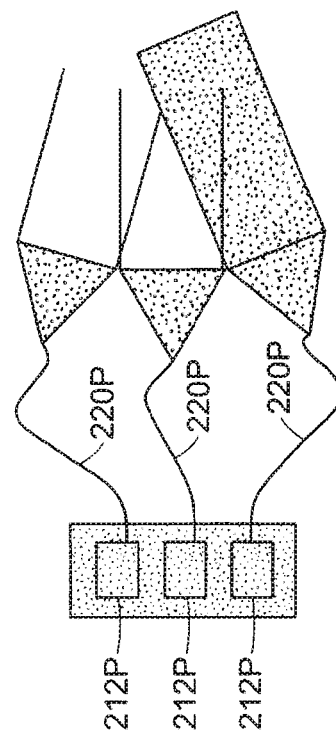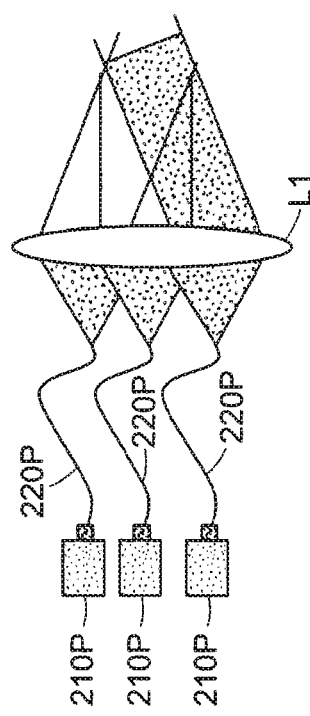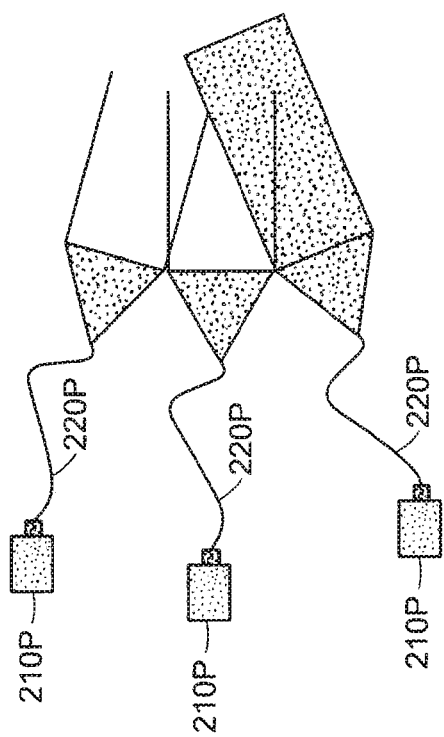

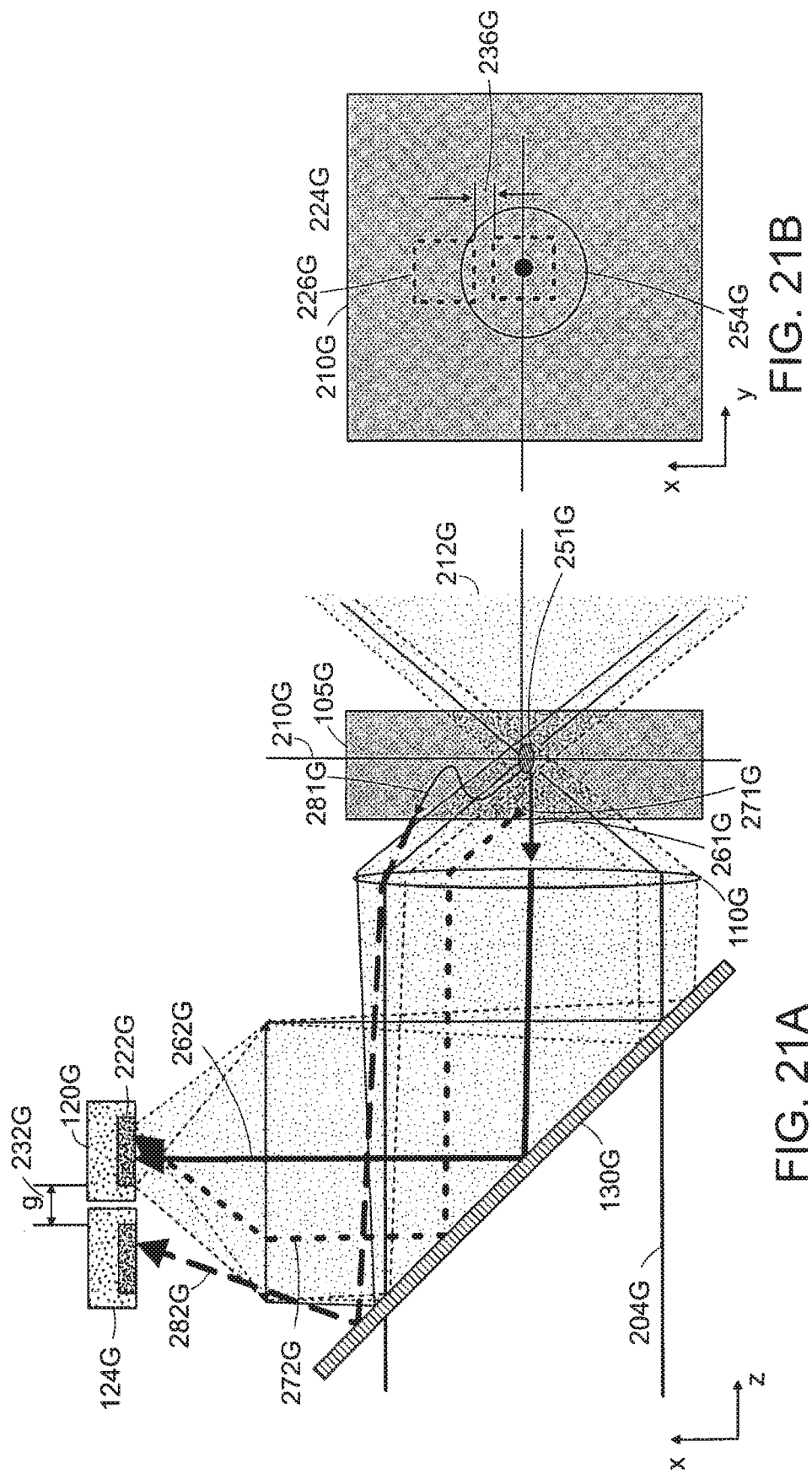

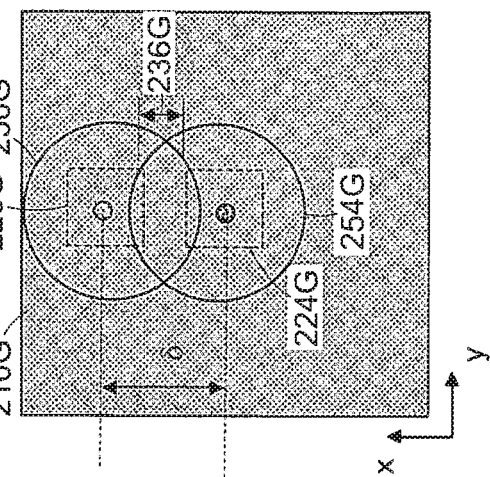
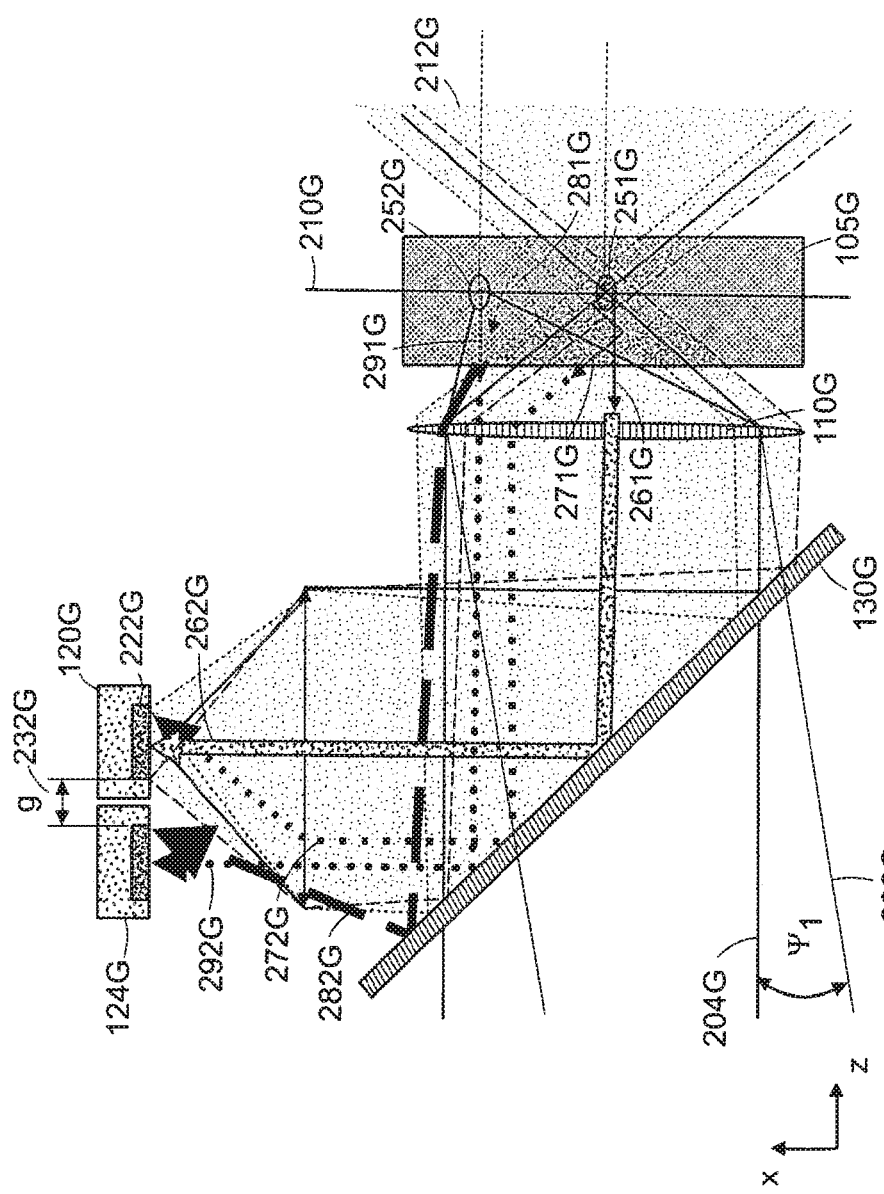
FIG. 22B
FIG. 22A

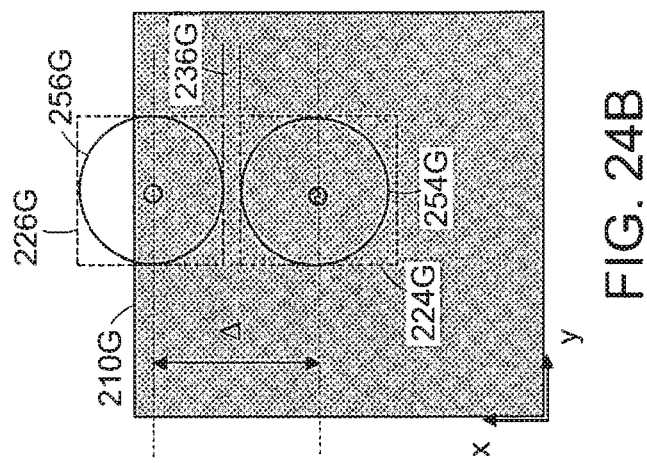
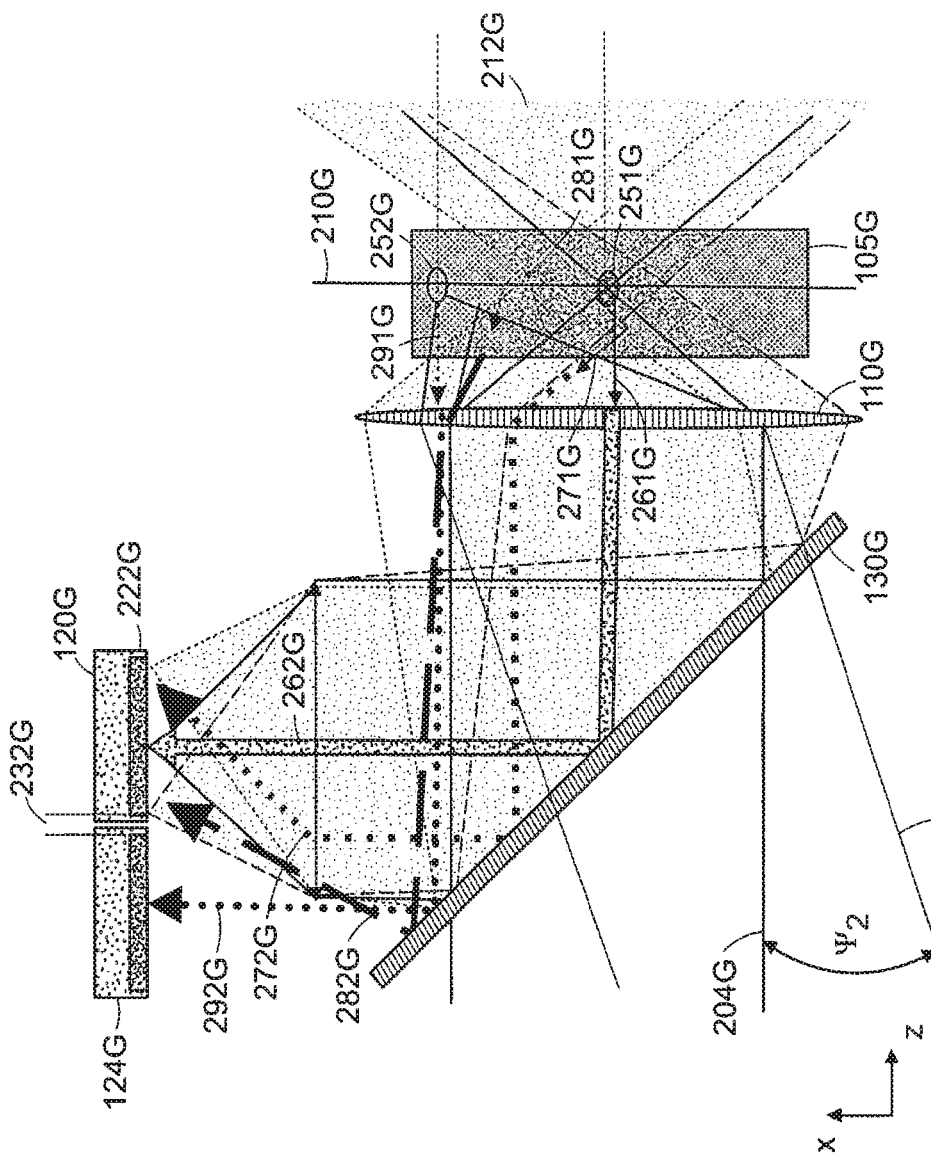
FIG. 24B
FIG. 24A

| Config. Name | | | | A | B |
|---|---|---|---|---|---|
| objective lens specs | manufacturer | | | Olympus | Olympus |
| | tube lens | | mm | 180 | 180 |
| | objective | | | XLUMPLFL 20X | XLUMPLFL 20X |
| | immersion | | | water | water |
| | magnification | Mag | # | 20 | 20 |
| | Numerical Aperture | NA | # | 0.95 | 0.95 |
| | back aperture diameter | A | mm | 17.1 | 17.1 |
| | working distance | WD | mm | 2 | 2 |
| | focal length | $f_o$ | mm | 9 | 9 |
| | field number | FN | mm | 22 | 22 |
| | corrected field | $F_c$ | mm | 1.1 | 1.1 |
| illumination path | | | | side   diagonal | side   diagonal |
| micro lens specs (square shaped) | aperture (=pitch) | p | mm | 1.06 | 1.9 |
| | focal lens | $f_m$ | mm | 17 | 25 |
| | # of lenses per side | # | | 8 | 8 |
| | diameter of all lenses | | mm | 8.48   11.99 | 15.2   21.50 |
| intermediate optics in illumination pathway | lens L1 (focal distance) | $f_c$ | mm | 50 | 40 |
| | diameter at lens L1 | $d_{L1}$ | mm | 10.5   14.9 | 16.3   23.1 |
| | diameter at scan mirror | $d_m$ | mm | 3.1   4.4 | 3.0   4.3 |
| | angle between beams | $\Omega_m$ | Rad | Deg | 0.02   1.21 | 0.05   2.72 |
| | mechanical scan angle ($\Omega_m/2$) | $\Omega_m/2$ | Rad | Deg | 0.01   0.61 | 0.02   1.36 |
| | lens L2 (focal distance) | $f_{L2}$ | mm | 30 | 30 |
| | diameter at lens L2 | $d_{L2}$ | mm | 8.5   12.0 | 14.6   20.7 |
| | lens L3 (focal distance) | $f_{L3}$ | mm | 125 | 125 |
| | diameter at lens L3 | $d_{L3}$ | mm | 19.6   27.8 | 25.5   36.0 |
| | diameter at objective | $d_o$ | mm | 13.0   18.4 | 12.7   17.9 |
| focal plane | distance between foci | D | micron | 46 | 103 |
| | field in optical plane | F | micron | 366   518 | 821   1161 |

| detection path | | | round diag. | round diag. |
|---|---|---|---|---|
| | objective back aperture | A mm | 17.1 | 17.1 |
| intermediate optics in detection pathway | diameter at lens L3 | $d_{L3}$ mm | 22.19 | 28.50 |
| | diameter at lens L2 | $d_{L2}$ mm | 18.08 | 24.40 |
| | detection mirror diameter | $d_m$ mm | 4.10 | 4.10 |
| | pitch of MAPMT's | mm | 2.2 | 2.2 |
| | lens L4 (focal distance) | mm | 103.77 | 46.32 |
| | diameter at lens L4 | mm | 21.70 | 21.70 |

FIG. 25E

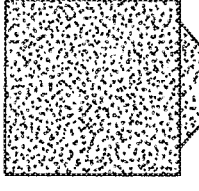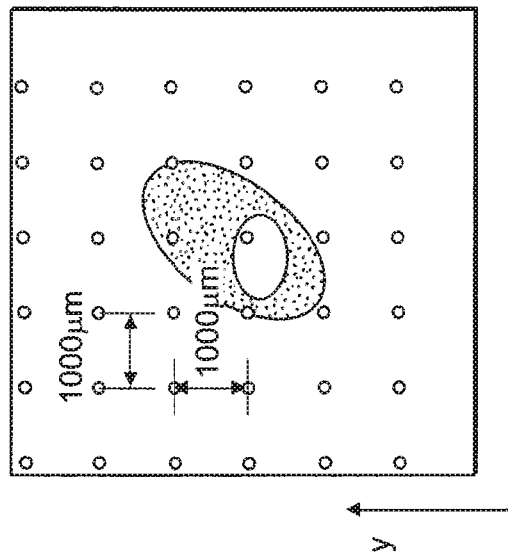
FIG. 26D
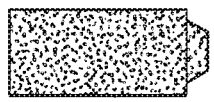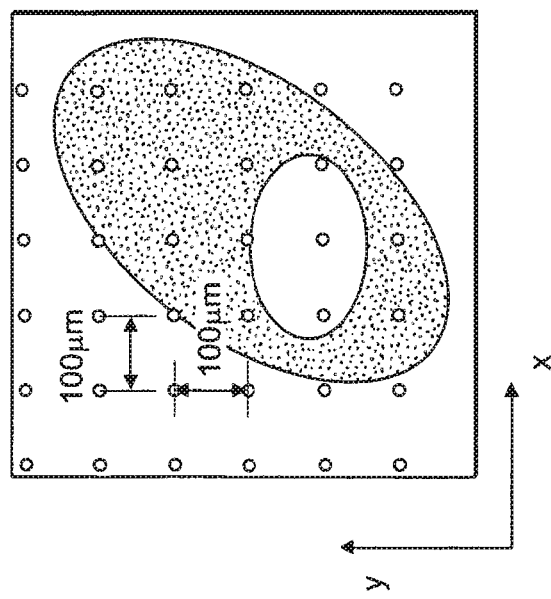
FIG. 26C

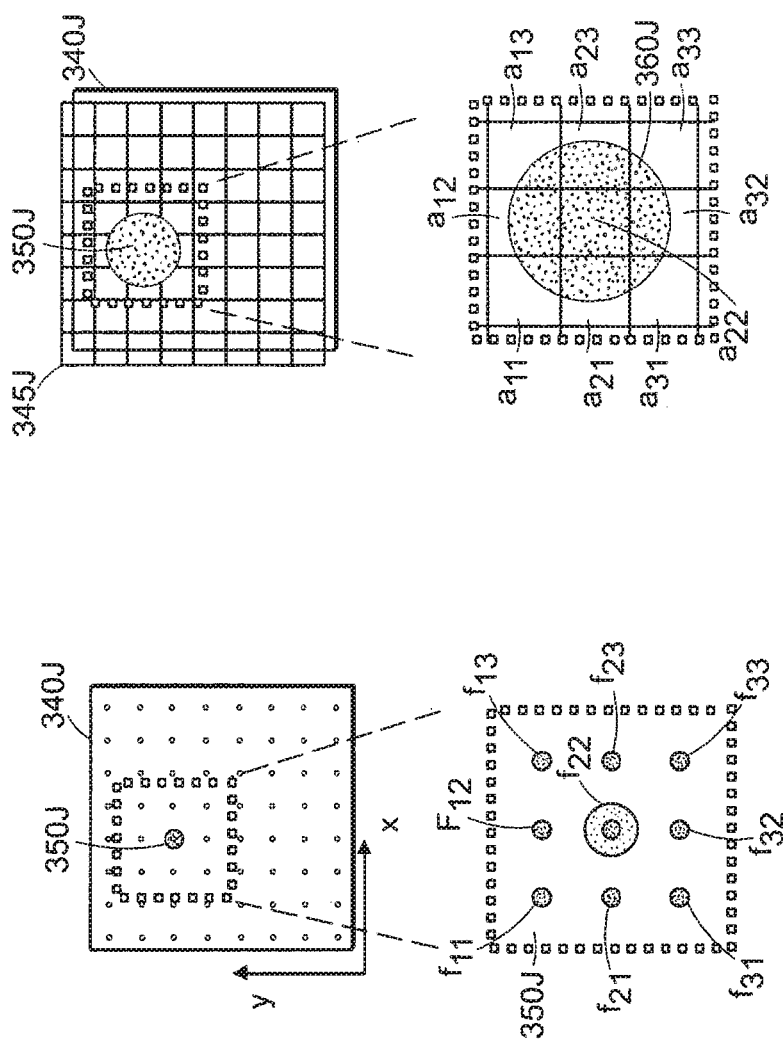

MULTIFOCAL IMAGING SYSTEMS AND METHOD

CROSS REFERENCE TO RELATED APPLICATIONS

This application is a continuation of U.S. patent application Ser. No. 11/442,702, filed May 25, 2006, which claims the priority of U.S. Provisional Application No. 60/684,608 filed May 25, 2005 entitled, MULTI FOCAL MULTIPHOTON IMAGING SYSTEMS AND METHODS, the whole of each of these applications being hereby incorporated by reference herein.

STATEMENT REGARDING FEDERALLY SPONSORED RESEARCH OR DEVELOPMENT

This invention was made with government support under grant numbers R33 CA84740 and R33 CA91354 awarded by the National Institutes of Health. The government has certain rights in this invention.

BACKGROUND OF THE INVENTION

Systems and methods for microscopic analysis of biological material have been used for characterization and diagnosis in many applications. Fluorescence microscopy, for example, has been used for optical analysis including the histological analysis of excised tissue specimens. Optical coherence tomography has been used for three dimensional imaging of tissue structures, however, the limited resolution of existing systems has constrained its use for definitive pathological analysis. Confocal microscopy has been used for high resolution imaging and has controllable depth of field but limited imaging speed.

Multiphoton microscopy is based on the nonlinear excitation of fluorophores in which fluorescence generation is localized at the focus of excitation light. Multiphoton microscopy is used for deep tissue imaging because of its subcellular three dimensional (3D) resolution, minimal phototoxicity, and tissue penetration depth of over a few hundred micrometers. It has become useful in biomedical studies such as neuronal plasticity, angiogenesis in solid tumors, transdermal drug delivery, and non-invasive optical biopsy, for example.

A practical limitation of multiphoton microscopy is its imaging speed which typically lies in a range of less than two frames per second. While this speed is sufficient in many cases, there remain applications in which can be enhanced by improvements in imaging speed. There is a continuing need for further improvements in microscopic analysis of biological materials for numerous applications.

SUMMARY OF THE INVENTION

The present invention relates to systems and methods for the multifocal imaging of biological materials. An optical system is provided in which a plurality of optical pathways are used in combination with focusing optics to provide a plurality of focal locations within a region of interest of a material being optically measured or imaged. The detector can comprise a plurality of detector elements which are correlated with the plurality of focal locations to provide for the efficient collection of light from the material being imaged. A preferred embodiment of the invention utilizes a scanning system that provides relative movement between the material and the focal locations to provide for fast imaging of the material.

In a preferred embodiment a light source, such as a laser, is used with a multifocal optical element to provide an array of spatially separated optical pathways. The multifocal optical element can comprise a micro lens array, a diffractive optical element, or a beam splitter device, for example, such that a plurality of beams are provided that can be focused onto a plurality of focal locations within a biological material to be imaged.

An important issue in the collection of light from discrete focal spots or locations within a turbid medium such as tissue is the cross talk that can occur due to the scattering of light. This cross talk can substantially limit the usefulness of the images of the tissue that are produced. By increasing the distance between adjacent focal spots such cross talk can be reduced or eliminated, however, this reduces the resolution of the resulting image or increases the time needed to scan the tissue. Thus it is desirable to employ focal spacing of at least 10 microns and preferably more than 25 microns.

In a preferred embodiment of the invention, high speed multiphoton microscopy can measure biological systems such as, for example, kinetic processes in the cytosol of a single cell, for example, or imaging a volume of tissue. For example, high speed 3D imaging can map 3D propagation of a calcium wave and the associated physical contraction wave through a myocyte, or the rolling of luckocytes within the blood vessel of a solid tumor. High speed 3D microscopy provides for sampling a statistically significant volume of biological specimens. Since the field of view of most microscopes is limited to about 100 microns on a side with an imaging depth of 100 microns, the measurement volume is limited to only $1 \times 10^{-3}$ mm$^3$. While this volume is sufficient for cellular imaging, many tissues have physiologically relevant structures ranging from the cellular level up to several millimeters in size. For example, a neuron with its extensive dendritic tree can span a volume over 1 mm$^3$ and many dermal structures such as hair follicles and sabestious glands can not be seen with images confined to an area of 100-200 micrometers. It is desirable, for example, to image a hierarchy of cardiac structures ranging from a single nucleus in a cardiac myocyte, to the distribution of muscle fibers and blood vessels, to the structure of chambers and heart valves with perfect registration across five orders of magnitude by imaging a whole mouse heart. Equally importantly, traditional 3D microscopes sample only tens to hundreds of cells and can never achieve comparable statistical accuracy and precision in many biomedical assays as techniques such as flow cytometry and image cytometry. High speed imaging can circumvent this difficulty by improving the number of cells or tissue volume to be sampled. By performing high speed multiphoton imaging, better quantitative measurements of transport pathways across the stratum corneum in transdermal drug delivery applications can be made, for example.

Systems and methods have been developed to enhance multiphoton imaging speed. A first method increases the scanning speed by using a high-speed scanner such as a polygonal mirror scanner or a resonant mirror scanner instead of a galvanometer-driven mirror scanner. This achieves an increase of scanning speed of more than 10 frames per second in the imaging of typical tissue specimens. In general, the system can operate at frequencies in a range of 1 to 500 Hz. This method can be used for turbid tissue imaging since it is not sensitive to the scattering of emission photons. A second method increases the imaging speed by parallelizing the multiphoton imaging process. It scans a sample with a multiple of excitation foci instead of forming only a single focus. These foci are raster scanned across the specimen in parallel where each focus needs to cover a smaller area. The emission photons from these foci are collected simultaneously with a spatially resolved detector. One advantage of this method is that the imaging speed is increased by the number of excitation foci generated, without increasing the power of excitation light per each focus. High speed scanning systems needs higher power to compensate for the signal reduction per pixel due to the decrease of pixel dwell time. Images can be obtained by selecting the depth of focus to be positioned in a plane within the tissue or sample at a depth in a range of 10 microns to 500 microns.

In another embodiment, fiber optics can be used to couple the light source to the microlens array or other beam splitting element. The system can be implemented as a handheld optical probe for the diagnosis of dermal, cervical or colorectal cancer, for example.

The brain is an inherently three dimensional organ composed of many subregions. Accurate segmentation of brain morphology of small mammals is currently challenged by the lack of techniques which can sample the brain at high resolution over a large volume. The current method of choice, serial section reconstruction, is laborious, time consuming, and error prone. The device and methods described herein can quickly image brains or thick tissue sections of brains in 3D at sufficient resolution and over a large enough volume to provide 3D images suitable for classification of brain morphology and biochemical composition. The brain can be further stained by dyes, such as nuclear dyes DAPI or Hoescht, either through intravital injection, transgenic expression, or ex vivo methods, to facilitate classification of regions. Automatic segmentation routines can also be used to improve the classification and automate portions of the process.

Accurate measurement of vasculature is important to characterize many biomedical for vasculature related diseases. For instance, proangiogenesis therapies are useful in such areas as tissue engineering, wound healing, bone fractures and coronary heart disease. Anti-angiongenesis treatments are important in processes as cancer, blindness, and rheumatoid arthritis. Unfortunately traditional histopathological analysis of tissue sections is wholly inadequate to characterize the vasculature of a tissue or organ as blood vessels form complex, multiscale 3D networks, with feature spanning from the submicron to centimeter scale. The device and methods described in the patent are capable of acquiring high quality 3D datasets over 3D tissue and organ samples suitable for characterization of the vasculature of the tissue. To aid visualization of the vasculature, the tissue can be stained by contrast agents which bind to the epithelial wall of the blood vessels, or fill the interior of vessels. Automatic segmentation routines can also be used to improve the classification and automate portions of the process.

A large percentage of deaths are due to metastasis. Unfortunately, the migration of cancer cells from the primary tumor to secondary sites is a multi-step process which is not well understood. Standard histopathological analysis is ill-suited to study metastasis and suffers from a number of limitations. First, it is extremely difficult to find rare metastatic cancer within a 3D bulk tissue using traditional 2D histopathology. In many instances traditional 2D histopathology is unable to find evidence of the presence of metastatic cancer cells in an organ of animal. However, it is known that many subjects eventually develop tumors at a later time. It is clear that traditional histopathology cannot effectively detect rare cells. Another limitation is that the present histopathology methods provide limited information about the 3D spatial arrangement of cancer cells with the 3D vasculature of the organ. It is known that one of the critical steps in metastasis is extravasation into the surrounding stroma from the vasculature so it is essential to be able to visualize this spatial relationship between cancer cell and the endothelial blood vessel wall. Preferred embodiments of the present invention are capable of acquiring high quality 3D datasets over 3D tissue and organ samples suitable for characterization of the metastases. To aid visualization of the metastases, the cancer cell can be stained by dyes or labeled with proteins such as OFP. Automatic segmentation routines can also be used to improve the classification and automate the localization of the cancer cells and tumors.

In order to understand the effects of a drug on an organism, analysis at the tissue, whole organ, and whole organism level is vitally important. ADME, efficacy and toxicology effects are known to have strong spatial variations on the morphological, cellular and biochemical state of a tissue. Even within a specific tissue type, the response can be nonuniform due to variations in the transport and distribution of a drug throughout tissue, epigenetic expression, and cellular activity. The devices and methods described herein can be used to provide morphological, biochemical and spectroscopic information about the state of a tissue across multiple length scales, from subcellular, whole tissue, whole organ and even entire organism, in response to the treatment of a molecular agent. Efficacy, ADME, and toxicology information can be derived which provides a fuller and more accurate description to predict the actual effect of drug candidate at the organism level.

DESCRIPTION OF THE DRAWINGS

FIGS. 2a-2c are images of human skin acquired with the present invention including the stratum corneum layer, stratum granular and the basal layer, respectively.

FIGS. 10(a)-(i) illustrates close up views of the 3D focal region generated by the setup in fig. W-10 and views of the 3D scanning: (a) the focal region; (b) an array of excitation light beams; (c) x/y view at first depth; (d) x/y view at second depth; (e) x/z view; (f) multiple rows of excitation foci lie in different focal planes and are all shown in this xy view; (g) xz view of the rows shown in (f); (h) x/y view of the x/y scanning configuration covering the x-y-z image (as in (f) all foci are shown, even though they lie in different planes and in the lower part of the images even behind each other; and (i) a view in the yz plane illustrating scan progression.

FIGS. 14(a)-(d) illustrate preferred embodiments for providing illumination beam paths in accordance with the invention.

FIGS. 15(a)-(d) illustrated further preferred embodiments for detecting light from different focal locations in accordance with preferred embodiments of the invention.

FIGS. 21(a) and (b) illustrates scattered light detection with two PMTs and one excitation foci according to an embodiment of the invention.

FIGS. 22(a) and (d) illustrates scattered light detection with two PMT's and two excitation foci according to an embodiment of the invention.

FIGS. 24(a) and (b) illustrates reducing optical cross talk according to an embodiment of the invention by increasing the distance between the excitation foci and increasing the area of the detection elements.

FIGS. 25(a)-(e) illustrate in tabular form two alternative embodiments A and B of the invention in terms of changing optical setup.

FIGS. 26(c)-(d) illustrate an objective lens with large field of view enables large separation of foci and thus enables low optical cross reduction FIGS. 27(a) and (b) illustrate data post-processing sequences.

FIGS. 29(a)-(c) illustrate a linear deconvolution process.

DETAILED DESCRIPTION OF THE INVENTION

Figure 1:
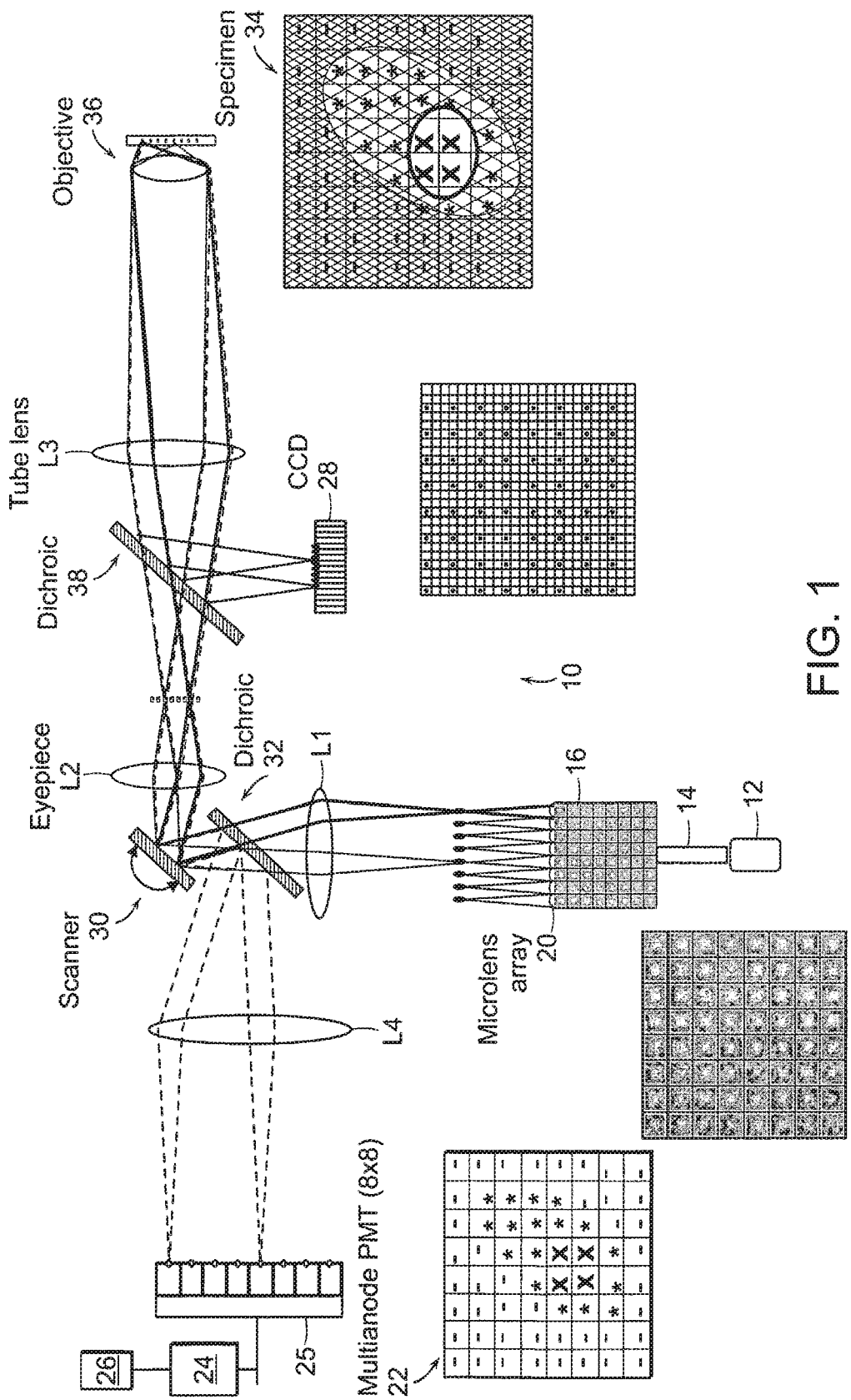
FIG. 1 is a schematic diagram of an imaging system in accordance with a preferred embodiment of the invention.
Figure 3:
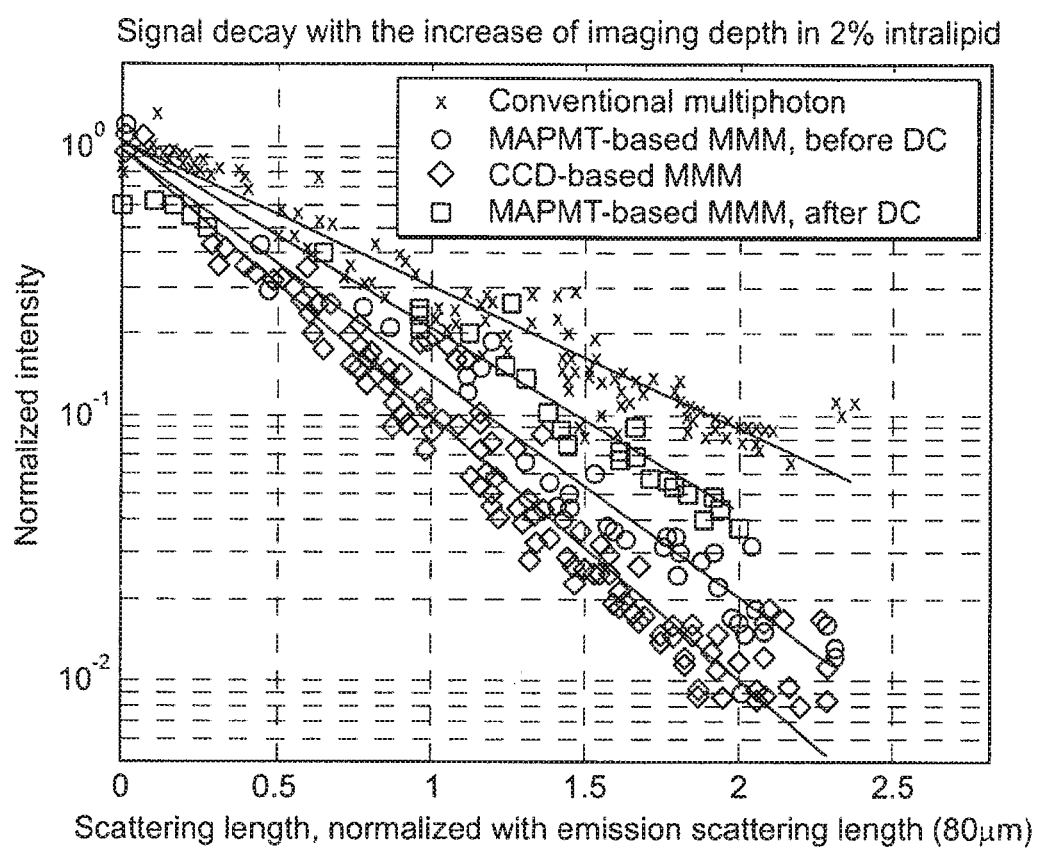
FIG. 3 graphically illustrates the signal decay with increasing imaging depth of conventional systems and those incorporating the present invention.

As the input power of excitation light increases, the signal is increased proportionally to the square of input power, $S(t) \propto [P(t)]^2$. However, there is a limitation in input power level due to finite lifetimes of fluorophores.

In the multiphoton excitation of fluorophores with a pulsed laser, the fluorophores, which are excited with the last pulse, stay in the excitation state for a few nano-seconds (depending on the fluorophore). Some excited fluorophores may not be excited again with the next pulse of excitation light (12 ns later in case of the laser having 80 MHz pulse repetition rate). Therefore, signal level becomes saturated with a higher input power than the limited input power level. The limitation on the input power level is related to the excitation probability of a single fluorophore with a single pulse, $P_{pulse}$. It is formulated in the following expression with the condition that excitation light is focused with an objective into a fluorophore of an absorption coefficient ($\delta_a$).

$$P_{pulse} = \delta_a \left[ \frac{\lambda}{K_a hc} \right]^2 \frac{NA^4}{\tau_p f_p^2} [P_o(t)]^2 \quad (1)$$

The nominal conditions are that the excitation light has the wavelength ($\lambda$=800 nm), the pulse width ($\tau_p$ =200 fs), the pulse repetition rate ($f_p$=80 MHz), and the average power, $P_o(t)$. The numerical aperture (NA) of the lens objective is 1, (NA=1). The fluorophore has the absorption coefficient, ($\delta_a$=10 GM), where 1 GM is $10^{-50}$ cm$^4$×s/photon. In order to avoid the saturation, $P_{pulse}$ must be less than 0.1 in general ($P_{pulse}$<0.1). With these conditions, the input power ($P_o(t)$, with which $P_{pulse}$ becomes close to the saturation limit, is approximately 6 mW, ($P_o^{sat}(t) \cong 6$ mW) in this example. In case the concentration of the fluorophores is 10 μM, the number of emission photons collected per second is approximately 3×10$^7$ photons/s with the assumption that the collection efficiency of emission photons is approximately 0.01 ($\varepsilon_{col}$=0.01). Assuming that each pixel needs 300 photons and each image comprises of 256×256 pixels, the frame rate that can be achieved with the input power under the saturation limit is 1.5 frames/s. Although the higher frame rate is achieved with specimens of higher fluorophore concentration, it is clear that there is a limitation in input power level due to fluorophore saturation.

MMM increases the frame rate by scanning with multiple excitation foci. Therefore, MMM can achieve the higher frame rate, while the input power for each excitation focus is kept below the saturation limit. For example, the MMM system, which scans with an 8×8 array of excitation foci, can achieve the frame rate of 96 frames/s (=1.5 frames/s×64 foci). In a preferred embodiment it is desirable to collect at least 15 frames per second and preferably 30 frames per second or more. One practical limitation in MMM is that more input power is required to generate multiple excitation foci. The power requirement to generate 64 foci is 384 mW (=64 foci×6 mW per each focus). Since available laser sources can output approximately 2 W of power, enough power is available for MMM.

The limit of optical imaging depth in tissues is limited by photon interaction with tissue constituents. Photon scattering is a dominant factor in multiphoton microscopy whereas the effect of photon absorption is relatively negligible. Scattering of excitation photons reduces the amount of fluorescence generated at its focus, because less excitation photons reach the focal volume. The emission photons from the focus are also scattered so that they may not be collected by the optics in the detection path or spatially dispersed in the imaging plane where detectors are positioned. Since the excitation light has a longer wavelength than the emission light, the excitation light typically experiences less scattering than emission light. The effect of photon scattering is expressed by the mean free path length of scattering, P which is the depth constant in exponential decay of unscattered photons, $S(z) \propto \exp(-z/l^s)$.

Intralipid emulsion can be used as a tissue phantom with similar optical properties as tissue. The optical properties of 2% intralipid are mean free path length at excitation wavelength (780 nm) of 167 μm, ($l_{ex}^s \cong 167$ μm) and at emission wavelength (515 nm) of 62.5 μm, ($l_{em}^s \cong 65$ μm). Since it is known that only ballistic excitation photons contribute multiphoton excitation in the depth of a few times of scattering length, the amount of multiphoton excitation decays with the mean free path length of 84 μm (=167 μm/2) with the consideration that two-photon excitation is a quadratic process. Conventional multiphoton microscopy is based on the scanning of a single excitation focus and the signal is collected using a detector without spatial resolution such as a conventional photomultiplier tube (PMT). The PMT has a large detection area and can collect most of the signal generated at the excitation focus including a large fraction of the scattered photons. Therefore, conventional multiphoton microscopy is relatively immune to the scattering of emission photons by the tissue. However, for an MMM system that utilizes a CCD detector to distinguish the signals originated from each of the foci, the scattering of emission photons seriously degrades the SNR of the instrument for deep tissue imaging. The CCD camera has relatively slow readout speed and typically integrates all the emission photons during the acquisition of each frame. Because a CCD camera contains pixels in which each pixel covers a 0.1 μm² region in the specimen plane, scattered emission photons deflected from their original paths are not collected in the correct pixel but are distributed broadly across the imaging plane. The distribution of scattered emission photons is very broad with its FWHM of 40 μm in the depth of 233 $l_{em}^s$. These scattered photons result in a degradation of image SNR by more than one order of magnitude when imaging depth is over 2×$l_{em}^s$, compared with conventional multiphoton microscopy.

The major limitation of CCD-based MMM system lies in its small pixel area. For conventional wide field imaging, a large number of CCD pixels are needed to maintain good resolution while covering a good size field of view. A 100 □m size image will require about $10^7$ pixels to be imaged at full optical resolution (300 nm). The situation is very different for MMM imaging. Since a femtosecond light source can only provide at maximum 2-4 watts of optical power and typically about 50-100 mW are required at each focus to generate an efficient muliphoton excitation process for deep tissue imaging. An MMM system can realistically and effectively scan about 20-40 foci in parallel with tissue specimens. Since these foci are raster scanned across the specimen, the image resolution is determined by the excitation point spread function (PSF) of the light and is not sensitive to the detector pixelation. In particular, a preferred embodiment uses an MMM system having photon detectors containing only as many elements as the number of excitation foci. The need for fewer elements allows the use of a detector with a significantly larger pixel area while maintaining a reasonable device size. A multi-anode PMT (MAPMT) is a preferred detector for this purpose.

A preferred embodiment of the present invention uses an MAPMT instead of the CCD camera for the signal collection from multiple foci. The MAPMT is similar to conventional PMTs with a good quantum efficiency (over 20% in the blue/green spectral range), negligible read noise and minimal dark noise with cooling. MAPMT has a cathode and dynode chain with a geometry that ensures that the spatial distribution of photons on the cathode is reproduced accurately as electrons distribution at the anode. The anode of the multi-anode PMT is divided rectilinearly into its elements providing spatial resolution for the simultaneous collection of signals from multiple locations. In one example, a MAPMT, which has an array of 8×8 pixels (H7546, Hamamatsu, Bridgewater, N.J.) is used. Note that a flat panel detector having a pixel area of sufficient size can also be used. For example, a binnable CMOS or CCD imaging sensor can be operated to read out binned images at comparable frame rates with an effective pixel size corresponding to that of a MAPMT.

A preferred embodiment of the invention uses the imaging systems as described herein in conjunction with a system for sectioning a sample such as a tissue sample that is described in greater detail in U.S. patent application Ser. No. 10/642, 447, by So, et al. filed Aug. 15, 2003, the entire contents of which is incorporated herein by reference.

The schematic of a preferred embodiment of the imaging system 10 in accordance with the invention is shown in FIG. 1. The light source 12 used is a Ti-Sapphire (Ti-Sa) laser (Tsunami, Spectra-Physics, Mountain View, Calif.) pumped by a continuous wave, diode-pumped, frequency-doubled Nd:YVO$_4$ laser (Millenia, Spectra-Physics, Mountain View, Calif.). It generates approximately 2 W at 800 nm wavelength which is sufficient for most MMM applications. The excitation beam from the laser is optically coupled using optical fiber 14 or free space lens system to a beam expander 16 and then illuminates a microlens array 20 (1000-17-S-A, Adaptive Optics, Cambridge, Mass.) which, in this example, is an array of 12×12 (or 8×8) square microlenses that are 1 mm×1 mm in size and 17 mm in focal length. The degree of beam expansion can be selected such that an array of 8×8 beam-lets is produced after the microlens array. The beamlets are collimated after lens L1 and reflected onto an x-y scanner mirror 30 (6220, Cambridge Technology, Cambridge Mass.) which is positioned in the focal plane of lens L1. In this configuration, the beam-lets overlap each other on the scanner mirror surface and are reflected similarly by the rotation of the scanner mirror. After the scanner, the beam-lets enter a coupling lens system such as a microscope (BX51, Olympus, Melville, N.Y.) via a modified side port. A combination of lenses L2 and L3 expands the beam-lets to fill the back aperture of the objective lens 36 in order to use the full NA of the objective lens. The scanning mirror is in the telecentric plane of the back aperture of an objective lens so that the beamlets are stationary on its back aperture independent of the motion of the scanner mirror. The objective lens generates the 8×8 focus array of excitation light in the sample plane in the specimen 34. The scanner mirror moves the array of excitation foci in the sample plane in a raster pattern to cover the whole sample plane. Alternatively, a digital micromirror (MEMS) device can be used to control beam scanning in the sample plane. A beamsplitter can also be used to split an input beam before the microlens array. Another alternative embodiment employs a diffractive optical element in conjunction with a beam splitter. The objective used in this system is a 20×water immersion lens with 0.95 NA (XLUMPLFL20XW, Olympus, Melville, N.Y.). The excitation foci are separated from each other by 45 µm in this example so that the scanning area of each focus is 45 µm×45 µm. The frame size is 360 µm×360 µm by scanning with the array of 8×8 foci. The frame rate to generate images of 320×320 pixels becomes approximately 19 frames per second with the pixel dwell time of 33 µs.

Emission photons are generated at the array of excitation foci in the specimen and are collected by the same objective lens forming an array of emission beam-lets. In case of a CCD-based MMM, the emission beam-lets are reflected on a long-pass dichroic mirror 38 (650dcxxr, Chroma Technology, Brattleboro, Vt.) and get focused in optional CCD camera 28 (PentaMax, Princeton Instruments, Trenton, N.J.) with a lens (L3). The CCD camera integrates emission photons during the scanning time of each frame to generate images. In case of a preferred embodiment using an (without the CCD) MAPMT, the emission beam-lets travel back to the scanner mirror 30 retracing the excitation paths. The emission beam-lets are reflected by the scanner mirror. The emission beam-lets are de-scanned and their propagation directions remain stationary irrespective of the movement of the scanner. The emission beam-lets are reflected by a long-pass dichroic mirror 32 (650dcxxr, Chroma Technology, Brattleboro, Vt.) and are focused after lens (L4). A short-pass filter (E700SP, Chroma Technology, Brattleboro, Vt.) blocks any strayed excitation light. The focused emission beam-lets are collected at the center of corresponding channels of a MAPMT 22 (H7546, Hamamatsu, Bridgewater, N.J.). The emission photons coming from the array of excitation foci are collected by the MAPMT. An image is formed by the temporal encoding of the integrated signal with the known raster scanning pattern using image processor or computer 24 and is electronically stored in memory and/or displayed using display 26.

The pair of L2 and L4 lenses magnifies the array of emission foci so that individual emission beamlets are focused at the center of corresponding elements of the MAPMT. Further, since the emission beam-lets are descanned, they remain stationary. Since the emission beam-lets have to go through more optical elements, loss of emission photons occurs. The transmission efficiency is approximately 0.7. The signals from the MAPMT are collected by a stack of four multi-channel photon counter card (mCPhC) which has 64 channels for simultaneous signal collection. Each mCPhC has 18 channels of photon counter circuits and can be housed 25 with a digital interface to the computer 24. The mCPhC expandable so that 64 channels are readily implemented by using 4 cards in parallel. The mCPhC has a 32-bit parallel interface with a computer for high-speed data transfer. Currently, the speed is limited by the speed of the computer PCI bus. Transfer rate can be more than one hundred frames (320×320 pixels, 16 bit images) per second.

Since the scattered emission photons have the spatial distribution of 40 µm as its FWHM at the imaging depth of $2 \times l_{em}^s$, the sensitivity of the microscope is partly determined by the effective detector area, the area in the sample plane from which a detector collects emission photons. Since microscopes are telecentric systems, the effective detector area is linearly related with the detector size in the image plane. With a magnification, M, and a linear dimension of detector, $L_D$, the linear dimension of effective detector area ($L_E$) is $L_E=L_D/M$. In general, the larger the effective detector area, the more effective the detector can collect scattered emission photons. In the case of using a 20 × magnification objective, a 10 mm diameter standard PMT has an effective detector area of 500 µm diameter that is significantly larger than the width of the scattered emission photon distribution. Therefore, standard PMTs have good collection efficiency of scattered emission photons and allow very effective deep tissue imaging. In the case of a spatially resolved detector, each pixel can be treated as an individual detection element. For a CCD camera with 20 µm×20 µm pixels, each pixel has an effective detector area of 1 µm×1 µm for 20 × magnification. Therefore, the CCD-based MMM system cannot utilize these scattered emission photons which are distributed uniformly throughout the image contributing to the background noise. In this example of the MAPMT-based MMM system, the effective detector area of each channel is 45 µm×45 µm. Therefore, the MAPMT can collect significantly more scattered emission photons into the correct channels than the CCD camera, because its effective detector area, or detector element collection area, is comparable with, or corresponds to, the width of the scattered photon distribution from each focal area (45 microns×45 microns).

MAPMT-based MMM system can be easily converted to the conventional multiphoton microscope which is based on single-focus scanning and signal collection with PMTs. In the set up of conventional multiphoton microscope, the excitation beam is not expanded and goes directly onto the scanner without the combination of the microlens array and lens Li. The rest of excitation beam path is the same as MAPMT-based MMM. Specimens are scanned with a single excitation focus. The emission light collected by the objective lens is reflected on a dichroic mirror. The reflected emission beam shrinks with a pair of lenses and is collected by a detector (PMT). An image is formed by the temporal encoding of the integrated signal with the known raster scanning pattern.

CCD-based MMM have limitations for turbid tissue imaging by measuring the effect of emission photon scattering on PSF (scattering function). Scattered emission photons form additional intensity distribution around the PSF constructed with ballistic unscattered photons. Their intensity distribution is quite wide with its FWHM of 40 µm at the imaging depth of $2 \times l_{em}^s$. FWHM of the total PSF (including the intensity distribution due to scattered emission photons) is not changed due to scattering up to such depth because the wide distribution of scattered emission photons does not contribute to FWHM. In terms of contrast, signal decay in CCD-based MMM with the increase of imaging depth is higher than that of SMM by an order of magnitude at $2 \times l_{em}^s$. Also the wide distribution of scattered emission photons contributes as noise and causes loss of contrast by another order of magnitude at the depth.

Imaging dermal structure based on autofluorescence has been performed using the system of the present invention. Endogenous fluorophores have low quantum yield and low extinction coefficients compared with typical exogenous fluorescent labels. The dermal structure imaged using a preferred embodiment of the present invention has a layered structure with significantly different indices of refraction resulting in significant spherical aberration. Multiphoton imaging of dermal structures without photodamage has a pixel rate of 15 KHz with 15 mW input power. In this example an input power of 7 mW per focus at the specimen with the excitation wavelength set at 800 nm. The objective used is 20×water immersion with 0.95 NA (XLUMPLFL20XW, Olympus, Melville, N.Y.). With a frame rate of 2.5 fps for a 320×320 pixel image (4 KHz pixel rate) this is 10 times faster than the previous systems. The epidermis is imaged down to the basal cell layer using this MAPMT-based MMM. Representative layers from the stratum corneum, stratum granular, and the basal layer are shown in FIGS. 2a-2c. The signal from these layers are mostly due to the fluorescence of NAD(P)H inside the cell. Thus an MAPMT-based MMM has equivalent or improved sensitivity as conventional multiphoton microscopy but with significantly increased imaging speed. The intensity of the image is not uniform: the intensity is high in the center and becomes dim in the corner of the image. This is because the intensity of the excitation beam has Gaussian spatial distribution so that the beamlets made from center part of the expanded beam have higher intensity than the peripheral portions of the beam. A beam splitter, serial dichroic mirrors or a top hat holographic filter can be used to provide a more uniform array of beams delivered to the individual focal positions.

Figure 5:
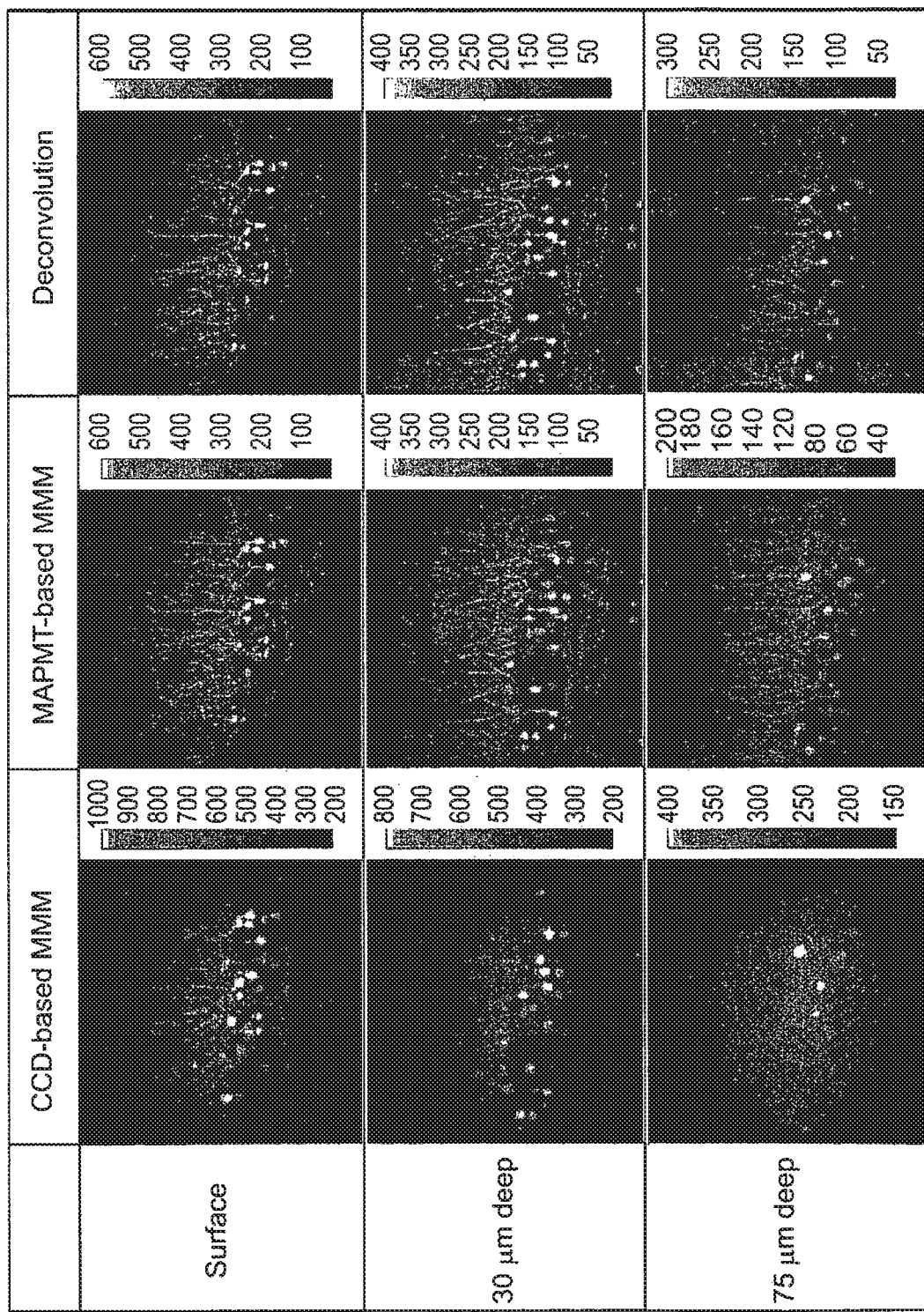
FIG. 5 illustrates images based on CCD, MAPMT and deconvolution thereof at the surface and at different depths of brain tissue.

Using both CCD and MAPMT detectors in MMM geometry, the signal decay can be measured as a function of scattering length. As the imaging depth increases, the signal is decreased due to scattering of both excitation photons and emission photons. The signal decay is measured by imaging 4 μm diameter fluorescent latex microspheres (F8858, Molecular Probes, Eugene, Oreg.) immobilized in 3D by 2% argarose gel (UltraPure Low Melting Point Argarose, Invitrogen, Carlsbad, Calif.). Intralipid emulsion (Liposyn III, Abbott Laboratories, North Chicago, Ill.) is added to the sample as a scatterer in various concentrations of 0.5 to 2%. Intralipid emulsion of 2% volume concentration is known to have similar scattering properties to those of tissues: mean free path length ($l^s$) of scattering is 80 μm, 168 μm at the wavelength of emission (605 nm), excitation (800 nm) respectively. The scattering properties of these intralipid solutions are verified by diffusive wave measurements. Peak intensity of the sphere image is a signal in the measurement and the decay of peak intensity as a function of the imaging depth is measured at each concentration. The signal decay can also be measured with a conventional multiphoton microscope as a reference. Signal decays in the three systems are measured down to a depth of 180 μm which is equivalent to $2.25 \times l_{em}^s$ (FIG. 5). The signal decay is expressed an exponential function, $S(z)=\exp(-cz/l_{em}^s)$. The decay coefficient, c is 1.22, 1.87, 2.30 in case of the conventional multiphoton microscopy, MAPMT-based MMM, and CCD-based MMM respectively. The decay rate from the conventional multiphoton microscope is the lowest as expected. The decay is the combinational effect of both excitation and emission photon scattering. Since the effect of excitation photon scattering is the same, the difference in decay coefficient is due to the effect of emission photon scattering. The decay coefficient, c from MAPMT-based MMM (1.87) is lower than the one from CCD-based MMM (2.30). However, the one from MAPMT-based MMM is still higher than the one from the conventional multiphoton microscope. It indicates that the spatial distribution of scattered emission photons is wider than the effective detector area of the MAPMT (45 μm×45 μm) so that some portion of the scattered emission photons are collected in the neighboring channels. The ratio of intensity sum collected in the neighboring pixels of the MAPMT to the intensity in the correct pixel was approximately 2 at the depth of $2 \times l_{em}^s$.

Although a significant portion of the scattered emission photons are still distributed outside the correct pixels in MAPMT-based MMM, these photons can be effectively restored to the correct pixels based on post-acquisition image processing. Note that the photons acquired at each pixel are temporally encoded and are organized to form an image based on the known scanner position as a function of time. This is exactly how images are formed in a conventional multiphoton or confocal microscope. A primary image is formed by photons acquired at the correct pixels corresponding to the fluorophore distribution in that portion of specimen. Note that the scattered photons in the neighboring pixels are also similarly temporally encoded. Therefore, secondary "ghost" images are formed in the areas of the image covered by the neighboring pixels. As an example, FIG. 4a is an image of spheres at 150 μm deep from the surface in 2% intralipid emulsion. The fact that the primary image at one pixel is "copied" into neighboring pixel, the spatial distribution of the scattered photons provides information for the reassignment of these scattered photons back to the correct pixel. Note that this temporally encoded information is not available in a CCD-based MMM system where the temporal information is lost during the integration process of the CCD. The effect of emission photon scattering on imaging can be described as follows. Generally, an image is formed as a convolution of source pixels and an emission point spread function ($PSF_{em}$). In the set up of MAPMT-based MMM, the array of 8×8 pixels is collected together each time so that the vector of pixels are acquired together, $\{S_{acq}\}$ (64×1) which is the product of convolution matrix, $[C]$ (64×64) and the source pixels, $\{S_s\}$ (64×1), $\{S_{acq}\}=[C]\times\{S_s\}$. The convolution matrix, $[C]$ is constructed based on the simplified $PSF_{em}$, $EPSF_{em}$ in which $PSF_{em}$ is spatially integrated over the effective detector area of the individual pixels of the MAPMT. Since $EPSF_{em}$ has a very coarse spatial resolution of 45 μm with the spatial integration, deconvolution with $EPSF_{em}$ becomes simple and is less sensitive to noise. The study of emission photon scattering on $PSF_{em}$ shows that the scattered emission photons form additional intensity distribution around the $PSF_{em}$, which is formed with ballistic unscattered emission photons. Its distribution is broad with its FWHM of 40 μm range in the imaging depth of 2×l7. The change of $PSF_{em}$ due to scattering (FIG. 4c) affects $EPSF_{em}$ by increasing intensity in the neighboring pixel areas (FIG. 4d). In the process of deconvolution, $EPSF_{em}$ is roughly estimated by measuring the intensity ratio of the real image to the ghost images as a function of imaging depth. The convolution matrix, $[C]_{esl}$ is constructed based on the estimated $EPSF_{em}$. The source pixel vector, $\{S_s\}_{esl}$ is acquired by the product of the inverse transform of $[C]_{esl}$ and the acquired pixel vector, $\{S_{acq}\}$.

$$\{Shd\ s\}_{esl}=[C]_{esl}\times\{S_{acq}\} \quad (2)$$

Figure 4B:
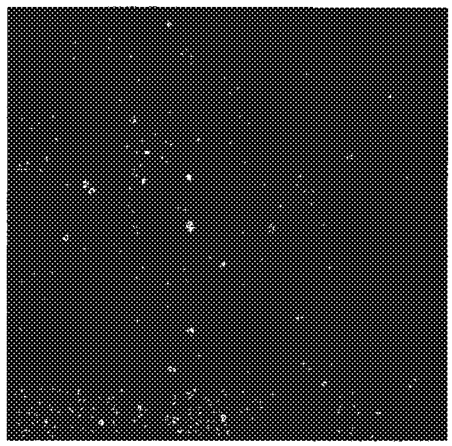
FIGS. 4a-4d include images before and after deconvolution as well as graphical illustration of scattering and crosstalk.
Figure 4A:
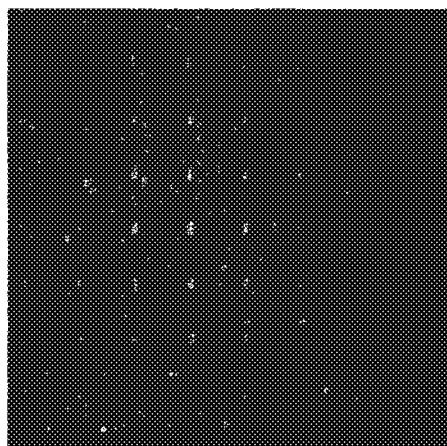
Figure 4D:
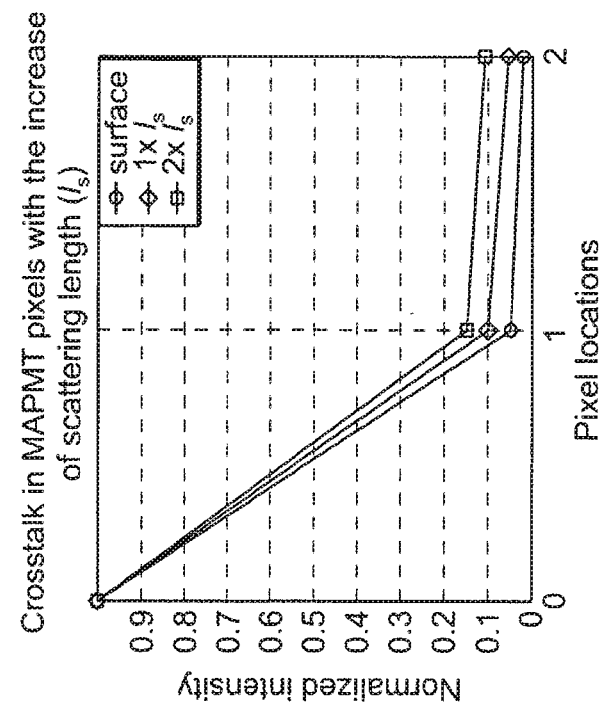
Figure 4C:
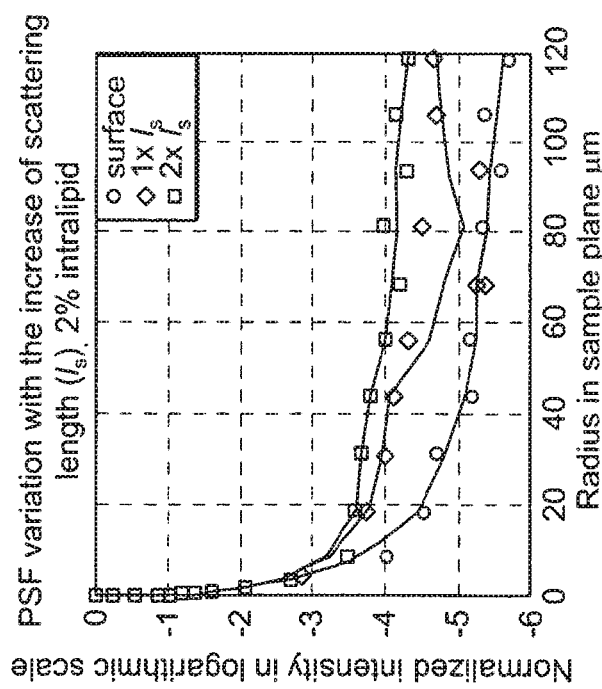

The restored image is presented in FIG. 4(b). The signal decay of a depth sequence of restored images is measured and the decay coefficient, c is significantly reduced to 1.58 after the deconvolution algorithm because the scattered emission photon can now be corrected and reassigned. The ghost images are almost completely eliminated as a result. Restoration algorithms can be further refined such as by adding maximum likelihood estimation to minimize image structural overlap between neighboring pixels. This simple deconvolution approach improves very effectively the performance of MAPMT-based MMM and allows this system to perform within a factor of two compared with conventional multiphoton microscope.

The performance comparison of the two MMM systems can also be evaluated for the imaging of biological tissues. The specimen is an ex-vivo brain tissue section with neurons expressing green fluorescent protein (GFP). Thy1-GFP transgenic mice are deeply anesthetized with 2.5% Avertin (0.025 ml/g i.p.) and transcardially perfused with PBS, followed by 4% paraformaldehyde. Brains are dissected and placed overnight in cold 4% paraformaldehyde. 1-mm thick coronal sections are taken by vibrotome, mounted and coverslipped on microscope slides using adhesive silicone isolators (JTR20-A2-1.0, Grace Bio-Labs, Bend, Oreg.). The specimen is imaged in 3D with both CCD-based MMM and a MAPMT-based MMM. The objective used is 20×water immersion with NA 0.95 (XLUMPLFL20XW, Olympus, Melville, N.Y.). The input laser power is 300 mW at 890 nm wavelength. The frame rate is 0.3 frames per second with 320×320 pixels. The slow frame rate is set in order to collect enough emission photons up to 120 μm deep. The total imaging depth is 120 μm with 1.5 μm depth increment. Representative images are shown in FIG. 5. The first column of images are from CCD-based MMM at surface, 30 μm, and 75 μm deep. The second column of images are the ones from MAPMT-based MMM, raw images and the third column are after deconvolution processing. On the surface, the dendritic structures of neurons are visible in all images. However, the image from CCD-based MMM does not provide as good contrast of neurons as MAPMT-based MMM. This is because some of the emission photons that are initially forward propagating into the tissue are eventually backscattered. These backscattered photons are acquired in the incorrect pixels of the CCD and degrades the image SNR. Starting at about 30 μm, background noise increases and thin dendrite structure becomes invisible in CCD-based MMM images. On the other hand, in the images from MAPMT-based MMM, dendrites are still visible due to lower background noise and higher SNR. In the image of 75 μm deep from MAPMT-based MMM, ghost images of a bright cell body appear in the neighboring pixels. The ghost images are restored to the original image after the deconvolution process is applied. And also it is noted that the intensity of the original image is increased.

However, additional improvements of this system can be made. First, since the MAPMT is positioned in the image plane, the location of each excitation focus corresponds to the center position of the matching pixel of the MAPMT. The effective detector area scales quadratically with the separation of the foci. Therefore, with wider foci separation, the MAPMT has higher collection efficiency for scattered emission photons. In the current configuration, the excitation foci are separated from each other by 45 μm so that the effective detector area for each channel of the MAPMT is 45 μm×45 μm. The size of imaging field with 8×8 foci becomes 360 μm×360 μm. As the excitation foci are separated more, the system becomes less sensitive to the scattering of emission photons. The maximum separation of excitation foci is limited by either the field of view of the objective or apertures of other collection optics. The 20×water immersion objective used has the field of view of 1000 μm in diameter. This allows positioning the foci as far apart as almost 100 microns in this example.

A limitation of the MAPMT-based MMM system compared with a CCD-based MMM design is that the signals are de-scanned. In the de-scanned configuration, emission photons are processed by more optical elements including the scanner mirror before they are collected at the MAPMT suffering more optical loss at each reflection. Further, the de-scanned geometry also has a longer optical path that contributed to the loss of some scattered photons due to the finite aperture of the optics. The signal collection efficiency is approximately 70% in this example due to additional optical elements. An MAPMT-based MMM system in a non-de-scanned geometry for example can recover this loss.

The MAPMT is manufactured with a current quantum efficiency of about 20% compared to 80% quantum efficiency of the CCD camera. However, MAPMT has very low noise. It has 20 dark counts per second without cooling and can be several orders of magnitude lower with cooling. Since the MAPMT has a readout rate of approximately 20 KHz, the typical dark count per pixel. is less than $1\times10^{-3}$. In comparison, the CCD noise is dominated by both read noise and dark noise which are a few counts per pixel. Therefore, for very low photon count situation, i.e. dim sample or high frame rate, the MAPMT system can have superior performance. MAPMTs with higher sensitivity cathode materials such as GaAsP can provide a system with a quantum efficiency up to about 40-50%.

The photon sensitivity of each channel is not equal and can vary up to 50%. This effect is further compounded by the Gaussian geometry of the excitation beam which results in higher excitation efficiency at the center pixels verses the edge region. This problem has been solved previously using multiple reflecting beam splitter to generate equal intensity beam-lets. The MAPMT-based MMM system can be further improved by utilizing this type of beam splitter with an additional flat field correction algorithm to remove inherent sensitivity non-uniformity of the MAPMT.

There is also cross talk between neighboring pixels of MAPMT. The typical crosstalk is minimal at about 2% when the photons are collected at the center of each pixel. However, this cross talk can be removed by post-processing of the image similar to ghost image removal discussed previously.

In MMM imaging, more power of excitation light is required. Assuming that input power of 10 mW is needed for each excitation focus, generation of 64 excitation foci requires 640 mW input power. In the imaging of turbid tissue specimens, more input power is required to compensate the signal loss due to excitation photon scattering. In case of a tissue specimen whose mean free path length is 160 μm at excitation wavelength, the input power of 2200 mW is required to image at 100 μm deep, assuming that signal level is decreased only due to excitation photon scattering and there is no change in collection efficiency of emission photons. Therefore, the current power of Ti-Sapphire laser is limited for MMM imaging and can further increase in imaging speed by the use of even more foci.

Figure 6:
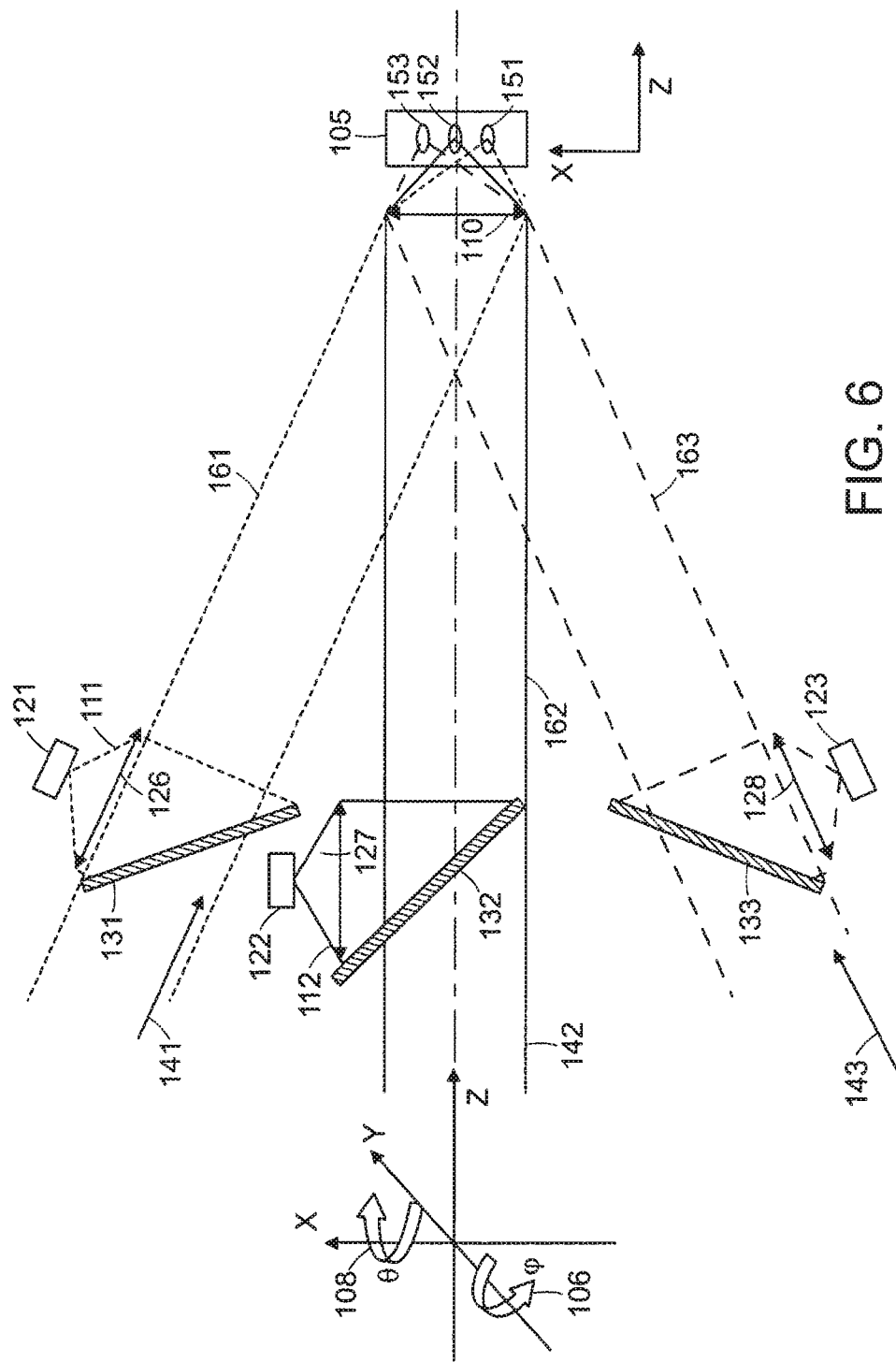
FIG. 6 illustrates a method and apparatus for multi-focal, multi-photon microscopy (MMM) according to a preferred embodiment of the invention, showing parallelized illumination and detection device with a common focusing device.

Referring to FIG. 6, a preferred embodiment provides for parallelized illumination and detection device which uses a common focusing device, such as an objective lens. The device provides simultaneous measurement of intensity, lifetime, spectroscopic or other information from the focal spots (foci 151, 152, 153). Light from a first illumination light path 141, a second illumination light path 142 and a third illumination light path 143, which paths present to each other at relative angles, enter a common focusing device 110 (such as an objective lens). The focusing device 110 generates from each illumination light path 141, 142, 143 a separate intensity cone. A first detector 121, a second detector 122 and a third detector 123 detect light generated by the intensity cones associated with each first, second and third illumination path, respectively. Light from a first illumination path 141 illuminates the focus spot 151 in the sample 105, with the detected light following a first illumination and detection light path 161 and first detection light path 111 to reach the first detector 121. Similarly, light from second and third illumination paths 142, 143 illuminate the focal locations 152 and 153, respectively, in the sample 120, with the detected light following second and third illumination and detection light paths 162 and 163 and second and third detection light path 112 and 113 to reach the second and third detectors 122 and 123, respectively.

In the multi-photon case, light from each path generates a 3D intensity distribution in its associated focus, according to the multi photon excitation process. The detectors 111, 112,113 detect all the light in the 'detection cone' associated with their active area. This light includes light generated by the light path associated with each detector (for example, light from the first focus 151 is detected by first detector 121), as well as light that is generated in the first focus 151 but scatters around the first focus 151 on its way to the first detector 151, and light that is generated in the second and/or third foci 152, 153 and is then scattered into the detection cone of the first detection light detection path 111.

In the confocal case, a confocal pinhole is placed in front of the detectors, for instance, in FIG. 6 a confocal pinhole can be placed between each detector 121, 122 and/or 123 and the associated reflectors and collimation lens 126, 127, 128, 131,132 and/or 133, respectively. As a consequence of the pin-hole impeding much of the scattered light, according to the confocal principle, only light from the focal spot associated with that detector is collected in each detector. For example, following the first light path, only light from the 3D light distribution in the first focus 151 is detected by detector 121. A setup could as well consists of a mixture of detectors with and without a confocal pinhole.

In order to reduce cross talk between the light beams due to scattering, the illumination light and the associated detection can be time multiplexed.

Still referring to FIG. 6, a device according to the invention can become an imaging device by the illumination beams 141,142,143 being angle-scanned with respect to the focusing device 110. The imaging of the x-y planes is enabled by rotating the device through two perpendicular angles theta and phi around the x and y axes, respectively. The intensity information is recorded along with the angular position of the device and reconstructed by a image processor. Imaging of zy planes can be achieved as well by scanning the sample in respect to the imaging device in xy. In an imaging mode, in which the beams are scanned, the device is capable of simultaneously generating 2D images of sub-regions of samples. By simultaneously imaging with each separate illumination and detection pathway, the speed at which images are generated can be increased by the number of illumination paths and detection channels.

Imaging in the z plane occurs by moving the imaging device with respect to the sample, or vice-versa. The intensity information is recorded along with the z-position of the sample or device and reconstructed by an image processor.

Figure 7:
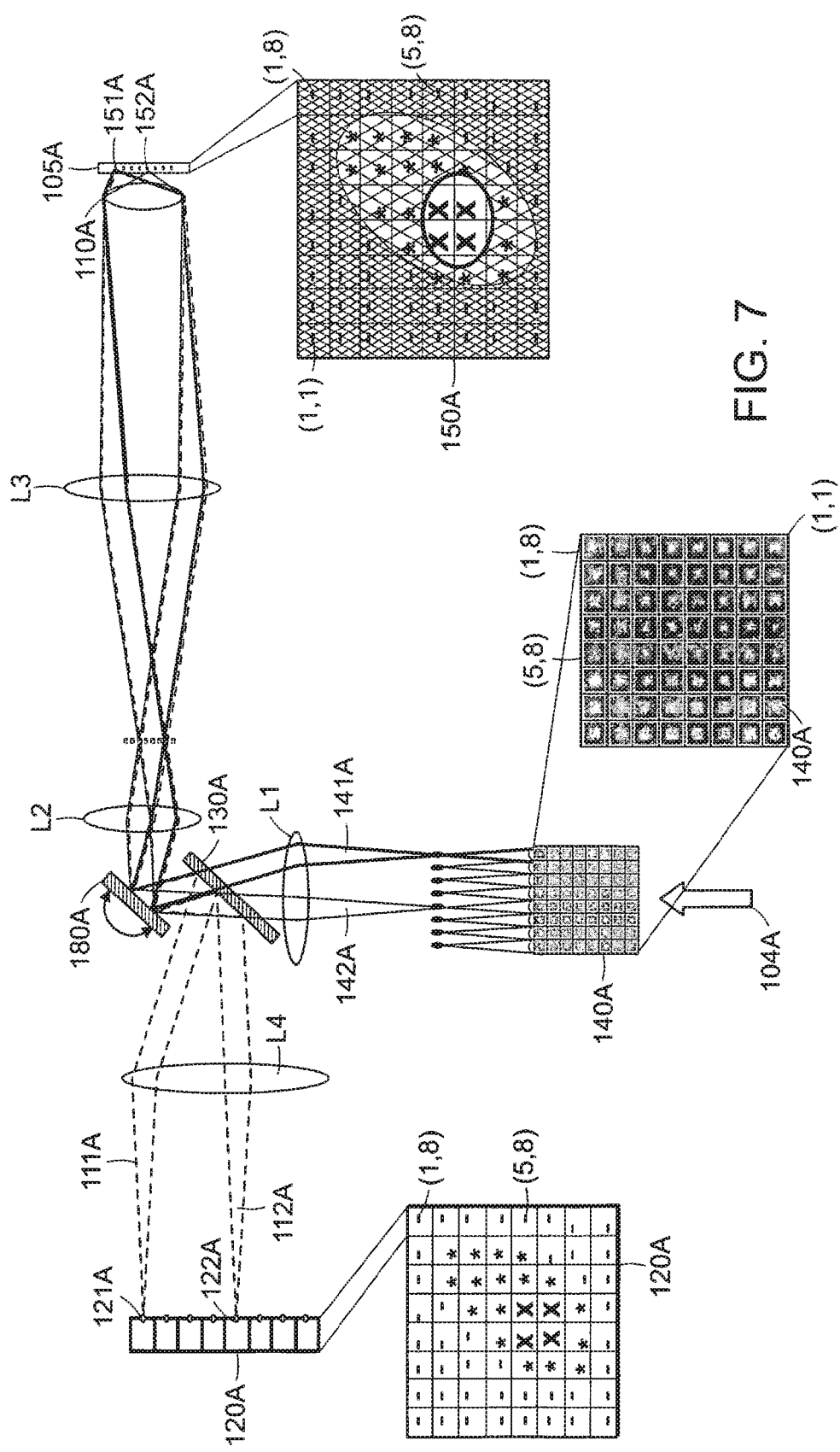
FIG. 7 illustrates a method and apparatus for multi-focal, multi-photon microscopy (MMM) employing scanning and multi anode PMT's, according to a preferred embodiment of the invention.

Another embodiment according to the invention provides for a multifocal, multiphoton microscope based on MAPMT, as illustrated in FIG. 7, in which an expanded excitation beam 104A comes from bottom of FIG. 7 and illuminates a square microlens array 140A. A plurality of optical pathways is generated by the micro lens array 140A in conjunction with lens L1; for instance, in the embodiment illustrated here the microlens array 140A splits the excitation beam 104A into 8×8 multiple beams (i.e., 64 beamlets). In FIG. 7, only two beamlets 141A, 142A are ray-traced. A specimen 105A is scanned with an 8×8 array of excitation foci 150A, which includes focus spots 151A and 152A illuminated by beamlets 141A and 142A respectively. The sample area that each excitation focus covers can be relatively small the focus is in x and y direction, the full width half maximum (FWHM) of the focus is 200-1000 micro meter. In z direction the FWHM is 200-5000 micro meter. In an imaging configuration each foci scans an area of the size of the distance of the foci, meaning 10-1000 microns (the scanning is accomplished by an optical scanner 180A such as, a galvo-scanner). The two lenses L2 and L3 guide the plurality of optical pathways onto the rear aperture of the focusing device 110A. The detection light paths, 111A and 112A, respectively, resemble the illumination light path until the light paths are separated by a light reflector, which is in this case a dichroic mirror 130A. The light is then focused by a common lens L4 onto the multi anode PMT detectors 120A. The emission beam-lets are collected at pixels 121A and 122A, respectively, of a multi anode PMT (MAPMT) 120A. The MAPMT 120A, which has the same number of pixels as excitation beamlets, detects the signal of 8×8 pixels synchronized with the scanning. The intensity information is recorded along with the angular position of the scanner and reconstructed by an image processor.

Figure 8:
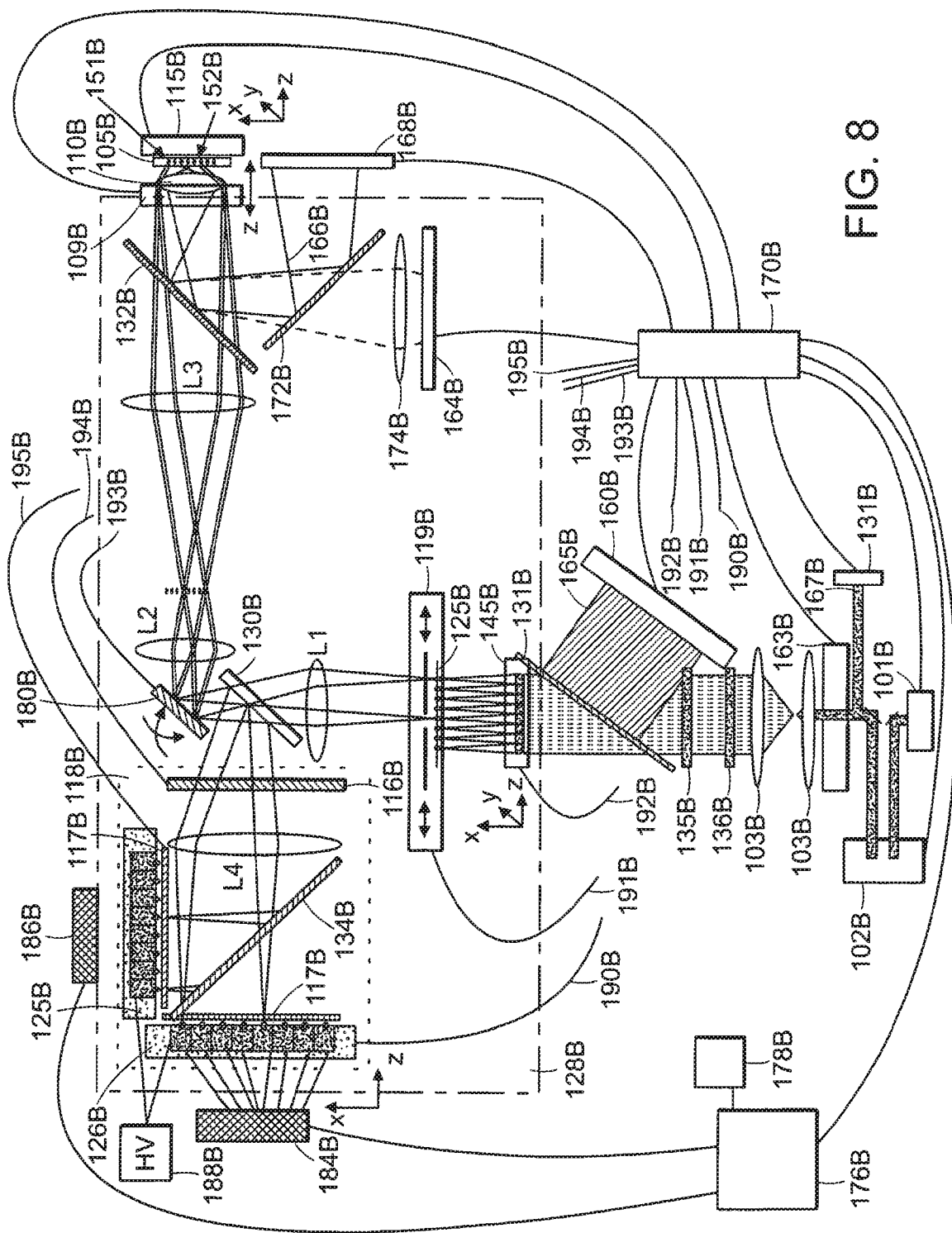
FIG. 8 illustrates another method and apparatus for multi-focal, multi-photon microscopy (MMM) employing scanning and multi anode PMT' s, according to a preferred embodiment of the invention.

As shown in FIG. 8, a further embodiment according to the invention provides for a multifocal, multiphoton microscope based on MAPMT, in which an expanded excitation beam 104B comes from laser 101B and illuminates a micro lens array 140B. A plurality of optical pathways is generated by the micro lens array 140B in conjunction with lens L1; for instance, in the embodiment illustrated here two beamlets 141B, 142B are ray-traced. A specimen 105B is scanned with an array of at least one excitation foci 151B and/or 152B which are illuminated by beamlets 141B and 142B respectively. The scanning is accomplished by a scanner 180B. The two lenses L2 and L3 guide the plurality of optical pathways onto the rear aperture of the focusing device 110B. The detection paths, 111B and 112B, respectively, depart from illumination light path when separated by dichroic mirror 130B. The light is then focused by a common lens L4 and reflector 134B onto two multi anode PMT detectors 120B, 124B. The MAPMT detectors 120B, 124B each detect the same number of pixels as are emitted excitation beamlets, integrating the signal of the at least one pixel synchronized with the scanning.

A z-piezo actuator 109B (such as MIPOS 250 SG, micro-objective positioning system, integrated strain gauge motion: 200 μm (closed loop), Piezo System Jena controllable by controller 170B is attached to the objective lens 110B in order to move it in the z direction for 3D image generation. The sample 105B is attached to a sample stage 115B, which can be moved in x, y and z directions, also controllable by controller 170B and/or computer 176B. Light reflector 134B (such as, for example, a dichroic mirror) is positioned in the detection pathways to enable multi channel imaging by a first MAPMT detector 120B and a second MAPMT detector 124B, for multi channel imaging.

An IR block filter 116B (such as e700sp Special, Multi-Photon Blocking, Block 750-1000 nm>OD 6, Chroma Technology Corp is positioned in the detection pathway to separate the long wavelength excitation light from the short wavelength detection light. The filter 116B is exchangeable with a variety of filters or can be removed completely for reflected light confocal imaging. The filter 116B can be mounted on a motorized mount, which allows it to exchanged via a controller 170B and/or computer interface 176B. A band-pass filter 117B (such as 560DCXR for detecting DAPI and FITC, Chroma Technology Corp) (560DCXR for the transmission of light generated by the excitation of GFP and Rhodamin, HQ460/40 for the transmission of light generated by the excitation of DAPI, HQ630/60 for the transmission of light generated by the excitation of Alexa 594 bandpass; Chroma Technology Corp) is positioned in front of each of the multi anode PMTs 120B, 124B, in order to detect certain spectra. The band-pass filters 117B, 117B are exchangeable with other different filters and can be mounted on a motorized mount enabling changing of filters via a controller 170B and/or computer interface 176B. The same sample region can then be imaged with a different set of band-pass filters for more than two-color imaging.

A detection-part light-shield enclosure 118B is used to shield the detection part of the apparatus from ambient light. A variable iris 119B (such as for the case of a manual version D20S—Standard Iris, 20.0 mm max. Aperature; Thorlabs. Motorized versions of equivalent devices are available as well) is positioned in the focal plane of the micro lens array 140B in order to enable single spot illumination. For 8×8 foci imaging, the iris 119B is relatively open and for fewer or single spot imaging the iris is relatively closed, so that only a few or one micro lenses illuminate the sample. The variable iris 119B does not have to be in a round shape; and it will be square in shape when only a certain array of micro lenses should be blocked to enable illumination with a view of selected foci only. The variable iris 119B can be motorized and controlled via controller 170B (such as, for example by connection 191B), and/or via the computer 176B.

A micro lens foci mask 125B (such as a thin (for example 0.3 mm) aluminum sheet in which small wholes (for example 0.5 mm wholes) are drilled, at the points of where the micro lens focuses) positioned proximate the micro lens array 140B is a pinhole mask with a large pinhole size that enables the transmission of most of the light focused by the micro lenses, but otherwise it blocks ambient and stray light from the laser.

A first reflector 131B generates a first laser reference beam 165B from the incident laser beam (for monitoring the laser illumination power, wavelength and angular pointing stability). The reference beam 165B projects upon the diode or detector 160B which generates a signal that measures the laser illumination power, wavelength and angular pointing stability.

A further embodiment of the invention provides for a scan reference beam 166B from a scan reference beam illumination source 168B to be projected via reflector 172B and reflector 132B onto the scan region, whereupon the returning scan reference beam returns via reflector 132B to pass through dichroic 172B and lens 174B to be received by detector 164B. The scan beam is provided for monitoring the scanning accuracy. Detector 164B can be a diode or CCD detector or another type detection device. As shown in FIG. 8, an embodiment of the invention can provide for the detector 164B to be a CCD camera, which can be used to compare images generated by CCD camera detection methods and other detection methods according to the invention that employ one or more multi anode PMTs as described above.

A high voltage power supply 188B supplies power to the multi anode PMTs. Multi channel photon counting cards 184B, 186B are connected to each element of the MAPMTs, with one photon counting device for every multi anode PMT element, such as, for example, MAPMT elements 120B and 124B.

A computer 176B (including input devices, such as, for example, a keyboard and mouse) can be provided in one embodiment, connected to computer display 178B. The computer 176B can be connected to controller 170B.

The computer 176B controls numerous elements of the invention either directly and/or indirectly through controller 170B, and one skilled in the art will appreciate that numerous alternative configurations can be implemented within the scope of the invention.

One embodiment provides for the computer 176B to be programmed with a processing software and for the computer 176B to control a number of optical elements through a variety of electronic interfaces. For example, without limitation, the computer 176B and/or the controller 170B can be electronically interfaced with the scanner 180B and the multi channel photon counting cards 184B, 186B to perform the steps of scanning and data acquisition. Further the computer 176B can perform imaging post-processing steps. The display 178B can be used to display the acquired images in real-time after further processing.

A laser power attenuator 163B can be provided to control the laser incident power. The attenuator 163B can be controlled by the controller 170B and/or by the computer 176B in order to enable power adjustments for different samples and different locations in samples. During imaging at different depths in the sample, for example, the laser power can be automatically adjusted, so that the laser power can be increased at higher penetration depth. The attenuator 163B is integrated in order to make laser power adjustments, such as, for example, low power at the sample surface and increased power at increased penetration depth.

A third reflector 133B generates a second laser reference beam 167B from the incident laser beam (also for monitoring the laser illumination power, wavelength and angular pointing stability). This second laser reference beam 167B projects upon a second diode or detector 161B to generate a signal that measures the laser illumination power, wavelength and angular pointing stability. A laser power attenuator 163B controls the laser incident power and is integrated in order to make laser power adjustments, such as, for example, low power at the sample surface and increased power at increased penetration depth. Laser 101B is an illumination light source, such as a titanium sapphire laser (Mai Tai HP, Spectra Physics).

Multi-photon microscopy works most efficiently with short laser pulses. Owing to dispersion, the optical elements in the illumination pathway broaden the initially short laser pulse. The pulse compressor 102B is built from a pair of standard high reflectance mirrors and a pair of prisms (IB-21.7-59.2-LAFN28, Material: LaFN28; CVI Laser Corp., Albuquerque, N.M. 87123) mounted on translational and rotational stages pre-chirps the laser pulse in order to attain a short laser pulse in the focus of the objective lens.

A confocal pinhole array optionally can be placed between either of the multi anode PMT arrays 120B, 124B and the band-pass filters 117B, 117B, respectively. This option enables the system to be used for confocal microscopy or for multi-photon microscopy with confocal detection.

A telescope 103B expands the laser beam. With different expansion ratios, a different number of micro lenses can be illuminated. With a small beam expansion for example, a relatively smaller array of 2×2 micro lenses can illuminated and, thus, an array of only 2×2 foci is generated. As the beam expansion is made larger, an array of 8×8 or more micro lenses can be illuminated and, thus, an array of 8×8 or more foci is created. A further preferred embodiment employs a set of at least two mirrors 135B, 136B after the telescope 3B for precise beam alignment.

A mechanical micro lens holder 145B enables the precise positioning of the micro lens array 140B with respect to the multi anode PMTs 120B, 124B in the x, y and z directions. The holder 145B can be a motorized holder and can be controlled through a computer interface 176B, or, alternatively, can be controlled via a controller 170B, which controller in turn can be directed by computer 176B.

Mechanical multianode PMT holder 125B, 126B enables the precise positioning of the multi anode PMTs 124B, 120B, respectively, with respect to the micro lens array 140B in the x, y and z directions. The holders 125B, 126B can be motorized holders and can be controlled through a computer interface 176B, or, alternatively, can be controlled via a controller 170B, which controller in turn can be directed by computer 176B.

The computer 176B, or the controller 170B, or the computer and controller together can be configured to control automatically or to control in supervised fashion, one or more of the following elements, without limitation: the scan reference beam illumination source 168B, the sample piezo stage 115B, the objective z-piezo stage 109B, the scan reference beam detector 164B, the scanner 180B (by connection 193B), the IR block filter 116B (by connection 194B), the band-pass filters 117B (for example, by connection 195B), the laser source 101B, the laser attenuator 163B, the first laser reference beam detector 161B, the second laser reference beam detector 160B, the pulse compressor 102B, the multi-photon channel counting cards 184B, 186B, the mechanical multi-anode PMT holders 125B, 126B (for example, by connection 190B), the variable iris 119B (such as, for example, by connection 191B), and the mechanical micro lens array holder 145B (for example, by connection 192B).

The focal region has a focal pattern variation in xy plane. The foci can be distributed unevenly, e.g., the rows and columns do not have to be spaced uniformly.

Also, a system can be built, in which there are additional rows and/or columns of PMT's at the outer region of the array of detection tubes. For example, there can be more than 8×8 rows and columns in both the micro lens array and the detector. This is particularly important for detecting scattered photons of the outer foci and for using the information of the scattered photons from the outer foci for deconvolution purposes.

Further, an embodiment of the invention provides for a system in which there are more detector elements than there are foci, so that a plurality of detector elements (or detection pixels) collect the photons of one, optically conjugated foci. For example, a 16×16 detector array can used as a detector device, while an array of 8×8 foci can be illuminated by an 8×8 multi lens array. Smaller and larger PMT-to-foci ratios can be utilized. In particular, a detector array in which one foci is optically conjugated to an uneven number of detector elements can be employed. This is important for detecting scattered photons in the neighboring channels of the to the focus optically conjugated detector and for using the information of the scattered photons for deconvolution purposes.

The image of the sample is formed by scanning in the optical plane (xy) when the intensity signal from the detectors is correlated with the foci positions. The foci scan the specimen in the x direction, then move an increment in the y direction, and then raster in the x direction again until the sample is fully covered at some desired resolution. During the rastering, intensity light signals are recorded by the multi anode PMT. These signals are then saved along with the foci positions in the computer and can be concurrently or afterwards displayed by the computer display or other graphics outputs. The foci positions are known by the scanner position (beam scan) or the sample position (stage scan). The smaller the step increments, the higher the resolution the final image will be. The scanning can be performed in a raster fashion, or in many other ways, such as with time multiplexed methods, or scanning simultaneously at different depths.

Figure 9:
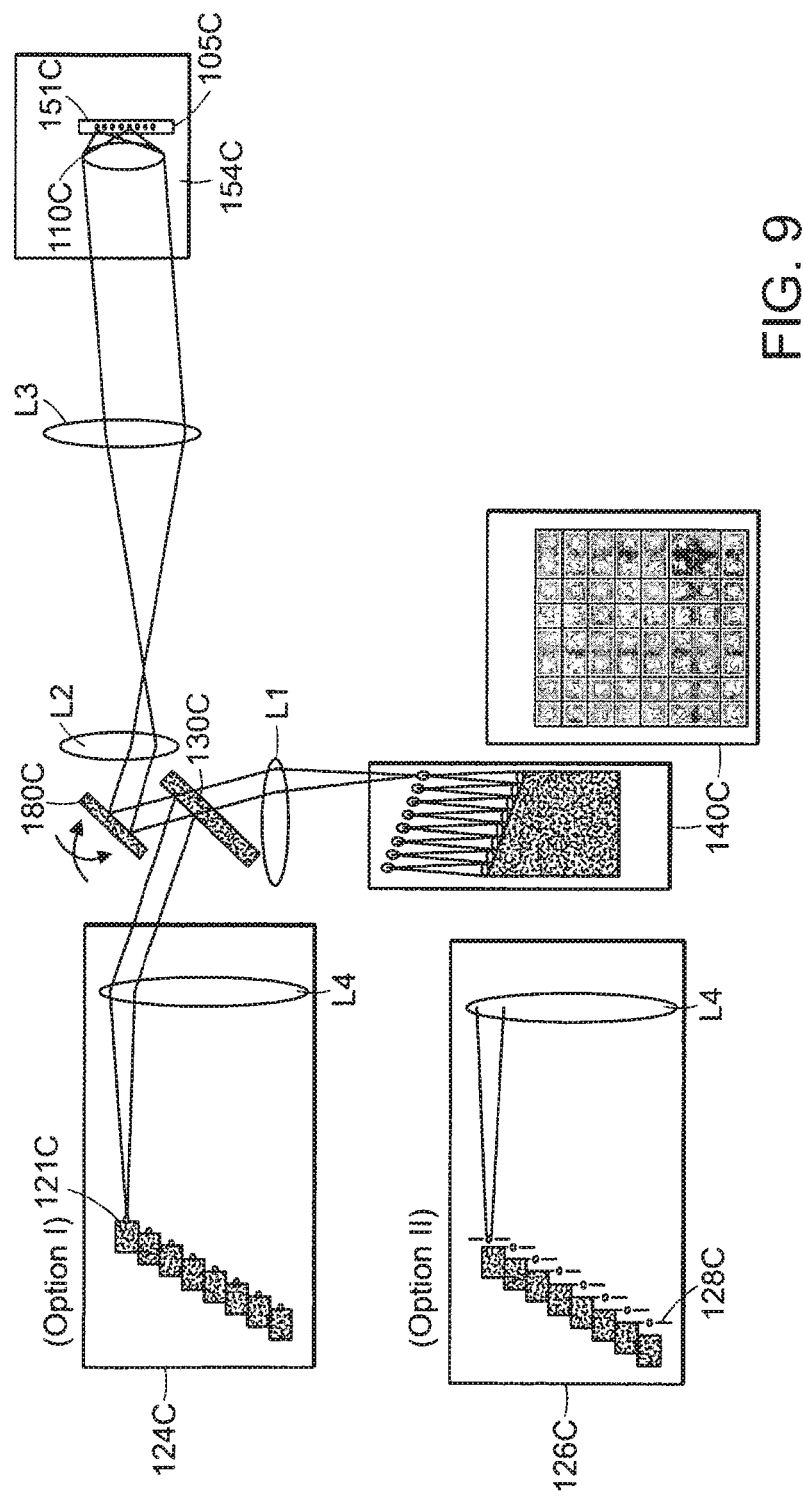
FIG. 9 illustrates generating and detecting a 3D foci pattern in a focal region.
Figure 10B:
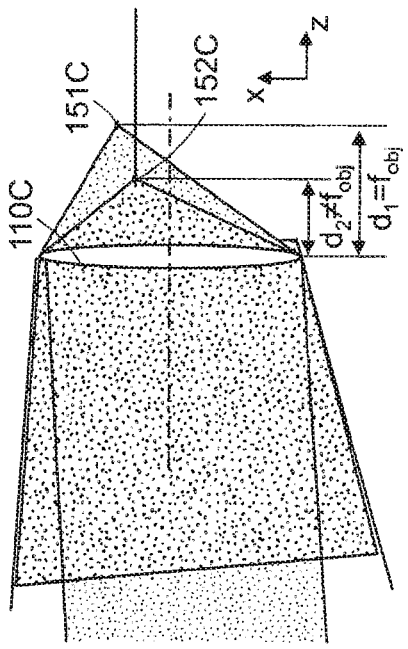
Figure 10D:
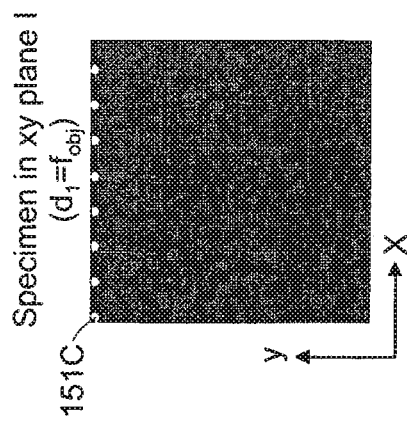
Figure 10A:
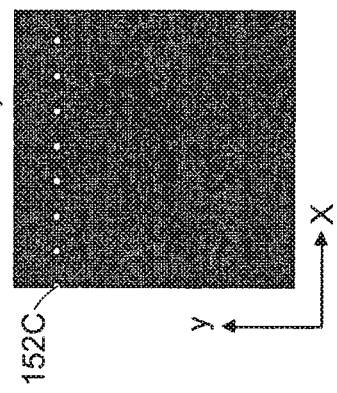
Figure 10C:
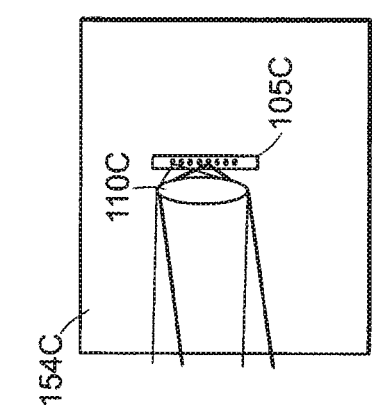

Referring to FIG. 9, an embodiment of the invention provides for generating and detecting a 3D foci pattern in focal region 154C. A source of light is directed onto a micro lens array 140C and a plurality of optical pathways is generated by the micro lens array 140C in conjunction with lens L1; for instance, in the embodiment illustrated here, the microlens array 140C splits the excitation beam 104C into 8×8 multiple beams (i.e., 64 beamlets). In FIG. 9, only one beamlet 141C is ray-traced. A specimen 105C is scanned with an 8×8 array of excitation foci, which includes focus spot 151C illuminated by beamlet 141C. The scanning is accomplished by an optical scanner 180C. The two lenses L2 and L3 guide the plurality of optical pathways onto the rear aperture of the focusing device 110C. The detection light path, 111C, resembles the illumination light path until the light paths are separated by a light reflector, which in this case is a dichroic mirror 130C. The light is then focused by a common lens L4 onto the multi anode PMT detector pixel element 121C. Changing the focal length or the positions of the micro lenses of the microlens array 140C with respect to each other generates collimated and non-collimated beams at the back aperture of the objective lens 110C. These beams generate a 3D pattern of foci. The 3D pattern of foci generates light which is collected by the detector array. According to the positions along the optical axis of the micro lens array, the positions of the PMT's are changed. In case of one-photon illumination, such as is illustrated in the "Option I" detection region 124C, no confocal pinholes are placed in front of the detectors. In an alternative embodiment, such as is illustrated in the "Option II" detection region 126C, a plurality of confocal pinholes 128C are placed in front of the plurality of detectors cells. Each of the detection options 124C, 126C can be used for single photon and/or for multi photon imaging. The MAPMT, which has the same number of pixels as excitation beamlets, integrates the signal of 8×8 pixels synchronized with the scanning, although other array dimensions can also be used.

FIGS. 10(*a*)-(*i*) illustrate in greater detail the arrangement and progression of foci corresponding to the relative shifting in position of micro array lenses and MAPMT pixels shown in FIG. 9. FIG. 10(*a*) shows an expanded detail of the focal region with 3D foci pattern. FIG. 10(*b*) illustrates an array of excitation light beams (in this case, an array of 2×8 beams) illuminating a focusing device 110D, such as, for example, an objective lens, as viewed here in the x-z plane. In accordance with differing degrees of collimation of at least two of the light beams, focal points 151C and 152C are created for the two beams at certain distances, $d_1$ and $d_2$, respectively, along the optical axis (z-axis). According to the relative angle of the illumination light beams with respect to the optical axis, the array of foci are separated in the optical plane. Controlling parameters of the beams provider selection of a variety of 3D foci distribution(s). For collimated light, the excitation foci 151C is at a distance from the focal objective, $f_{obj}$, designated here as distance $d_1$. For a second beam that is not collimated perfectly, an excitation foci 152C is at a distance $d_2$ that is not equal to the focal objective, as depicted in FIG. 10(b). FIG. 10(c), depicting a "static" view of an x-y plane "slice" at focal depth $d_1$, illustrates a first row of 8 foci (of the 2×8 array in this example) all lying at the same focal depth $d_1$, understanding that any one of these foci may correspond with the 151D focus point in the x-z plane view of FIG. 10(b). Similarly, FIG. 10(d), depicting a "static" view of a second x-y plane at focal depth $d_2$, illustrates a second row of 8 foci (of the 2×8 array) all lying at the same focal depth $d_2$, any one of which foci might correspond with the 152C focus point in the x-z plane view of FIG. 10(b). FIG. 10(e) illustrates the separation of the two x-y planes as viewed in the y-z plane, where it can be seen that the two rows of foci are separated by a difference in focal depth $D=d_1-d_2$. FIG. 10(f) shows a 3D, 8×8 beam matrix (64 beams) of excitation foci that have been generated. Each row of 8 foci lies in a different z plane, as depicted in a view of the same set of 64 foci as seen in the y-z plane (FIG. 10(g)); this is a graphic depiction of a "still" configuration, i.e., without the array being moved in a scanning mode. FIG. 10(h) illustrates an x/y view in a scanning configuration, where each line of foci is scanned in the xy plane to cover the whole yx image in its particular z-plane. A number of xy planes are shown simultaneously, but actually each plane lies at a different focal depth on the z-axis. FIG. 10(i) provides a view of a section in the yz plane, illustrating the scanning configuration while the z/y scan is performed, i.e., scanning along the y axis and through multiple depth layers in z. As a result, a 3D volume can be imaged by only scanning the foci array in xy. Note that the x/y, x/z and y/z coordinates illustrate the associated planes; they can be displayed with an arrow in their positive or negative direction.

3D AM-PMT MMM can be used in multi photon endoscope device in accordance with another preferred embodiment of the invention (to be added).

Figure 11A:
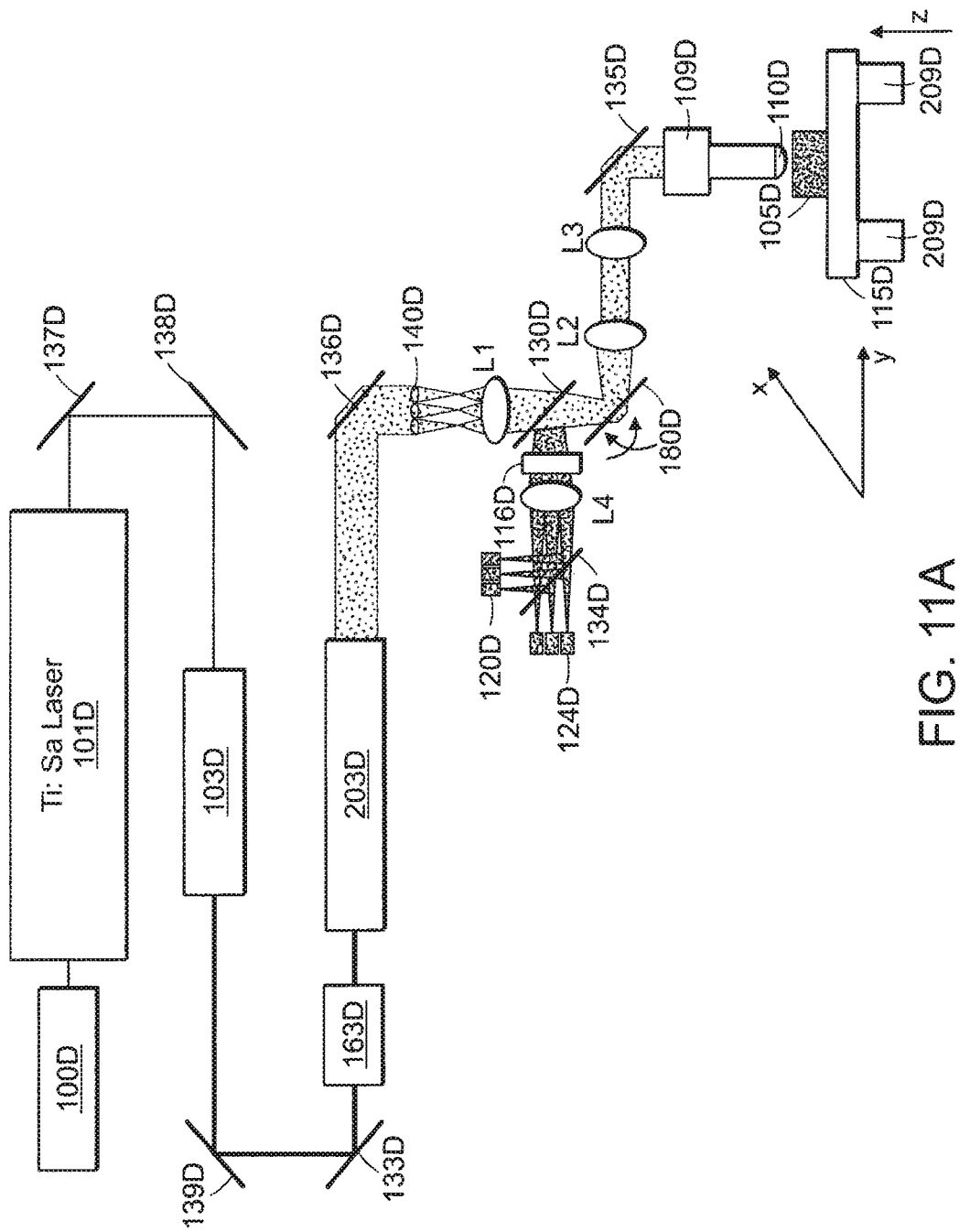
FIG. 11a illustrates a further method and apparatus for a 3D cytometer, based on multi-focal, multi-photon microscopy (MMM) employing scanning and multi anode PMT's, according to a preferred embodiment of the invention.
Figure 11C:
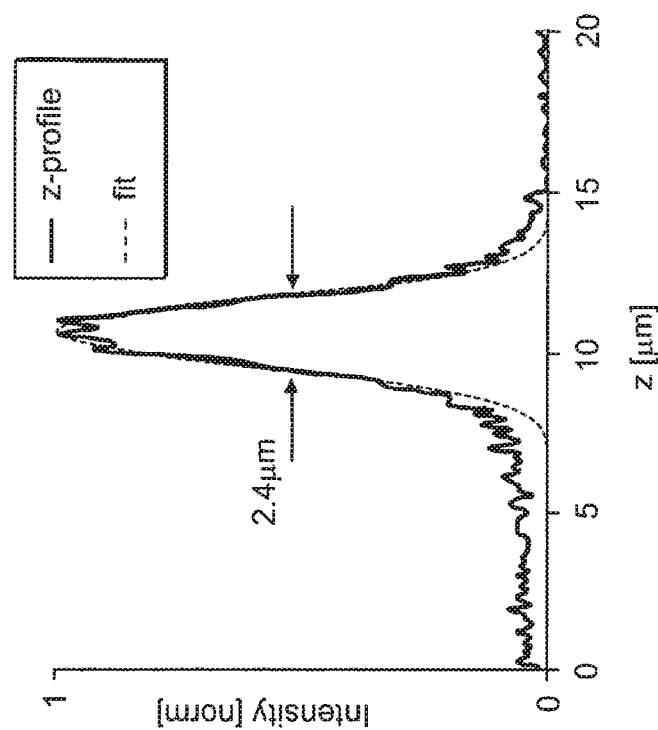
FIG. 11(c) illustrates the Z-profile and corresponding fit function of a 200 nm bead.

Referring to FIG. 11(c), a further embodiment provides for a 3D cytometer, based on multi-focal, multi-photon microscope with a multi anode PMT detector. A 10 W solid state pump laser 100D pumps a titanium sapphire laser 101D (Millennia X & Tsunami, Spectra Physics, Mountain View, Calif.), which generates maximum output power of 2.5 W at 800 nm, and 120 fs pulses at a repetition rate of 76 MHz. The light is conducted through two reflectors 137D, 138D and then passes through a first telescope 103D, two additional reflectors 139D, 133D, an attenuator 163D, and a second telescope 203D. After passing through another reflector 136D, the light is subsequently split into an array of beams by the micro lens array 140D and is transmitted by lenses L1, L2 and L3 onto the back aperture of the objective lens 110D, thus creating multiple foci in the focal plane. The micro beams are scanned by a xy-scanner 180D (Cambridge Technologies, Cambridge, Mass.). The fluorescence is collected by the same lenses and separated from the illumination light by a dichroic filter 130D and a two-photon block filter 116D. The fluorescence passes through lens L4 and is then separated into two spectral channels by the dichroic filter 134D and directed onto the multi-anode PMTs 124D, 120D. The degree of spectral separation can be chosen depending upon the application. The embodiment disclosed here uses a red/green and a green/blue filter to accomplish the spectral separation. The variation of the magnification of the telescope 203D enables the utilization of, for example, 4×4, 6×6 or 8×8 arrays of micro lenses, among other size arrays.

Figure 11B:
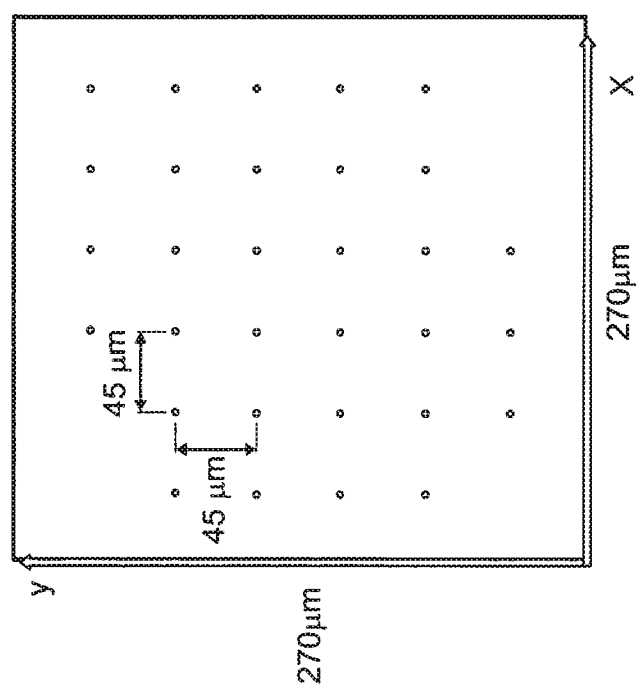
FIG. 11b illustrates an image of the array of foci in the focus of the objective lens; the foci are 45 micrometers apart resulting in a scanning field of 240 mm when 6×6 foci are utilized.

FIG. 11(b) illustrates an image of the array of foci in the focus of the objective lens, such image as can be taken by a CCD camera, where here the foci are not scanning. The foci are 45 μm apart in resulting in a potential scanning field of 240 μm when 6×6 foci are utilized.

FIG. 11(c) shows a z-profile and a corresponding fit function of a 200 nm bead. The system shows a resolution of 2.4 μm, which is close to a theoretical value of 2.2μm, considering the under-fulfillment of the back aperture of the objective lens. Acquisition speed for this scanning profile was 10 frames per second. The profile is averaged over 5 consecutive pixels, reducing the sampling from 30nm per pixel to 150 nm per pixel.

Figure 12A:
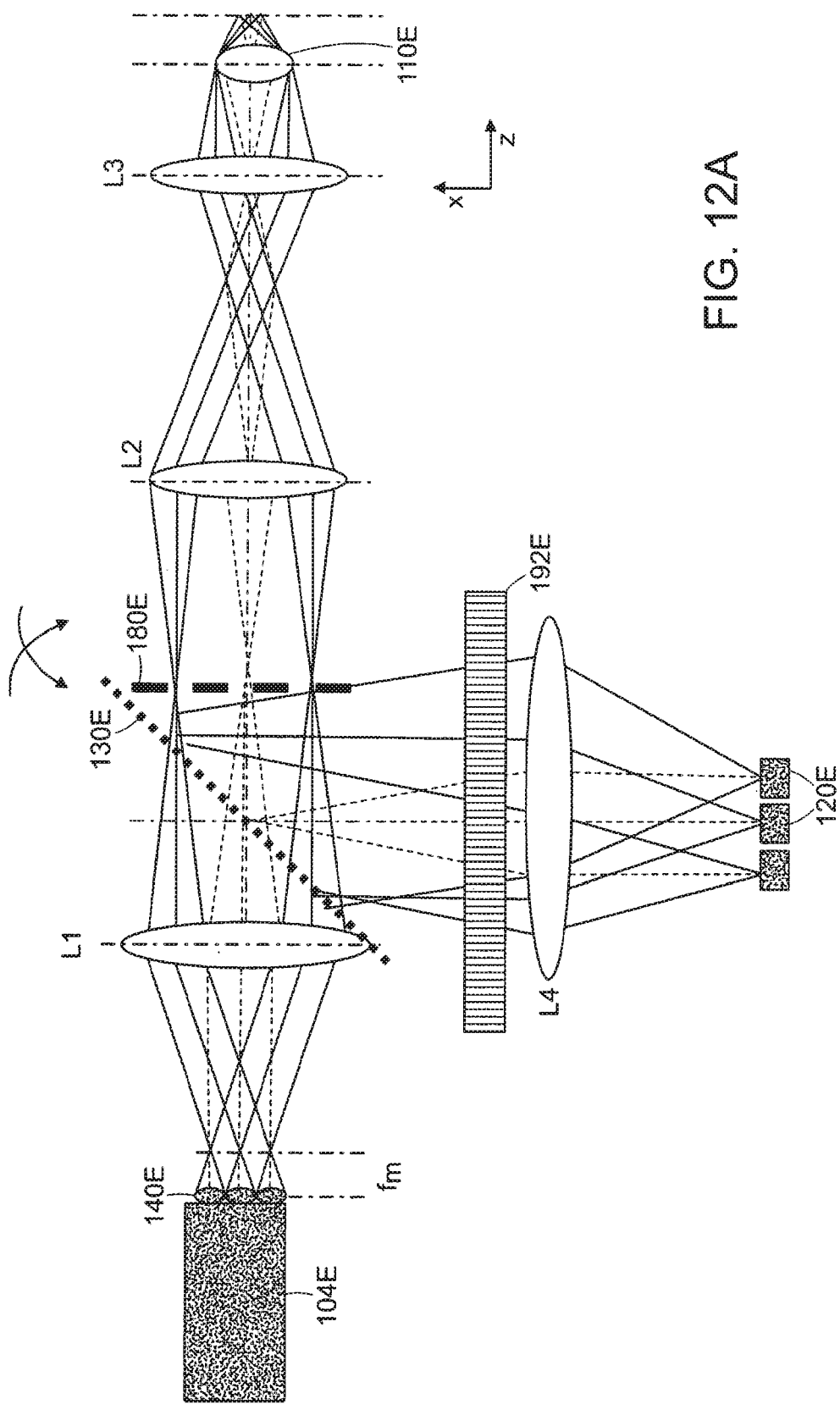
FIGS. 12(a)-(e) illustrates a further method and apparatus for multi color detection MMM employing scanning and multi anode PMT's according to a preferred embodiment of the invention: (a) the setup in the xz-plane; (b) the foci and their scanning in the focal xy-plane; (c) detection path in the yz-plane (d) detection path projected in the xz-plane; (e) the anodes of the multi anode PMT in the x/z and x/y plane in conjunction with the detected colors. In this case only visible light is shown. Any other light spectra can be separated, though.
Figure 12C:
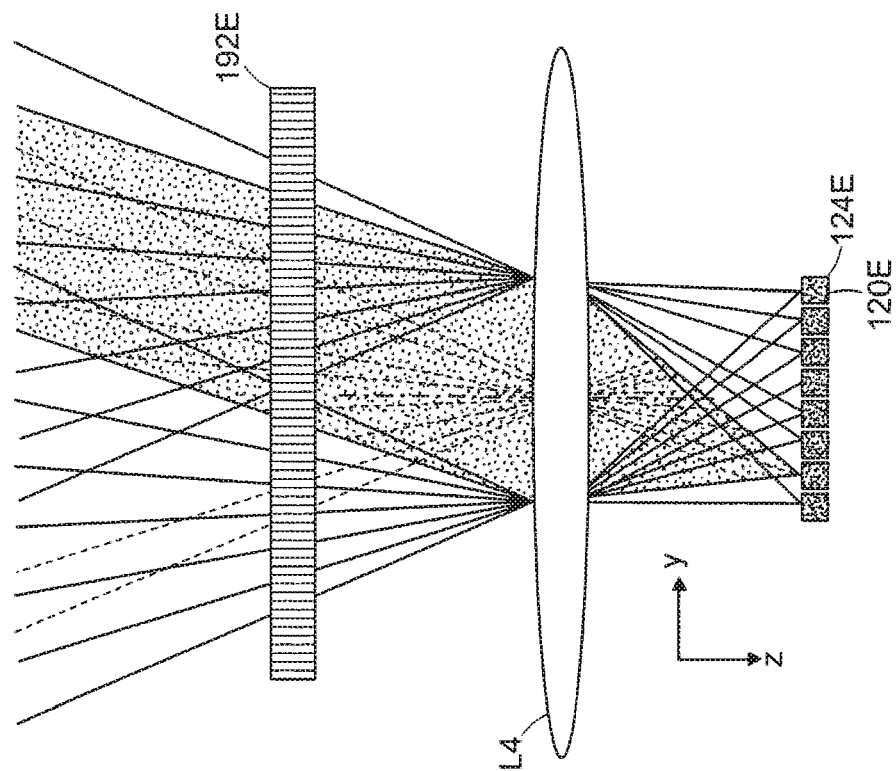
Figure 12B:
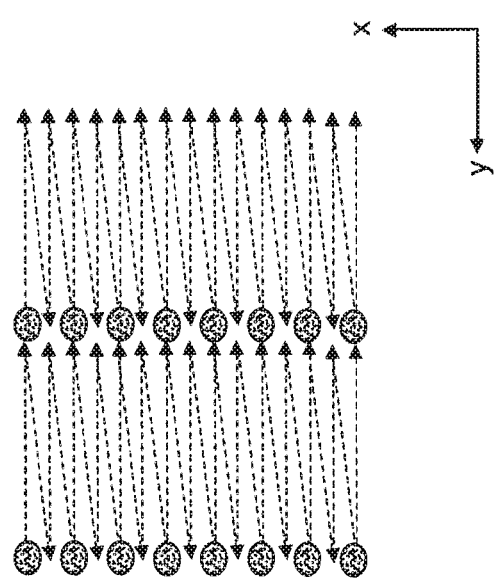
Figure 12E:
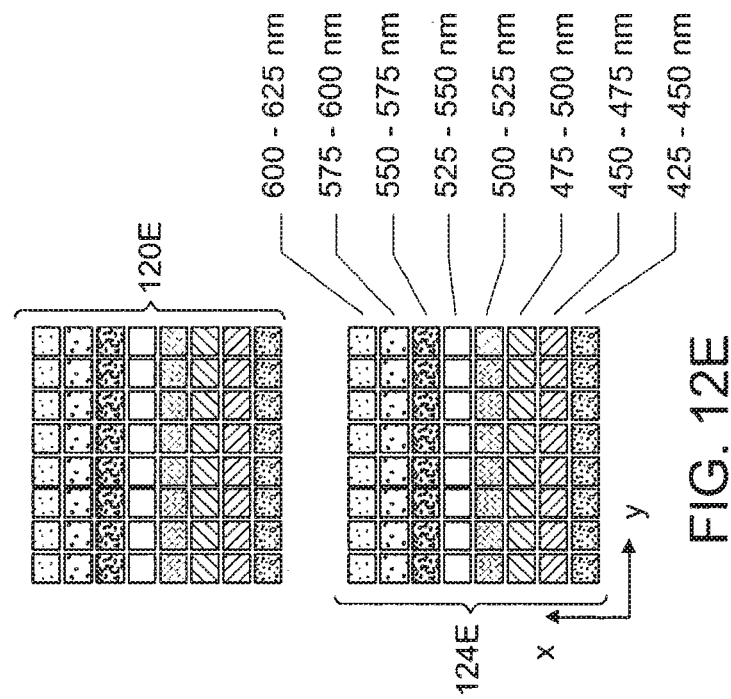
Figure 12D:
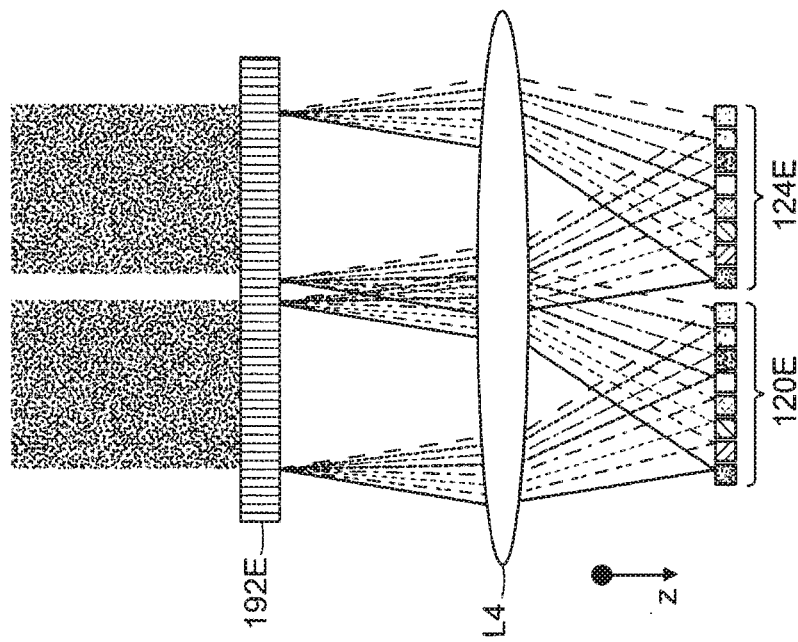

Referring to FIG. 12(a) a further embodiment of the invention provides for multi color detection MMM in the xz-plane. An array of 2×8 beams is generated by the micro lens array 140E. The setup here is illustrated with two 1×8 beam lines. The distance between the foci in each line is determined by the combination of the source beam configuration and the micro lens array 140E. Two light beams are conducted through the micro lens array 140E and intermediate optics onto the focal plane of the microscope in which they create two lines of 1×8 foci. For simplified visualization, in FIG. 12(a) only 3 of the 16 beam traces in a 2×8 setup are illustrated. The full field is then scanned by the mirror oscillation of the scanning mirror 180E, in which the scanning amplitudes need to be adapted to the distances of the foci. On the detection side a holographic diffraction grating 192E is incorporated that diffracts the multiple wavelengths emitted from the sample onto the photo-multiplier arrays of two stacked multi-anode PMTs 120E, 124E. In the setup the two multi-anode PMTs will be stacked on top of each other, each serving as a spectral detection device for one line of 1×8 foci. The grating 192E properties (pitch/inch) and the focal length of the focusing lens (L4), which determines the distance between the grating and the multi-anode PMT, have to be chosen in accordance to the anticipated fluorescent probes used for staining the tissue sample. For this embodiment, a transmission grating 192E is used. Nevertheless, comparable and/or better efficiency can be achieved in embodiments that use a reflection grating or a prism. FIG. 12(b) illustrates the illumination foci and their scanning in the focal xy-plane. Scanning is indicated for two arrays of 8 foci each. FIG. 12(c) shows the detection path of two beams projected in the yz-plane through grating 192E and lens L4 onto the stack of two AM-PMTs 120E, 124E. FIG. 12(d) shows the detection path projected in the xz-plane, where the beams are depicted passing through grating 192E and lens L4 with each of eight color bands being collected by the two AM-PMTs 120E and 124E. FIG. 12(e) illustrates the anodes of the multi-anode PMTs 120E, 124E in the x/y plane, showing that the 8×8 anode arrays of the detectors each detects one of the two 1×8 beam lines, where each 1×8 beam line has been diffracted by the grating 192E into eight color bands.

Figure 13:
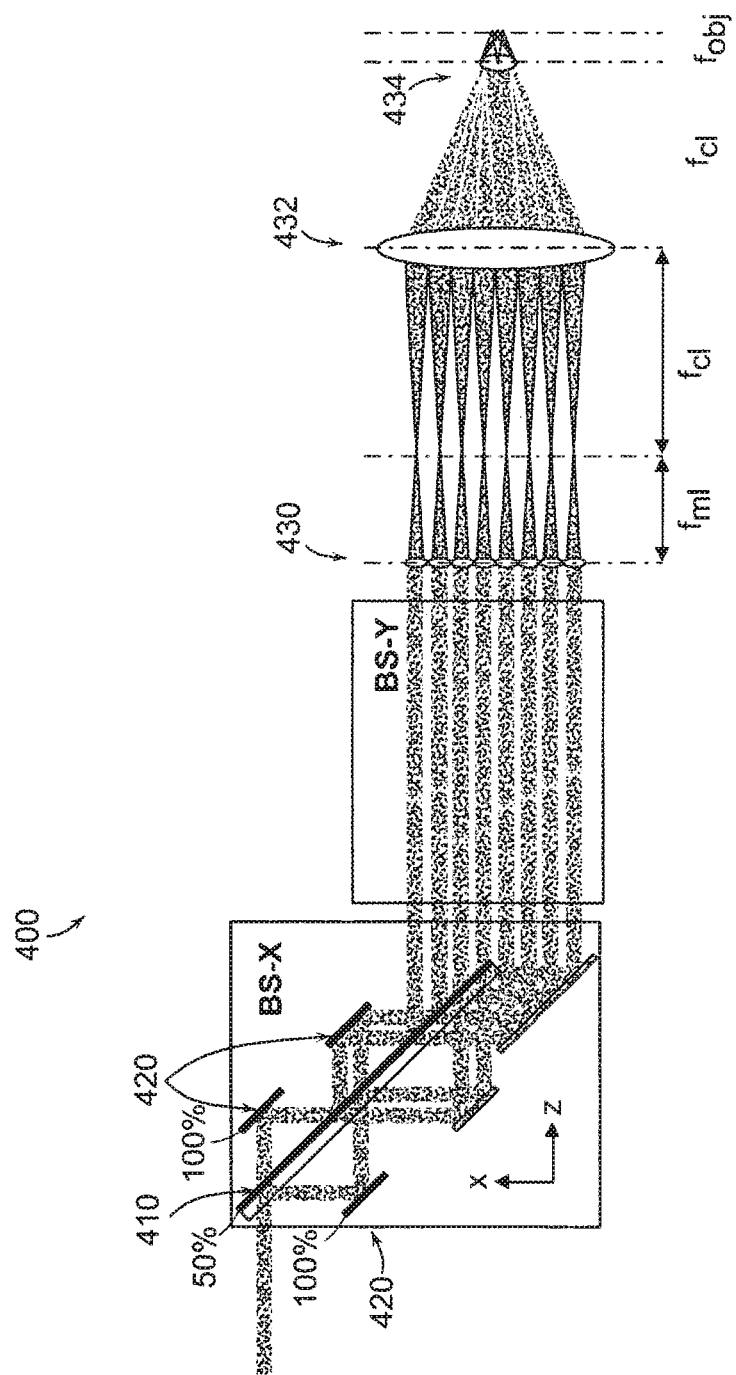
FIG. 13 illustrates a beam splitter configuration used in some embodiments according to the invention.

Referring to FIG. 13, a beam splitter device 400 can be used to create a homogenous intensity profile over a plurality of beamlets. Depending upon its design, the beam splitter splits one beam into 256, 128, 64, 36 or 16 approximately equally powered beams by one or more fully reflective or semitransparent mirrors. In FIGS. 13 50% and 100% indicate the percent reflectance of the mirrors used, where a series of fully reflective mirrors 420 with one longer semitransparent 410 mirror splits the beam in the x-plane (BS-X). By combining two such cubes in series, it is possible to generate a 2D array of beamlets. The internal optics of a second beam-splitting cube for the y-plane (BS-Y), are the same as for x-plane beam splitting cube. The beams are then focused by micro lens 430 (or via other multifocal optics) through lens 432 and objective lens 434 onto the focal plane.

FIGS. 14(*a*)-14(*d*) illustrate additional preferred embodiments for providing multifocal illumination including a micro-lens array 140N from expanded beam 201N in FIG. 14*a* and FIG. 14*b* a diffractive optical element 205N separates beam 201N into a separated plurality of beams which are coupled to focal locations as previously described herein. In FIG. 14*c* a plurality of optical fibers 220N can be used to provide a plurality of beams with lens L1 for delivery to the focal locations or spots. As seen in FIG. 14*d* the fibers 220N can position beams in different directions for smaller or greater focal separation.

In addition to the primary use of this instrument for two photon microscopy, other multi-photon sensing and imaging methods can also be used with the system described herein including:
    2, 3, or more photon excitation microscopy,
    second, third ore more Harmonic Generation microscopy,
    coherent anti Stokes Raman scattering (CARS) microscopy,
    multi photon quantum dot imaging,
    surface plasmon imaging, and
    Stimulated Emission Depletion (STED) microscopy
With the implementation of a confocal pinhole array, shown in FIG. 8, confocal microscopy can be preformed with the same instrument.

FIGS. 15(*a*)-15(*d*) illustrate further preferred embodiments for use with detectors which can be a multi anode PMT or an array of single detectors, connected via optical fiber. The detectors can be PMT's or avalanche photo diodes, or the detector array can be a combined device (like a multi anode PMT), connected via optical fiber, an avalanche photon diode array, a CMOS imaging detector, or a CCD camera in which each pixel or each area of binned pixels is correlated to one focus, or a CCD camera in which more than one pixel or more than one binned pixel area is correlated to one focus. As seen in FIG. 15*a*, the detector 210P can be coupled directly to optical fibers 220P which receive light from lens L1. As shown in FIG. 15*b*, individual detectors 210P can collect at different angles, or as seen in FIGS. 15*c* and 15*d*, a detector array 212P can detect at the same or different angles respectively.

Figure 16:
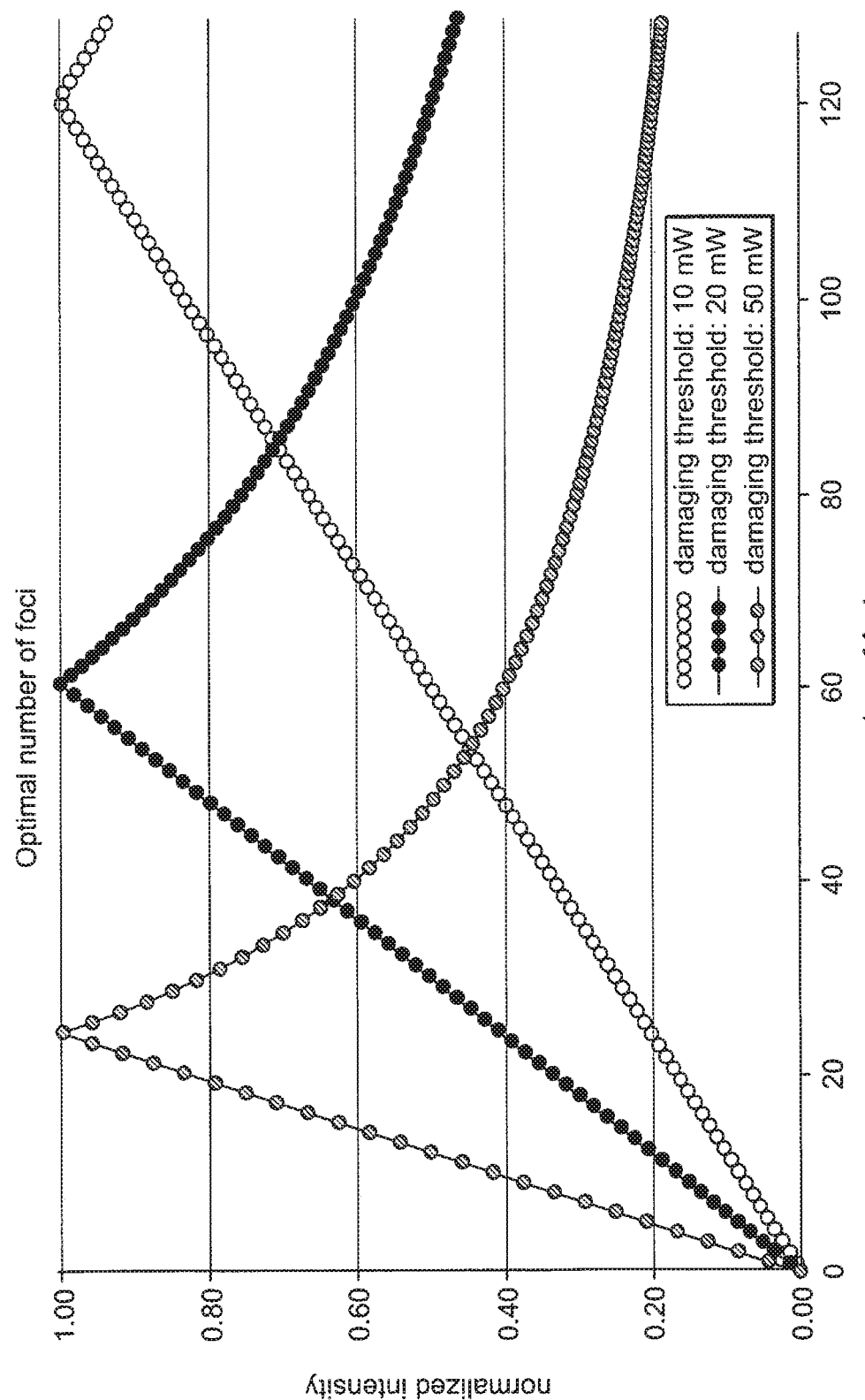
FIG. 16 illustrates determining the optimal number of foci at a certain laser power for samples with different damage thresholds.

Referring to FIG. 16, the optimal number of foci for a two photon excitation process at a certain laser power for samples with different damage thresholds can be determined. The optimal number of foci will depend on (i) the damage threshold, (ii) the quadratic dependency of the two-photon signal to the laser power, and (iii) the limited amount of laser power. In the graph shown in FIG. 16, the laser power is limited to 1.2 W at the sample, while the damage threshold of the sample ranges can be 10 mW, 20 mW and 50 mW. As a result, the optimal number of foci is 120, 60 and 24 respectively. In general, the appropriate power level for two-photon imaging is constrained by two basic boundary conditions: (a) the minimum accepted signal-to-noise ratio determines the minimum power that can be used, whereas (b) the damage threshold of the sample determines the maximum power. In an MMM system, the limited laser power is distributed over a large number of foci. The best signal is obtained when the number of foci is chosen in a manner such that each of the foci delivers a power level just below the damage threshold for the sample. The relationship is illustrated in FIG. 16. It is possible to obtain less signal from the sample as more foci are used, owing to the squared dependence of signal on laser power. A judicious choice of power levels and of number of foci must be made in order to obtain optimal results. Therefore, a preferred method and system provides for a versatile system in which the number of foci can be varied with respect to the sample threshold. The threshold can be different for different penetration depths into the sample and can therefore be adjusted by the attenuator 163B.

Time multiplexed illumination and detection enable MMM microscopy with one detector only, which is gated to the excitation light pulse. In one variation of a multi-photon MMM, the illumination light source is a pulsed laser. In this case, a Ti:Sa Laser with a repetition rate of approx. 80MHz and a pulse width of approx. 100-200 fs as an example. In the standard illumination version of this MMM, all beams carry the same pulse distribution along time. As a consequence, the array of excitation foci in the focal region is formed simultaneously. For image formation, during or after at least one pulse has illuminated the sample, the beam or sample is scanned on both axis perpendicular to the optical plane; here indicated by x≥0.

Figure 17B:
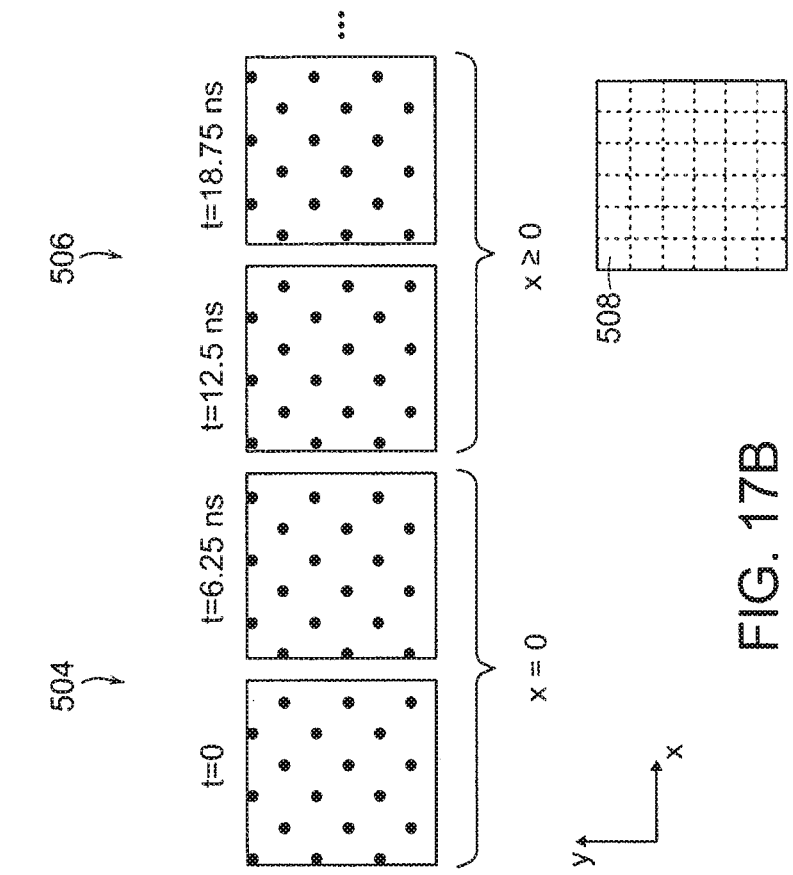
FIGS. 17(a) and (b) illustrate a time multiplexing method.
Figure 17A:
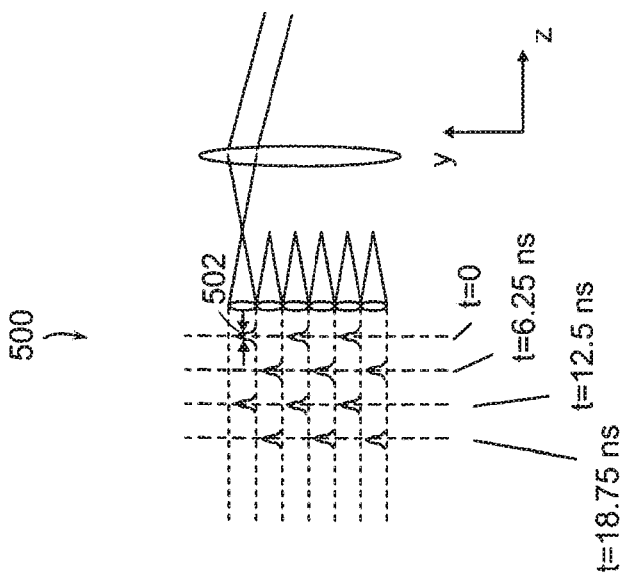

In the example of multiplexed operation 500 shown in FIGS. 17*a* and 17*b* 36 detection elements are collecting light from 18 simultaneously illuminated spots. The delay between the illumination pulses 502 is alternated between foci shown at 504. This configuration can be imagined to be accomplished with more detection channels per simultaneously illuminated foci. For image formation, during or after at least one pulse has illuminated the sample, the beam or sample is scanned on both axes perpendicular to the optical plane; here indicated at 506 by x≥0. Depending on the particular configuration, there are several different advantages. First, the light in non-corresponding detection channels has an additional time delay relative to light from the foci corresponding to the detector channel 508 that is receiving light at a particular time. In fast processes, the resulting signals may not or may minimally overlap and thus be registered to the proper foci directly. In slower processes, where the overlap may be significant, the temporal separation will aid numerical registration and deconvolution algorithms. Furthermore, when the number of detectors matches or exceeds the number of illumination foci, the response in the neighboring non-corresponding detectors can be used to generate additional information about the sample. The temporal delays introduced into the illumination foci mean that this supersampling condition exists even when the number of detectors is the same as the number of foci.

In anther example, alternating excitation foci pattern can be detected by a multichannel detector with smaller number of elements than number of foci.

In cases in which the repetition rate of the laser is lower that in the case of the Ti:Sa laser, a time multiplexed MMM illumination and a detection in a single channel can be used. In this particular case, the repetition rate of the laser is a hundred times lower than in previous examples. In a time multiplexed version, each beam carries a pulse which is temporally separated in regards to pulses of the other beams. In one particular case, they are separated evenly over the time period of one laser repetition, so that at evenly distributed time points, one single foci is illuminated at a time. If a fast detector is correlated with the pulse distribution and capable of detecting each pulse separately during this short time period, an MMM with only one detection element can be used. This detection element has a corresponding detection area to collect light which is generated by each individual foci during its scan. For image formation, during or after at least one pulse cycle has illuminated the sample, the beam or sample is scanned on both axis perpendicular to the optical plane. As a result, optical cross-talk is completely eliminated, as the light from the different foci is excited and detected at different time points. Applications for this case are excitation processes which appear instantly, like scattering effects (such as Second Harmonic Generation (SHG) or Coherent Ramen Anti Stokes scattering (CARS)). This configuration can be used suited for a non-de-scanning configuration. Other repetition and detection rates are possible.

Figure 18A:
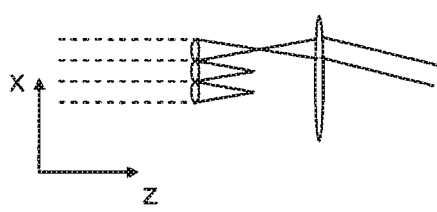
FIGS. 18(a)-(c) illustrate a pixellated detector collection method.
Figure 18B:
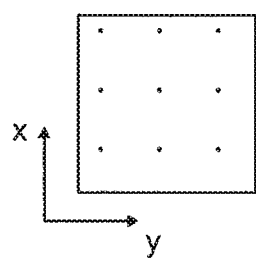
Figure 18C:
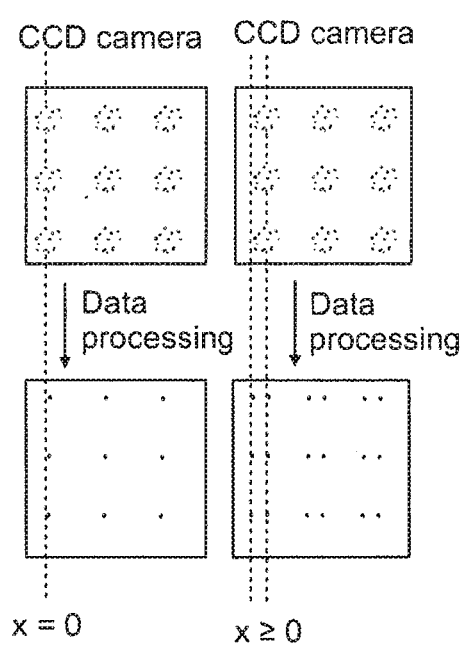

In the case of using a pixellated detector such as a CCD or a CMOS imager, an array of 3×3 beams, FIG. 18a, illuminates the focusing device, forming an array of 3×3 foci (FIG. 18b). As seen in FIG. 18c, the image of the scattering distribution of the foci is imaged by the CCD camera. The wide-field image is accumulated per scanned illumination point. The scattering distribution of each foci can be recorded on many CCD pixels. The illumination or sample can be scanned and the wide-field data can be further processed to form an image or statistical representation from many object points. This configuration can be employed in a non-de-scanning configuration as well.

The above described systems and methods can be used for imaging of all semi-transparent and highly scattering materials; 2D and 3D, and in particular for imaging of human and animal tissue, cells in suspension, plants and other biological material.

The illumination can be achieved with visible light and alternated with the MMM scanning measurement or out of band illumination light can be used and the camera measurement can be taken simultaneously with the MMM measurement. This configuration can be used for large field imaging, sample guided MMM measurements, conventional staining measurements, and online MMM measurement process control, for example, bubble formation monitoring, and laser spot diagnostics.

There is a large variety of fluorescent that can be used with various embodiments of the invention dyes. In general they fall into two families: Dyes that have to be applied to stain the tissue "from the outside" and dyes, that are expressed from animals as proteins. Most commonly used dyes by external staining MitoTracker Red, DAPI, Hoechst 33342, Cy2-IgG, Alexa Fluor 546, Rhodamine 123, Alexa Fluor 488, FITC-IgG, Acridine Orange, Cy3-IgG, Issamine Rhodamine, TexasRed-Phalloidin, TexasRed-IgG, Alexa Fluor 594, Propodium Idonide. Dyes genetically expressed by genetically modified animals: green fluorescent protein (GFP) and other dyes in this family: Enhanced GFP EGFP, Yellow fluorescent protein (YFP), Enhanced YFP. Auto fluorescent imaging does not use a particular dye, but can be used as part of an imaging technique.

Besides confocal microscopy (fluorescent, as well as reflected light confocal), these include all other multi-photon microscopy techniques, such as, 2, 3, or more photon excitation microscopy, Second (SHG), Third (THG) ore more Harmonic Generation microscopy, Coherent Anti Stokes Raman Scattering (CARS) microscopy, multi photon quantum dot imaging, surface plasmon imaging and Stimulated Emission Depletion (STED) Microscopy. These techniques can be used with or without staining methods. The scattering techniques, such as SHG, THG, CARS are developed to be able to image without any staining involved.

Figure 19:
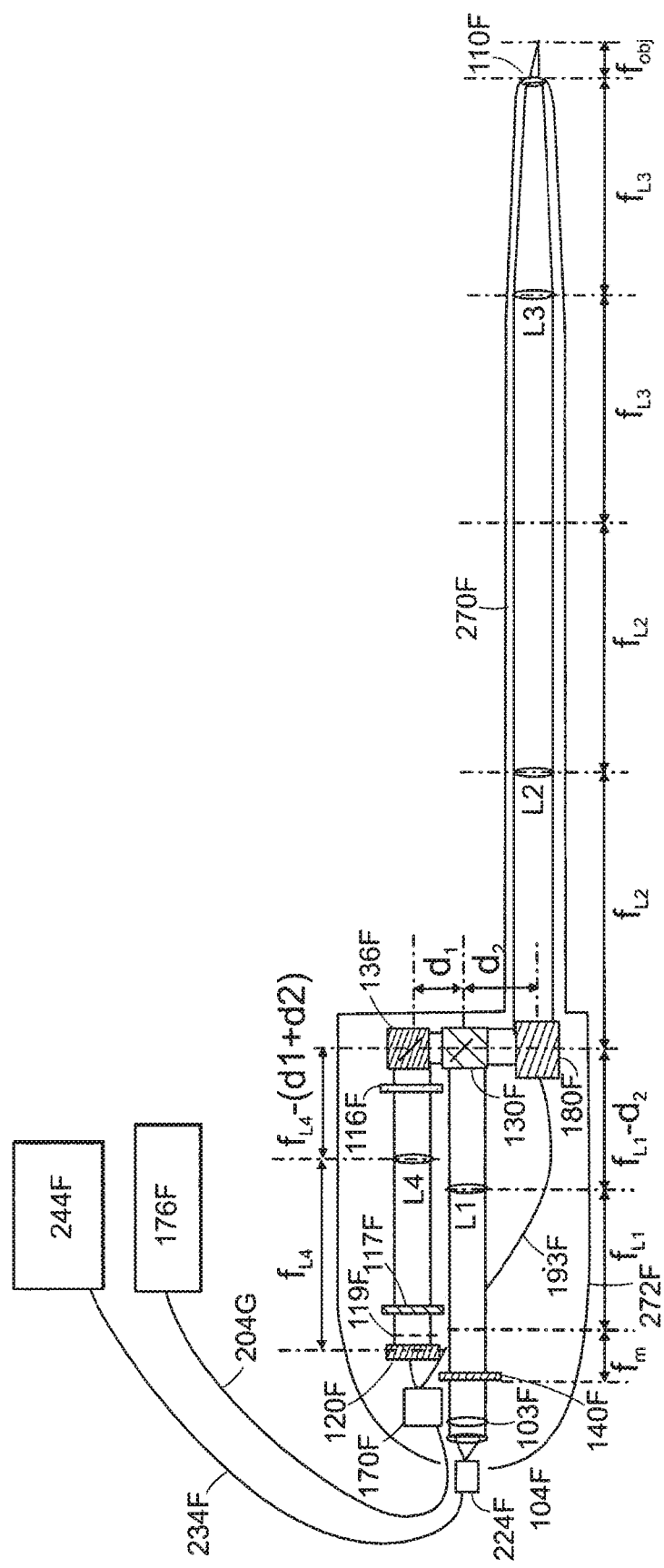
FIG. 19 illustrates an endoscope apparatus according to an embodiment of the invention.

FIG. 19 illustrates a probe or endoscope apparatus according to an embodiment of the invention, having a handle portion 272F and an insertable probe portion 270F, wherein light delivered from a light source 244F (which can be a laser or other light source) is delivered through an optical wave guide 234F (such as, for example, optical fiber, hollow fiber optics, photonic band gap fiber, or other wave guide) to an optical connector 224F (such as, for example, a pigtail), whereupon an expanded beam 104F passes through a lens or optionally through lens pair telescope 103F and then through a micro lens array, or other optical device that creates a plurality of optical pathways, 140F. The illumination path can then pass through lens L1, dichroic 130F and lenses L2 and L3 onto the rear aperture of the objective 110F The beam is made to scan by scanner 180F which can tilt in the x and/or y directions, and the return fluorescent signal is directed by dichroic 130F and reflector 136F, optionally an IR block filter 116F through lens L4 and optionally a band pass filter 117F onto a multi-anode PMT detector 120F. In an alternative embodiment, a plurality of confocal pinholes 119F are placed in front of the plurality of detectors cells. The detector 120F can be connected to a controller 170F and to an image processing computer 176F. The scanner 180F can also be controllably connected by electrical connector 193F to a controller 170F and/or computer 176F. In FIG. 19, the proportions of the endoscope have relationship to the focal distances of the micro lens array, fm, the lenses L1-L4, being $f_{L1}$, $f_{L2}$, $f_{L3}$ and $f_{L4}$, offset distances $d_1$ and $d_2$, and the size will be related to the relative size of the various elements.

Referring to FIGS. 20(a)-(b) through FIGS. 24(a)-(b), in which common elements share the same numbering between figures, the active area, relative proximate orientation of active detector elements (such as, for example, the active area of multiple anode photomultiplier tube detector elements), and the distance of the foci and the intermediate optics have an important relationship to the effectiveness of detecting scattered light from one or more light spots in a sample specimen, as explained in the following.

Figure 20B:
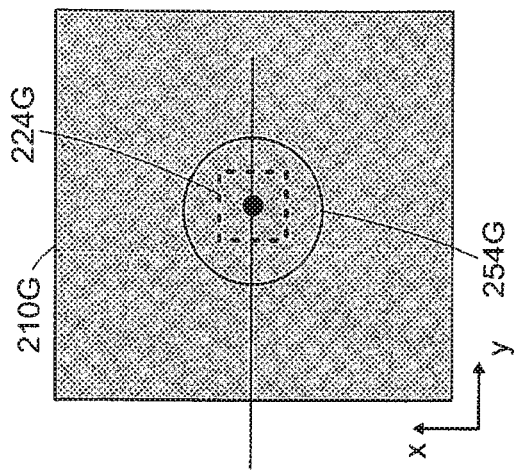
FIGS. 20(a) and (b) illustrates scattered light detection with one PMT and one excitation focus according to an embodiment of the invention.
Figure 20A:
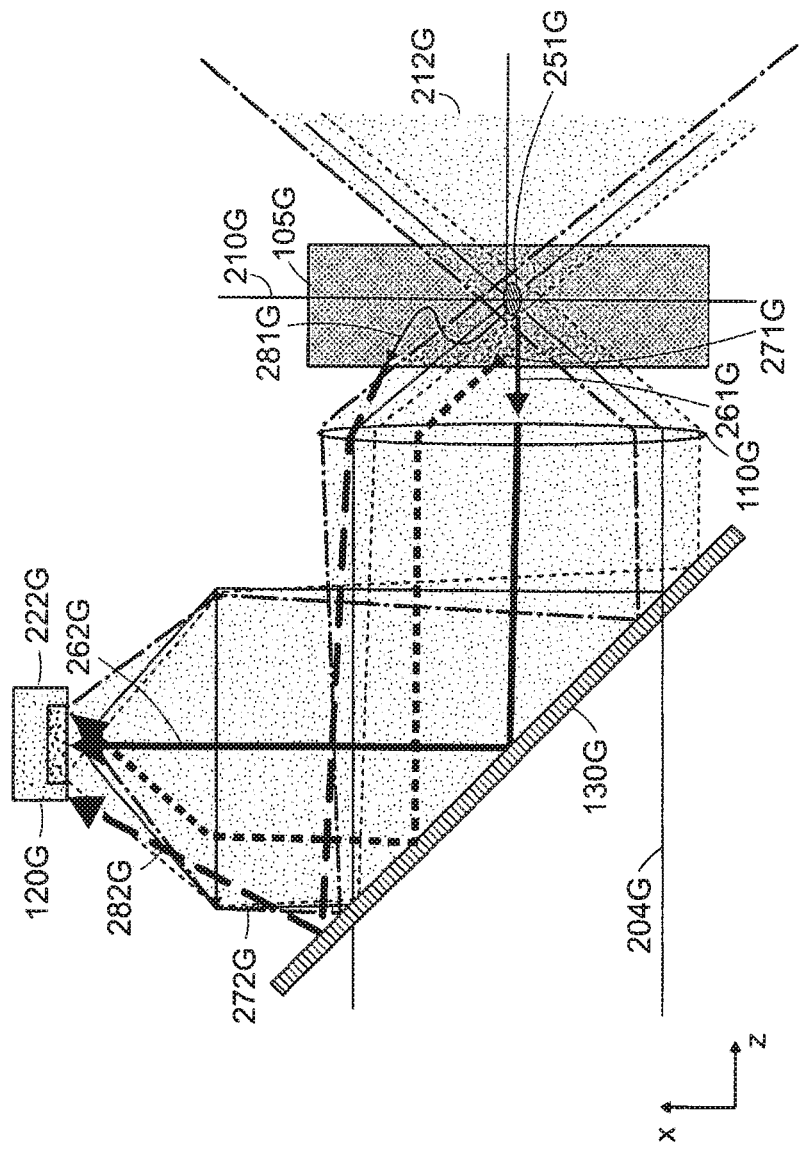

FIG. 20(a) depicts one PMT and one excitation focus, and the direction of scattered light with respect to the detection light cone of the active detection area will control whether or not the photon will be detected. FIG. 20(a) provides an illustration of how the size of the active detection area relates to scattered light detection from a spot created by multi photon excitation, as follows: An illumination light beam 204G coming from the left (parallel solid lines), generates a multi photon excitation light spot 251G (so-called excitation point spread function) in the sample 105G, in which the structure causes a multi-photon excitation process. Within this 3D sample region, light is generated according to the multi-photon excitation principle and scattered on its path (such as, for example, an auto-fluorescent tissue sample). The potential detection path is illustrated by the very thin bounding lines enclosing the stippled shaded region, which are geometrically determined by the side boundaries of the active PMT detection area 222G of the detector 120G. In this configuration, all the photons that propagate within the detection cone, indicated by the shaded region, and that travel in the direction of the detector 120G, are collected in the active detection area 222G. Photons that propagate in the opposite direction, or that are scattered outside of the detection cone defined by the optics and thus outside of the active detection area 222G of the detector 120G, are not detected. This is depicted in FIG. 20(b) as well, where the detection area 224G (dashed box) in the sample focal plane 210G corresponds to the active detection area 222G, while a potential scattering region 254G (circle) extends beyond the confines of the detection area 224G. Three examples of photon path are shown in FIG. 20(a), as follows: (1) An unscattered photon 261G, traveling in the opposite direction to the incident light beam follows a path 262G (solid line), which path 262G lies within the detection light cone and travels towards the active detector area 222G and is thus collected; (2) a first scattered photon 271G that is scattered within the detection cone follows a path 272G (short-dash line) and travels in the direction of the active detector area 222G and is thus detected; and (3) a second scattered photon 281G that follows a path 282G (long-dash line) which travels generally in the direction of the detector but does not fall into the detection light cone of the active PMT detection area 222G, and thus it is not detected. Light generated in the spot 251G is detected by the same objective lens 110G. It can as well be detected by an opposing objective lens and collected by a detector associated with the detection area to the light spot at the opposing side. Then also photons in the detection cone of the second, opposing lens, traveling towards the direction of the incident light into the opposing detector, are collected.

Referring to FIG. 21(a), when scattered light from one excitation foci 251G (single excitation point spread function (PSF)) is detected in a setup with two PMT elements 120G, 124G, the gap 232G (also marked as "g") between the active detection area 222G of detector element 120G and the active area of the second element 124G will correspond to the gap 236G in FIG. 21(b) between two detection areas 224G, 226G in the sample focal plane. If the scattering region 254G around the excitation foci 251G extends into the detection area 226G, then the photon 281G that is scattered beyond the detection cone for active detector area 222G of detector 120G can follow photon path 282G into the adjacent detector 124G.

Scattered light detection from a spot 251G created by multi photon excitation, detected by two large area detectors 120G, 124G, positioned next to each other, are separated by a distance: In this case, the unscattered photon 261G and the first scattered photon 271G are still collected by the active detection area 222G of the first detector 120G. The second scattered photon 281G is not lost, but is collected by the second detector 124G. This effect of light being scattered into detectors other than the optically conjugated detectors is termed "optical cross talk".

FIG. 22(a) illustrates scattered light detection with two PMTs 120G, 124G and two excitation foci 251G, 252G, where again the issue of "optical cross talk" is relevant. Here a second illumination light path 206G at an angle $\Psi_1$ with respect to the first illumination light path 204G, creates a second focus 252G (excitation PSF) at a distance δ from the illumination light spot 251G. In FIG. 22(a), only one, unscattered photon 291G is illustrated in order to simplify the drawing. This photon 291G originating from 252G follows optical path 292G into detector 124G (although the illustration includes a collimating lens between the reflector and the detector and a refraction in path 272G by said lens is depicted, owing to constraints in the size of the drawing and to illustrate better the features emphasized here as aspects of an embodiment of the invention no refraction in the paths of 282G and 292G is depicted in this illustration). Light originating from the second light spot 252G will be collected by the second detector 124G, but also by the first detector 120G as well because photons from the second light spot 252G are similarly scattered as photons from the first light spot 251G. FIG. 22(b) illustrates this by showing scattering area 256G overlapping both the detection areas 226G and 224G (again the gap 236G between the detection areas in the focal plane will correspond with the gap 232G between the boundaries of the active detector regions). As a result, scattered light from light spot 252G is falling in the detection cone of first detector 120G and will be detected by that detector 120G (i.e., optical crosstalk). With increased scattering of photons in the sample, the optical crosstalk increases. Samples with a low mean free path length (MFP) for photons will induce photons to scatter more (scattering more times at equal traveling lengths); thus, samples with low photon MFP will induce higher optical cross talk. In addition, increasing the imaging depth will raises the probability that a photon will be scattered on its way through the sample to the detector, because the traveling length in the high scattering media is longer. Because light with longer wavelength is scattered significantly less, applications with relatively longer detection wavelengths have often been preferred, in order to reduce the effect of optical cross talk. However, preferred embodiments of the invention provide methods for reducing optical cross talk without having to shift to longer wavelengths.

Figure 23B:
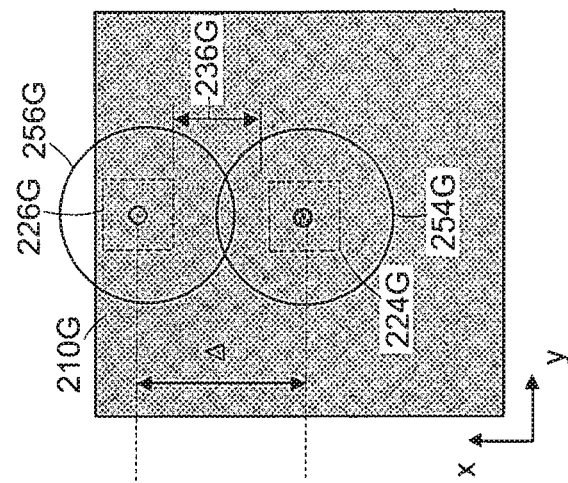
FIGS. 23(a) and (b) illustrates reducing optical cross talk by increasing the distances between the excitation foci and distances between the detection elements.
Figure 23A:
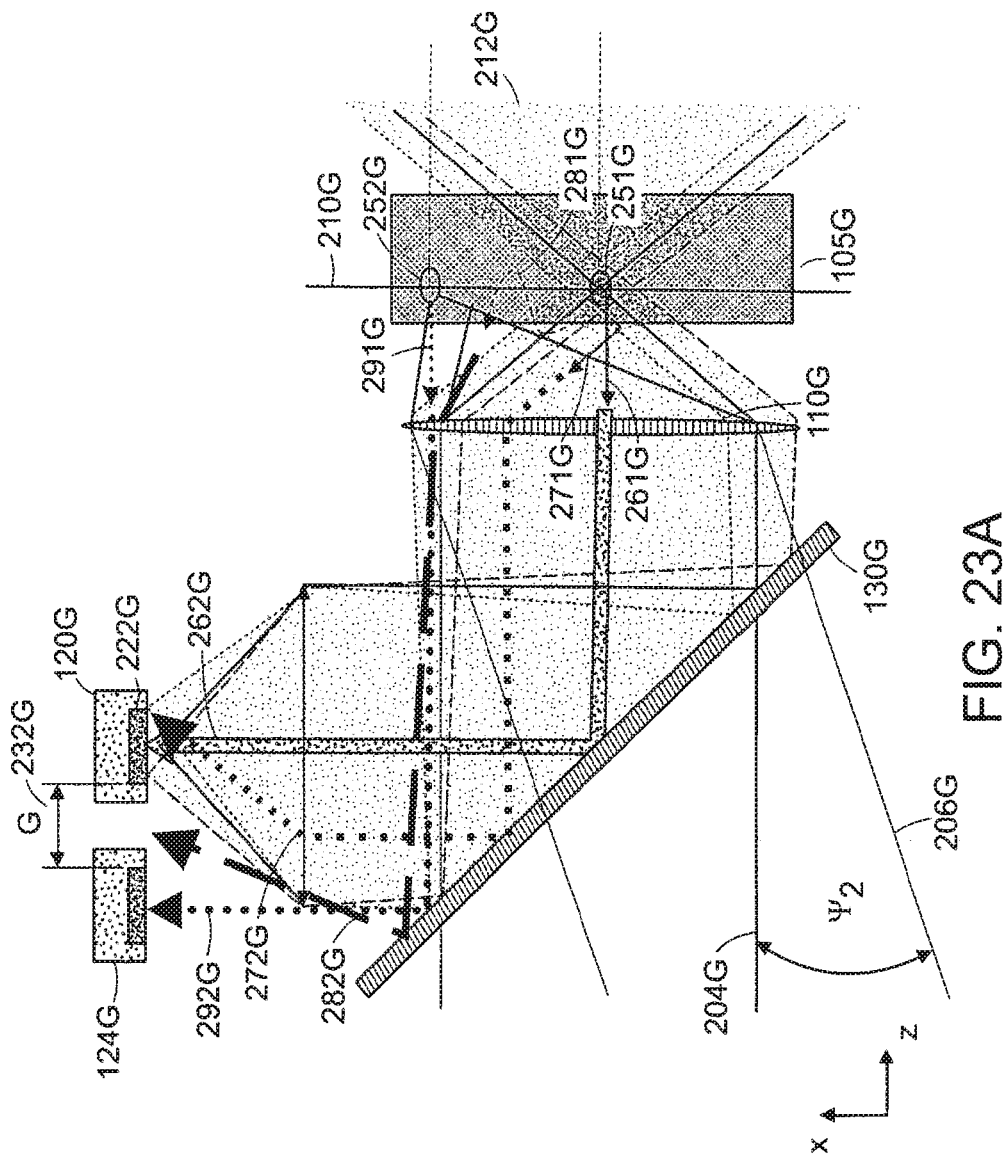

Referring to FIG. 23(a), for instance, the invention provides for reducing optical cross talk by increasing the gap distance between the excitation foci, this gap distance depicted as δ, and simultaneously increasing the gap 232G between the active detection areas in the detection elements. In this case, the second illumination light path 206G is separated further by an angle $\Psi_2 > \Psi_1$ from the first light path 204G, generating an illumination light spot 252G in a location that is larger distance Δ>δ from the illumination light spot 251G. The detectors 120G, 124G are also separated from each other by increasing gap 232G between the active detector areas to a value "G", where G>g, such that the second unscattered photon path 282G no longer falls into the second detector 124G. FIG. 23(b), illustrates this by showing no overlap between scattering regions 254G, 256G and the neighboring detection areas 226G, 224G, respectively. With this configuration, optical cross talk is reduced because fewer photons end up in the "wrong" channel; however, some scattered photons will not be detected because their paths will pass between the active detection areas of more widely separated detectors. Thus, detection light (signal) is lost.

Referring to FIG. 24(a), a preferred embodiment of the invention provides for reducing optical cross talk without inducing signal loss, by increasing the distance between the excitation foci and simultaneously increasing the active detection area of the detector elements. By separating the foci and the associated detectors, the optical cross talk is reduced. By increasing the active area of the detectors, most scattered photons are collected. In FIG. 24(a) this is depicted by the second scattered photon path 282G being collected by its corresponding detector 120G. FIG. 24(b) shows the expanded detection areas 226G can encompass the scattering In a further embodiment, changing the optical configuration of the apertures and focal length of the lenses in the optical system can create the same effect. Changing the aperture and the focal length of the micro lens array, increasing the area of the scan mirror, changing the aperture and the focal length of the lenses L1, L2, L3 and L4 has a similar effect of reducing cross talk without loss of signal. An example case is presented in tabular format in FIG. W-22(a)-(e).

The optical configurations for two alternative embodiments of the invention, Example A and Example B, are presented in FIGS. 25(a)-(e). FIG. 25(a) lists the objective lens specifications, which are the same for both Examples A and B (i.e., Olympus, 180 mm tube lens, XLUMPLFL 20× magnification objective; water immersion; 0.95 numerical aperture; 17.1 mm back aperture; 2 mm working distance; 9 mm focal length; 22 mm field number; and 1.1 mm corrected field).

FIGS. 25(b)-(c) list the details of the illumination path. A different micro lens array is described for each embodiment, but in both the micro lenses are square shaped.

In Example A, the side aperture pitch of each micro lens is 1.06 mm and the diagonal is about 1.5 mm. For the entire array in Example A the 8 lenses per side create a side aperture of 8.48 mm and a diagonal aperture across the array of 11.99 mm. The focal distance of each micro lens is 17 mm in Example A. In the embodiment of Example B, the aperture or pitch of each micro lens in the array is 1.9 mm and its focal distance is 25 mm.

The focal lengths of the lenses L1 and L4 are 50 mm and 103.77 mm, respectively, in Example A, while in Example B they are 40 mm and 46.32 mm, respectively. When standard optical components are used, they can approximate components with a focal distance of 100 mm and 45 mm for L4 in the configurations A and B, respectively. In both the embodiments of Example A and B, the focal lengths of lenses L3 and L4 are 30 mm and 125 mm, respectively. The diameter of illumination of the back aperture of the objective lens for both Examples A and B remains approximately constant at 13.0 mm and 12.7 mm, respectively. This results in an 'under-illumination' of the back-aperture of the objective lens which has a back aperture of 17.1 mm in diameter. This is desirable, so an optimal (maximal) employment of the illumination light power is warranted.

As listed in FIG. 25(d), the two embodiments, Example A and B, achieve different distances between excitation foci in the optical plane: Example A has a foci distance of 46 microns, whereas Example B has a foci distance of 103 microns. The total optical field, listed below the foci distance, results from the fact that in this particular case, an 8×8 configuration of foci is chosen. It has a square side of 366 microns for configuration A and 821 microns for configuration B, when the foci are scanned. FIG. 25(e) lists the details of the detection path for each example. These alternative examples, A and B, can be created according to the layouts of either FIG. 7 or FIG. 8, according to embodiments of the invention. In both cases the size of the MAPMT can remain constant at about 2 mm×2 mm. Employing a MAPMT with larger detection elements can increase the detection efficiency.

Figure 26B:
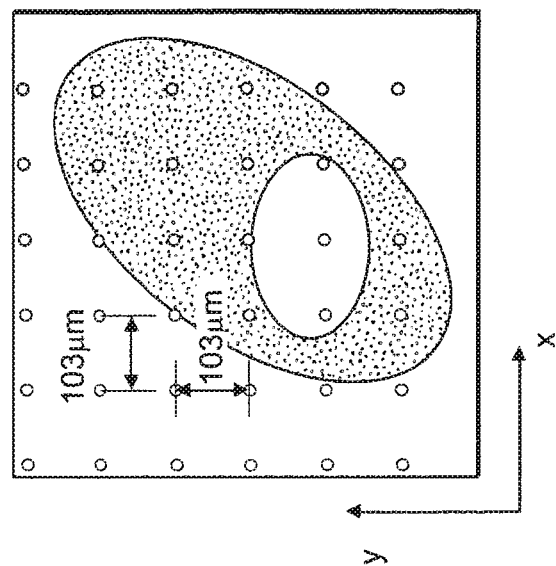
FIGS. 26(a)-(b) illustrates the different conjugated areas of detection from each channel of the multi anode PMT in the conjugated image plane for configuration A and B from FIG. 22(a)-(e).
Figure 26A:
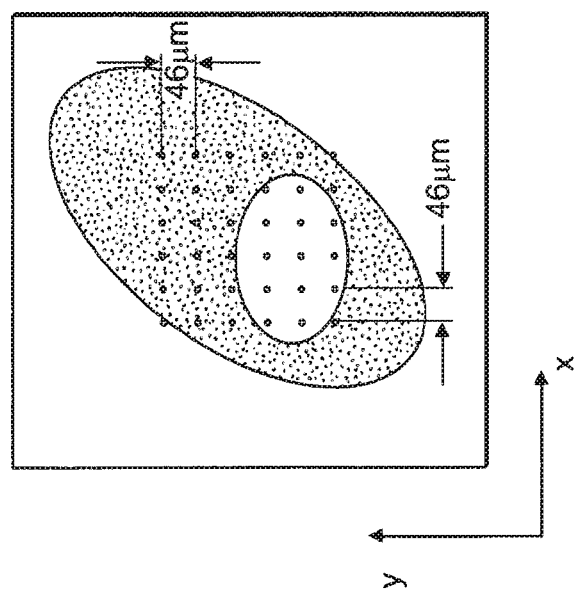

FIGS. 26(a) and (b) illustrate the foci distribution in the focal plane of the objective lens for the embodiment Examples A and B, respectively. The conjugated detection area of each channel of the multi anode PMT is by a factor of 5 larger in the Example B than in Example A.

The optimal distance between the foci is influenced by three factors: (1) the optimal number of foci that are needed to generate as much light as possible (this number can be distinguished in accordance with the graph in FIG. 16; (2) the corrected field of the focusing device, such as an objective lens (the larger the corrected field, the further the foci can be separated from each other and the more the optical cross talk can be reduced); and (3) the numerical aperture (NA) of the objective lens for high resolution imaging (the larger the numerical aperture of the objective lens, the more photons can be collected and the better the images are). Nevertheless, there is a compromise between the NA of the lens and its effective field of view. Therefore, the objective lens used in a most preferred embodiment of the invention has a large NA of around 1.0 or greater and is capable of imaging a large effective field of view, preferably of approximately 1-6 mm.

At a fixed number of foci, a large field objective provides an advantage for certain embodiments of the invention, because the foci can be further separated. An objective lens with large field of view enables large separation of foci and thus reduces optical crosstalk. In FIG. 26(c) and (d) two objective lenses with different fields of view are shown, 600 micron objective field versus 6000 micron objective field, respectively. The conjugated detection area of each channel of the multi anode PMT associated with the focal plane within this field of view is a factor of 100 larger in the objective of FIG. 26(c) versus FIG. 26(d). Commercially available objective lenses with a large numerical aperture (NA) of around and above 1 usually have a field of view for which they are corrected between (100×objectives) around 200 mm and (20×objectives) 1000 mm. With the Olympus XLUMPLFL 20X water immersion objective mentioned above and used in embodiment Examples A and B, when an array of 8×8 foci is employed, the optimal distance between the foci is 111.11 microns and the total field imaged is approximately 1000 microns.

In the embodiments shown in FIGS. 7 and 8, the active detection area of the different detector channels in the MAPMT is approx. 2 mm and limited by the commercially available MAPMT devices. If this area is increases, the optical cross talk and the collection light efficiency is increased.

Figure 27A:
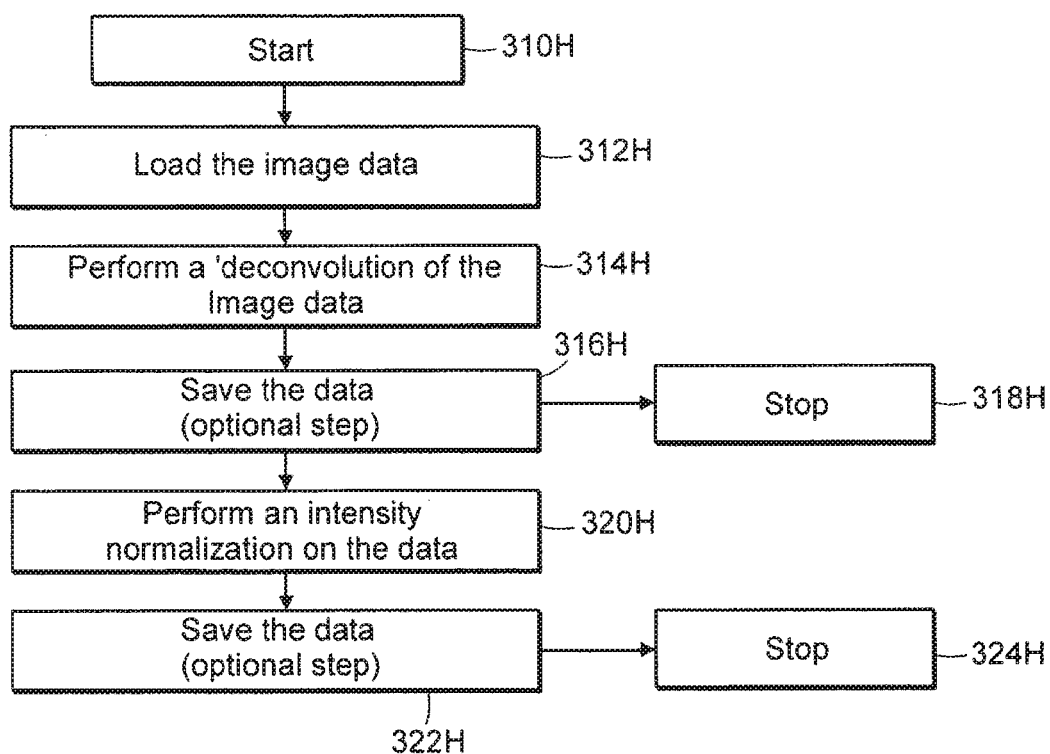

One embodiment of a method for data post-processing according to the invention is illustrated in FIG. 27(a) and provides for data post-processing starting at a step 310H. Step 310H can include initiating a computer program and/or software application automatically as part of a data acquisition step in a computer that is connected directly to the imaging apparatus and/or can include a series of human-supervised data-processing steps. The data processing can be automatically intiated by the computer and proceed entirely automatically according to a data-processing control software application and/or the program may proceed semi-automatically with opportunities for human supervision and intervention in one or more of the data processing steps. An embodiment of the data-processing method follows the start step 310H with a next step to load the image data 312H. This can include accessing raw data and metadata from storage devices, where metadata (data about the data) includes, inter alia and without limitation: foci number, pixel dimensions; pixel spacing; channels; instrument parameters (including, without limitation, optics, objective, illumination, wavelengths, beam-splitting, phasing, polarity, light pumping, pulse compression, chirping, upconversion, dispersion, diffraction, source-light properties, source light stability, source attenuation, reference scanning, micro lens configuration and properties, focal lengths, filter types and positioning, detection configuration, detector type, detector active area, detector sensitivity and stability, and other detector specifications and properties, inter alia); sample properties and sample information, such as, for example, for biological samples (including biological and non-biological information, such as, for example, tissue type, specimen type, size, weight, source, storage, tracking, scattering properties, stain/dye type, specimen history, and other physical properties of the specimen) or sample properties and sample information for chemical and/or physical material samples; and scanner data, including, without limitation, scanning type, scanning mode, scan method, tracking, frequency, certainty, precision, scan stability, resolution and other information about the scanning. Data can be stored as XML, text, binary or in any fashion, in electronic form and/or in retrievable and scannable physical formats. In one preferred embodiment of the data post-processing method, the next step 314H is deconvolution of the image data, which deconvolution is described further below. Following this, the data can be saved in an optional step 316H, whereupon the post-processing can optionally be stopped 318H. An embodiment also allows the processing to continue to a next step 320H that comprises performing an intensity normalization on the data, which normalization steps are described in more detail below, then optionally saving the data (step 322H), and stopping the data processing sequence (step 324H).

Figure 27B:
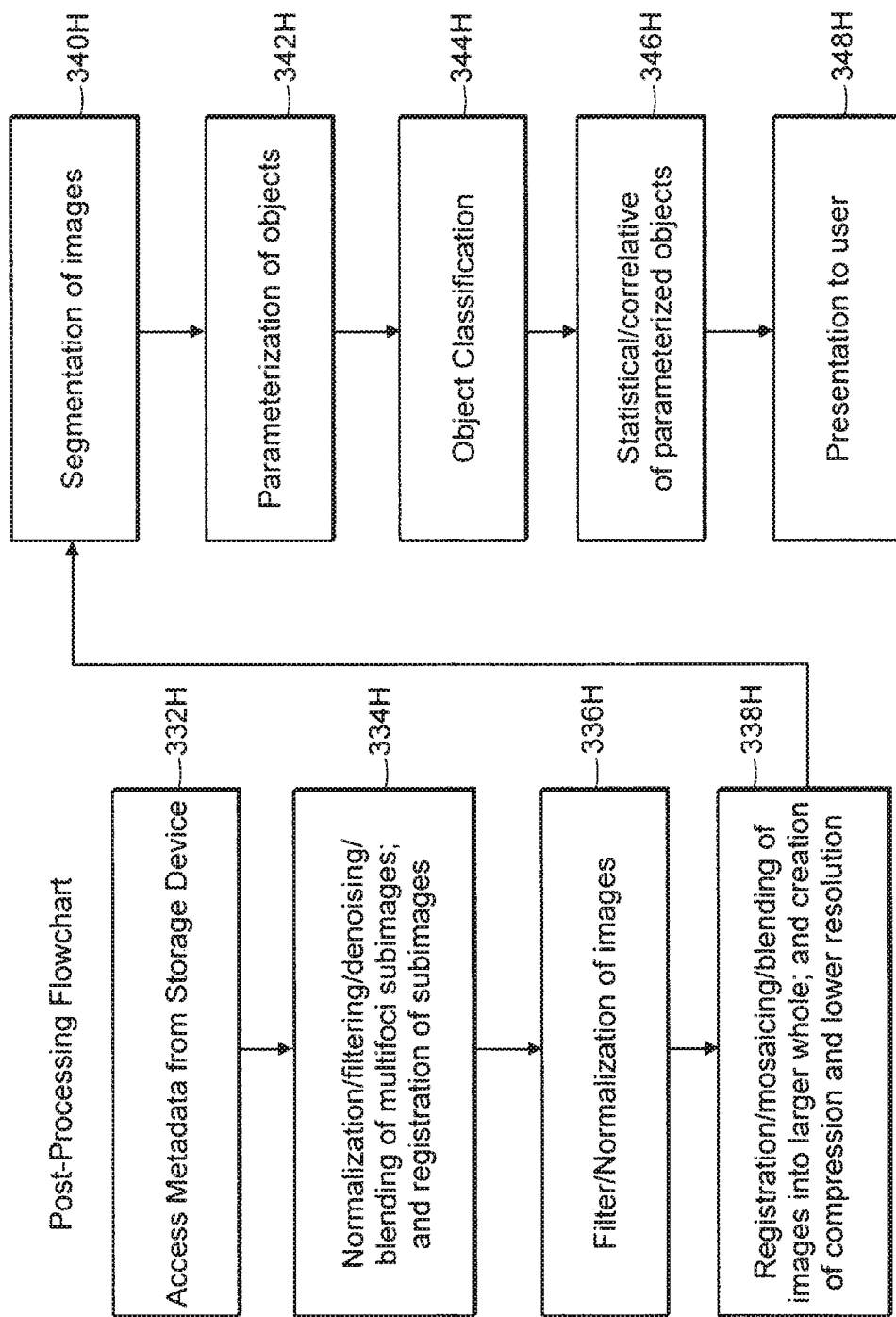

Referring to FIG. 27(b), another embodiment of the invention provides for additional and/or alternative method(s) for data post-processing, In one embodiment, the processing Alternatively, an embodiment of the method The post-processing steps can include a number of substeps. Step 332H can include accessing metadata from a storage device, including here by reference all the description of possible metadata described above for the steps illustrated in FIG. 27(a). Step 334H can include normalizing, filtering (de-noising), and blending6 (integrating) of multifoci subimages, and further can include registering subimages into a single image. Step 336H can include filtering and normalizing images produced from corrected subimages. Step 338H can include registering, building mosaics, and blending sets of corrected images into a larger whole. Also, optionally, at this step 338H, an embodiment of the method of the invention provides for creating lower resolution images of the larger image to facilitate access, as well as images from different perspectives (such as, image views taken of the xy-, xz-, and/or yz-planes) and creating data-compressed versions of the data and/or results (e.g., JPEG, wavelet compression, inter alia without limitation). Step 340H can include segmenting images into objects, which segmentation step can either be manual, automated or a combination of both. Step 342H can include parameterizing the objects, samples or specimens (such as, for example, size, shape, spectral signature). Step 344H can include classifying objects into higher order structures/features (e.g. material stress or cracks, vasculature, nuclei, cell boundaries, extra-cellular matrix, and location, inter alia, without limitation). Step 346H can include statistically analyzing parameterized objects (such as, for example, by correlation methods, principal component analysis, hierarchical clustering, SVMs, neural net classification, and/or other methods). Step 332H can include presenting results to one or more persons on one or more local or distant display devices (examples include: 3D/2D images, annotated images, histograms, cluster plots, overlay images, and color coded images, inter alia).

The post-processing steps can include a number of substeps, including, among other steps those illustrated in FIG. 27(b), without limitation:

i) after data access 332H normalizing, filtering (de-noising), blending (integrating) of multifoci subimages 334H;

ii) Registering subimages into a single image;

iii) Filtering and normalizing images produced from corrected subimages 336H;

iv) Registering, building mosaics, and blending sets of corrected images into a larger whole 338H;

v) Optionally, at this stage, lower resolution images can be created of the larger image to facilitate access, as well as images from different perspectives (xy, xz, yz).

vi) Data-compressed versions (e.g., JPEG, wavelet compression, inter alia without limitation) can be produced;

vii) Segmenting images into objects 340H This segmentation can either be manual, automated or a combination of both.

viii) Parameterizing the objects 342H (for instance, size, shape, spectral signature).

ix) Classifying objects into higher order structures/features 344H (e.g. material stress or cracks, vasculature, nuclei, cell boundaries, extra-cellular matrix, and location, inter alia, without limitation)

x) Statistically analyzing parameterized objects 346H (e.g., by correlation or other methods).

xi) Presenting results to user on display device 348H (examples include: 3D/2D images, annotated images, histograms, cluster plots, overlay images, and color coded images).

Figure 28B:
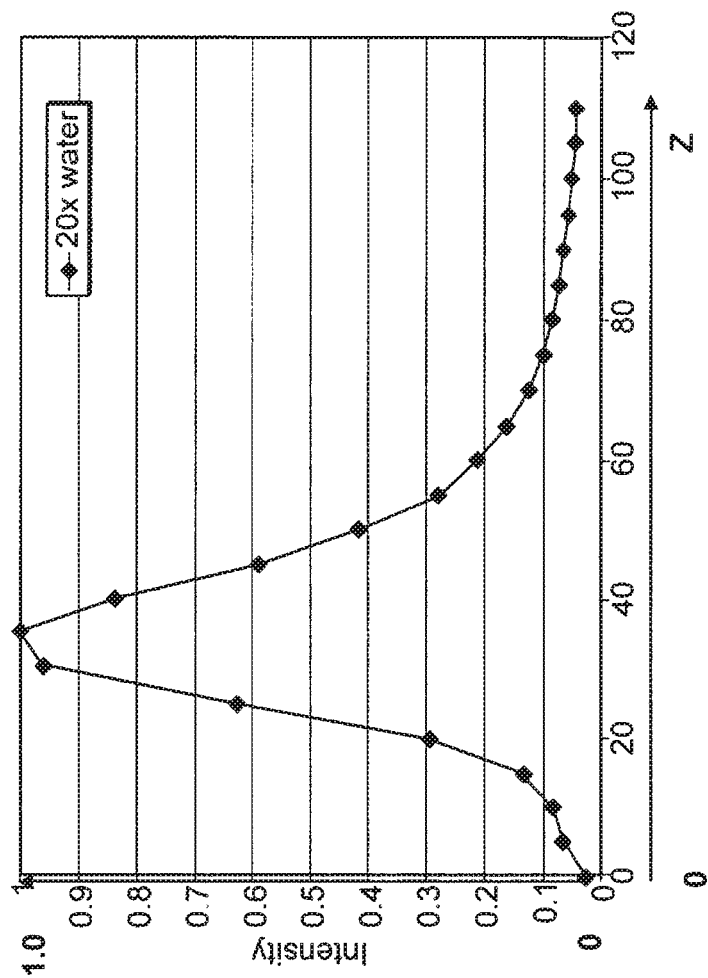
FIGS. 28(a) and (b) illustrate a normalization method.
Figure 28A:
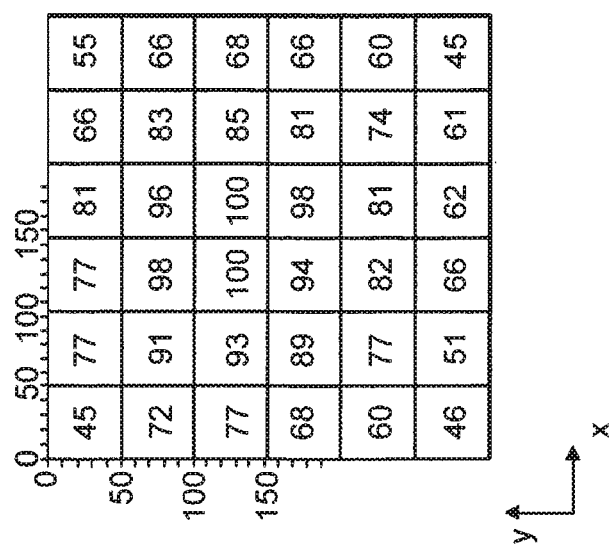
Figure 30A:
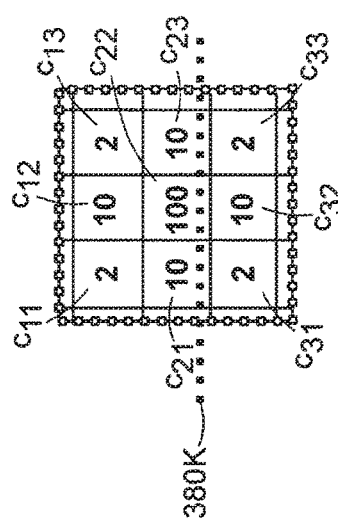
FIGS. 30(a)-(d) illustrate further details for a linear deconvolution process I: Signal distribution in multi channel detector
Figure 30D:
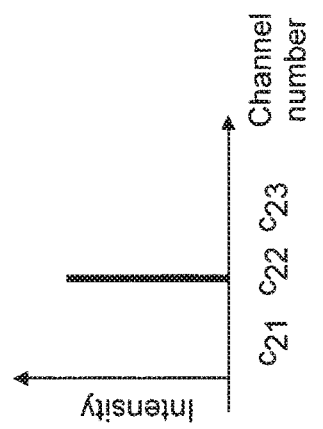
Figure 30C:
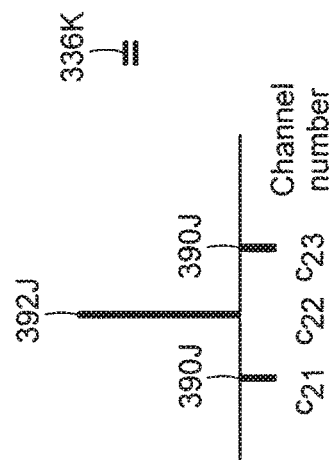
Figure 30B:
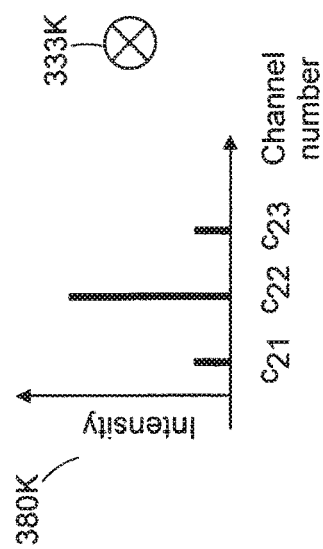

FIGS. 28(a) and(b) relate to image normalization. The multi foci power map of the MMM when a micro lens array is implemented. The numbers resemble the power in each foci in the sample. Due to the Gaussian beam profile in an example, 51.2 mW are inhomogeneously spread over the 36 foci. 24.1 mW contribute to the foci lying beyond the 6×6 foci matrix and are thus lost.

The normalized signal distribution resembles the normalized power map squared and shows an intensity drop of 45% toward the corner PMTs in respect to the center PMTs. The laser power was attenuated to 75.3 mW in the sample and can reach a maximal value of approx. 645 mW, resembling a power of approx. 15 mW for the center foci in the sample. Measured intensity profile can be generated by imaging a homogeneously distributed fluorescent dye under a cover slip. The intensity measurement is not only mapped by the power/intensity distribution of the foci, but also by the sensitivity of the detector array. As a result it resembles the "true" measured intensity distribution. The image consists of 192×192 pixels and was generated by an array of 6×6 foci which were scanned across a uniform fluorescent dye sample. 2D xy image normalization is carried out in different ways:

Case 1: The normalized inverse of this intensity image (from a uniform fluorescent dye) is multiplied with the yx images taken of the sample. The resulting images are then displayed and saved as a normalized image.

Case 2: A large number of images from a sample at various positions (and thus with a random underlying intensity structure) is averaged. This image is then inversed and normalized. This image is multiplied with the original data is then displayed and saved as a normalized image.

Case 3: A simplified image is generated which consists of 36 sub-images (generated by the 6×6 foci). Each of the sub-images carries the average intensity generated by the specific foci. For example, all 32×32 pixels in the top left sub image carry the same number; 45. The image is then inversed and normalized. This image multiplied with the original data is then displayed and saved as a normalized image. An image can be generated either from the intensity image generated by the process of case 1 (fluorescent image) or case 2 (over many images averaged). 3D xyz image normalization is carried out in a similar fashion as in case 2 of the xy image normalization. A z-intensity profile (an example is FIG. 28b) is generated by averaging the intensity signal the xy planes form different positions in z. As the penetration depth increases, the average intensity decreases along the z-axis. In order to get a good average intensity for the z-intensity profile, images from a sample at various positions (and thus with a random underlying intensity structure) are averaged. This z-intensity profile is then inversed and normalized. Each image plane is then multiplied with the according normalization number generated by this process.

A method for multifocal multiphoton imaging of a specimen in accordance with a preferred embodiment of the present invention:

(0) Start
(1) Sample pre processing (optional)
(2) place the sample in the region of focus of the focusing device (objective lens)
(3) determine imaging parameters
(4) set imaging parameters
(5) image
(6) Process images for feedback purposes (optional)
(7) display the images (optional)
(8) save the data
(9) process the data (optional)
(10) save the processed data (optional)
(11) display the processed data (optional)

Concerning the order of the steps, (1) and (2) can be switched: (4), (5) and (6) can be switched.

In more detail these are
(1) Sample pre processing
  Apply tissue staining
  Apply optical clearing agents
(2) place the sample in the region of focus of the focusing device (objective lens):
  Determine desired sample region
  Place the sample in the region of focus of the focusing device (objective lens):
or
  Place the region of focus of the focusing device (objective lens) on to the sample
(3) determine imaging parameters
Determine imaging parameters by which include variable or multiple values for each of the parameters
  measurements performed manually or in an automated fashion outside or within the imaging procedure comprising
    the region of interest
      Sample shape
      Sample margins
      Emission intensity
      Emission wavelength
      Emission polarization
      . . . *
    sample
      type
      photons mean free path
      power threshold
      sample fixation
      sample labeling
      . . .*
    illumination
    detector
    . . . *
    The imaging parameters comprise
      illumination wavelength
      illumination power
      illumination polarization
      scanning speed
      maximal penetration depth
      sampling
      . . . *
(4) set imaging parameters
A computer program is fed with the imaging potentially dynamically adjustable (including feedback from the measurement) parameters and controls the imaging procedure.
(5) image
Point measurement.
1D scan: Collect data from a region of interest
2D scan:
  Image a 2D region of interest by scanning the foci in parallel across the imaging plane (XY)
  the 2D scanning starts for example at a corner of an area and is then scanned in a raster until the area is covered according to the imaging parameters (current implementation)
  or it can be scanned in any other way (even random scan is allowed), as long as the area is covered according to the imaging parameters and the position of the foci is known by the signal sent or received by the scanner.
  A key consideration for the improvement in the measurement is that the detector measures the sample for each scanning position, without overlap.
3D scan:
  move the focusing device (objective lens) in reference to the sample along the optical axis (Z) and repeat the 2D imaging process. Either, the focusing device (objective lens) or the sample can be moved. Right now, the focusing device (objective lens) is moved stepwise in regards to the fixed sample.
  2D imaging along the optical axis (Z) can begin at any point in the sample and end at any point of the sample within the region of interest.
    the current movement is though depending on the application:
      (a) begin scanning a 2D scan of the top layer of the tissue sample, or
      begin scanning a little outside the sample, to be able to determine the top, or
      begin scanning within the sample, to prevent beam-sample interactions (like burning or such thing), which take place at the surface-immersion medium barrier.
      (b) then move the focusing device (objective lens) by means of a piezo in the direction of the sample in increments determined by the imaging parameters
      start at (a) again
      Stop at a point in the sample, which is determined by the imaging parameter
      Move the piezo back to its original position
      Move the sample to a different position and start with (a) again (area imaging)
  For some applications it is preferable, if the movement can be reversed (starting inside of the sample and then move out), or performed in a 'random' fashion, covering the whole area, as long as the z-position is known.
  The z position of the foci is known as the piezo position is known
  The 2D scanning is done while the z-scan from one position to the next takes place or after the z-scan has completed its move to the next position.
  Images of 2D sections can be done alone, without any 3D movement involved.
(6) Process images for feedback purposes (optional)
(7) display the images (optional)
(8) save the data
Process data before saving (Optionally)
(9) Post process the data (optional)
Image normalization
linear image deconvolution
nonlinear image deconvolution
(10) save the processed data (optional)
(11) display the processed data (optional)

In addition to mechanistic applications, time-resolved measurements, either alone or in conjunction with spectral measurements, can greatly aid in distinguishing signals from different reporter probes and processes, such as simple scattering and non-linear scattering. For cytometry applications, the additional information from time-resolved measurements can potentially increase the number of probes which can be used simultaneously, provide images cell morphology by detection of second harmonic generation, and aid in deconvolution of images from highly scattering samples.

FIGS. 29(a) and 29(c) relate to a deconvolution process. In FIG. 29(a) Illumination foci in the optical plane. (foci f11-f33 are illustrated in an enlarged) along with an object, illuminated by foci f22. In FIG. 29(b) the detection signals are scattered along with the detection areas a11-a33. FIG. 29(c) are example of signal counts detected by the associated channels of the multi channel detector (signal from area a11 is collected by the detector channel c11; a12 by c12 and so on) at a certain time point, when the focus f1 scans the center of the object (a). The relative signal distribution between the channels is dependent on the mean free path of the detection photons in the media and the penetration depth. It is constant however, if a homogeneous scattering distribution is assumed (For many samples this can de assumed in the first approximation). Low mean free path means highly scattering, means higher amount of signal in other than channel c22. As the penetration depth into the sample increases, the chance, that a photon is scattered on its way to the detector array increases and thus the described "optical cross talk" increases as well. More scattered light is found in the channels, neighboring the outer channels c11, c12, c13, c21, c23, c31, c32 and c33. The signals in these detection elements are smaller though and are not illustrated for simplicity.

FIGS. 30(a)-30(d) display a 1 dimensional (1D) deconvolution exemplifying the final 2D deconvolution executed in the linear image deconvolution. For simplification only nearest neighbors are shown. A linear convolution with a delta function with inversed side lobes (FIG. 30(c)) (Illustration only in along one channel number direction) results in a linearly de-convolved image in which only the channel c22 carries a signal. In practice, this function can either be modeled or measured. If the deconvolution process is shown for simplicity only in x direction. It will be carried out in both x and y directions, and will result in an image in which only channel c22 will carry a signal.

Assuming a homogeneously scattering material (which can be assumed for samples in the first approximation), the relative and absolute height of the peaks of the delta function is fixed for every channel at its neighbors at a certain imaging depth into the sample. As a result, xy images can be linearly de-convoluted.

The linear deconvolution of cross-talk is primarily a 2D process. The values of the weighting matrix depend on several factors. The optical contribution to the cross talk increases with increasing penetration depth. Furthermore, the channels have different sensitivities, there is electronic cross talk between channels that varies from channel to channel and other factors influence the amount of total cross talk between the channels.

The cross talk for each individual channel can be determined experimentally. An example is where, one focus illuminates the sample or a test object and the whole array of detectors detects the signal. At different penetration depths a cross talk matrix is measured for each channel. This matrix is then used to carry out the deconvolution. Data of such a measurement at the sample surface and at a penetration depth of 200 mm, can be used. The measurement is repeated for every channel for example by moving the iris from transmitting light from one single micro lens to the next (in this case for channels c11 to c33). Similar alternative methods are also possible, for example by illuminating with all of the foci but using a sample with large object spacing. Furthermore, models can also replace experimental determination.

An entire 2D image consists of collections of ensembles for a non linear deconvolution, of pixels, from each detector. The key point is that relationships between entire ensembles, and certain regions of pixels between ensembles, can be established to constrain the variation of the weighting matrix to aid convergence without assumptions, or with minimal assumptions, of the sample or the processes which cause the variation in the weighting matrix.

For example, continuity of the values across the boundaries of the ensemble can be generally required. In the case with the minimal assumption that the objects under observation are smaller than the region covered by an individual ensemble, the ensembles can be considered largely independent, except due to the cross-talk introduced by the weighting matrix. The ideal image can be recovered by simultaneously solving for a weighting matrix which minimizes the covariance between ensembles. In the other case where the objects under observation are of similar size or larger than the regions covered by the ensembles, minimal models of the object (such as from image morphology or segmentation of the collected image, etc . . . ) can be used to form constraints.

Additional model dependent and independent constraints can also be applied by consideration of the planes above and below the plane under evaluation. Further constraints can also be applied to the weighting matrix from either general (such as continuation, smoothness, sharpness, etc . . . ) or model based considerations.

While this invention has been particularly shown and described with reference to preferred embodiments thereof, it will be understood by those skilled in the art that various changes in form and details may be made therein without departing from the scope of the invention encompassed by the appended claims.

What is claimed is:

1. A multiphoton imaging system comprising:
a multiphoton light source emitting light for illuminating a biological material with multiphoton light excitation to induce a fluorescence emission at one or more foci;
a focusing lens system including an actuator coupled to an objective lens that receives light from the multiphoton light source is configured to place the one or more foci at selected depth positions within the biological material;
a scanner that provides relative movement between one or more foci receiving the illuminating light and the material to be imaged at the selected depth, the scanner configured to place the one or more foci at selected horizontal and vertical positions within the biological material, the placement of the one or more foci in horizontal, vertical, and depth positions enabling generation of three dimensional image data;
an optical system that couples light from the scanner onto a region of interest of the material, the optical system including a moveable lens to adjust focal depth in the biological material;
a detector system that detects light from the region of interest to generate image data at a plurality of different wavelengths, the detector system including a plurality of photomultiplier tube detector elements, including a first photomultiplier tube detector element that is optically coupled to the region of interest with a first optical fiber and a second photomultiplier tube detector element that is coupled to the region of interest with a second optical fiber;

a holder for the biological material, the holder being mounted on a controllable stage;

a sectioning system for sectioning the biological material;

a controller connected to the scanner, the light source, the focusing lens system, and the controllable stage to automatically control the imaging system; and an image processor connected to the detector system that processes image data detected at different focal depths, different horizontal and vertical positions, and at different wavelengths in the biological material to generate the three dimensional image data.

2. The system of claim 1 wherein the detector system comprises a plurality of detector elements each detector element being optically coupled to the material with an optical fiber.

3. The system of claim 1 wherein each detector element detects light from a different focal location.

4. The system of claim 1 wherein each detector element comprises a photomultiplier tube.

5. The system of claim 1 wherein each detector element has a detection area and a detector spacing separating each detector element from an adjacent detector element.

6. The system of claim 1 wherein the detector system comprises a multi-anode photomultiplier tube imaging detector having at least 64 detector elements.

7. The system of claim 1 wherein the optical system illuminates at least 4 spatially separated foci in a 2×2 scan pattern.

8. The system of claim 1 wherein the system performs spatially multiplexed imaging.

9. The system of claim 1, wherein the optical system simultaneously illuminates a plurality of spatially separated foci.

10. The system of claim 1 wherein controller alternates between excitation foci patterns and wherein the system illuminates foci at different depths.

11. The system of claim 1 wherein the detector system detects non-descanned light from the material in response to the illuminating light.

12. The system of claim 1 wherein the optical system comprises a diffractive optical element.

13. The system of claim 1, wherein the system illuminates foci at a first focal depth and a second focal depth.

14. The system of claim 1 wherein the scanning system scans a plurality of foci in a linear array.

15. The system of claim 1 further comprising a data storage device that stores image data and metadata including foci spacing, foci number, and scanner data.

16. The system of claim 1 further comprising recording of focal positions for the scanner position and the stage position at each focal position scanned by the scanner.

17. The system of claim 1 wherein the system is configured to perform time multiplexed illumination, the time multiplexed illumination comprising illuminating a plurality of focal locations in the material.

18. The system of claim 17 wherein a plurality of beam paths illuminate a plurality of foci, at least one beam path transmitting a first pulse that is temporally separated from a second pulse, and wherein the detector system detects the first pulse and the second pulse.

19. The system of claim 1 wherein the system is configured to perform time multiplexed detection.

20. The system of claim 1 wherein each optical fiber is coupled to a separate foci of a foci pattern.

21. The system of claim 1 further comprising an illumination fiber optic device that couples light from the light source to the material.

22. The system of claim 1 wherein light from each foci is coupled to the first or second optical fiber with a lens element.

23. The system of claim 1 wherein the scanner is a resonant mirror scanner.

24. A multifocal light detecting system comprising:

a multiphoton light source system that illuminates a material with a plurality of light pulses such that at least two photons at each of a plurality of focal locations located at a selected depth within the material induce fluorescence at each focal location;

a multifocal optical device that provides a plurality of pulsed light beams at a pulse rate at each of the plurality of focal locations;

an optical system including a focusing lens system having an actuator coupled to an objective lens that couples the plurality of pulsed light beams from the multifocal optical device onto a region of interest of the material at a plurality of focal locations at a selected adjustable depth within the material;

a scanner system configured to place the plurality of focal locations at selected horizontal and vertical positions on the material;

a control system connected to the multiphoton light source system, the scanner system, and the focusing lens system, the control system automatically controlling the multiphoton light source system output power as a function of light penetration depth in the material;

a detector device that detects fluorescent light from the plurality of focal locations in the region of interest with a plurality of detectors to generate three-dimensional image data at a plurality of different wavelengths, the detected fluorescent light being emitted in response to the pulsed light beam; and a processor connected to the detector that processes the three-dimensional image data.

25. The system of claim 24 wherein the scanner system comprises a rotating mirror or a resonant mirror.

26. The system of claim 24 wherein each detector in the plurality of detectors has a collection area corresponding to a scattering distribution for a corresponding focal location in the plurality of focal locations.

27. The system of claim 24 wherein the detector device detects time resolved data for deconvolutions.

28. The system of claim 24 wherein the processor is configured to execute a computer program that processes time resolved data in combination with spectroscopic data to distinguish components of tissue.

29. A method for multifocal light detection in response to light from a multiphoton light source system comprising:

illuminating a region of interest with light from a multiphoton light source system using a plurality of scanning optical pathways to form a plurality of scanning focal locations at selected horizontal and vertical positions within the region of interest with a multifocal optical device including a focusing lens system having an actuator coupled to an objective lens to place the plurality of scanning focal locations at a selected adjustable depth within the region of interest, the scanning focal locations simultaneously moving in tissue in response to control signals from a controller;

simultaneously detecting fluorescent light from each of the plurality of focal locations in the region of interest in response to pulsed light illumination including at least two photons received at each focal location required to induce fluorescence at a given time during scanning, the fluorescent light being detected with a first detector array that detects a first spectral component having at least a first wavelength and a second detector array that detects a second spectral component having at least a second wavelength, the first spectral component being spectrally distinct from the second spectral component; and processing the first spectral component and the second spectral component to generate a plurality of spectral images of the tissue including three dimensional image data at different wavelengths.

30. The method of claim 29 further comprising actuating relative movement between the pathways and a material by scanning with a rotating mirror or a resonant mirror.

31. The method of claim 29 further comprising detecting with the first detector array having a plurality of detector elements, each detector element having a collection area corresponding to a scattering distribution for each of the plurality of scanning focal locations and collecting time realized data and fluorescence data.

32. The method of claim 29 further comprising detecting light with the first detector array that comprises a plurality of photomultiplier tube detector elements.

33. The method of claim 29 further comprising actuating the multiphoton light source system that emits light at a wavelength such that at least two photons of light that are incident at a focal location of a material within the region of interest induce a fluorescence emission from a material.

* * * * *

UNITED STATES PATENT AND TRADEMARK OFFICE
CERTIFICATE OF CORRECTION

PATENT NO. : 10,598,597 B2
APPLICATION NO. : 15/815536
DATED : March 24, 2020
INVENTOR(S) : Bahlman et al.

Page 1 of 1

It is certified that error appears in the above-identified patent and that said Letters Patent is hereby corrected as shown below:

In the Specification

In Column 1, Lines 14-17, delete:
"This invention was made with government support under grant numbers R33 CA84740 and R33 CA91354 awarded by the National Institutes of Health. The government has certain rights in this invention."

And insert:
-- This invention was made with government support under CA084740 and CA091354 awarded by the National Institutes of Health. The government has certain rights in the invention. --

Signed and Sealed this
Twenty-fifth Day of November, 2025

John A. Squires
*Director of the United States Patent and Trademark Office*